US009494601B2

(12) United States Patent
McKnight et al.

(10) Patent No.: US 9,494,601 B2
(45) Date of Patent: Nov. 15, 2016

(54) ATYPICAL HEMOLYTIC UREMIC SYNDROME (AHUS) BIOMARKER PROTEINS

(71) Applicant: Alexion Pharmaceuticals, Inc., Cheshire, CT (US)

(72) Inventors: Susan Faas McKnight, Old Lyme, CT (US); Roxanne Cofiell, Glastonbury, CT (US); Anjli Kukreja, Fairfield, CT (US); Krystin A. Bedard; Yan Yan, Cheshire, CT (US)

(73) Assignee: Alexion Pharmaceuticals, Inc., New Haven, CT (US)

( * ) Notice: Subject to any disclaimer, the term of this patent is extended or adjusted under 35 U.S.C. 154(b) by 0 days.

(21) Appl. No.: 15/013,833

(22) Filed: Feb. 2, 2016

(65) Prior Publication Data
US 2016/0154009 A1 Jun. 2, 2016

Related U.S. Application Data

(63) Continuation of application No. 14/453,268, filed on Aug. 6, 2014.

(60) Provisional application No. 61/913,180, filed on Dec. 6, 2013, provisional application No. 61/863,299, filed on Aug. 7, 2013.

(51) Int. Cl.
*G01N 31/00* (2006.01)
*G01N 33/53* (2006.01)
*G01N 33/68* (2006.01)
*C07K 16/18* (2006.01)
*A61K 39/00* (2006.01)

(52) U.S. Cl.
CPC ........... *G01N 33/6893* (2013.01); *C07K 16/18* (2013.01); *A61K 2039/505* (2013.01); *C07K 2317/21* (2013.01); *C07K 2317/24* (2013.01); *C07K 2317/54* (2013.01); *C07K 2317/55* (2013.01); *C07K 2317/622* (2013.01); *C07K 2317/626* (2013.01); *G01N 2333/4716* (2013.01); *G01N 2333/485* (2013.01); *G01N 2333/522* (2013.01); *G01N 2333/545* (2013.01); *G01N 2333/5412* (2013.01); *G01N 2333/5421* (2013.01); *G01N 2333/5434* (2013.01); *G01N 2333/57* (2013.01); *G01N 2333/70503* (2013.01); *G01N 2333/70525* (2013.01); *G01N 2333/70539* (2013.01); *G01N 2333/7151* (2013.01); *G01N 2333/7452* (2013.01); *G01N 2333/75* (2013.01); *G01N 2333/775* (2013.01); *G01N 2333/8139* (2013.01); *G01N 2333/8146* (2013.01); *G01N 2333/974* (2013.01); *G01N 2800/226* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| 4,686,100 | A | 8/1987 | Raffin et al. |
|---|---|---|---|
| 5,135,916 | A | 8/1992 | Sims et al. |
| 5,660,825 | A | 8/1997 | Sims et al. |
| 6,169,068 | B1 | 1/2001 | Levin et al. |
| 6,355,245 | B1 | 3/2002 | Evans et al. |
| 7,361,339 | B2 | 4/2008 | Bell |
| 7,482,435 | B2 | 1/2009 | Bowdish et al. |
| 7,833,525 | B2 | 11/2010 | Shenoy et al. |
| 8,241,628 | B2 | 8/2012 | Diefenbach-Streiber et al. |
| 2003/0049683 | A1 | 3/2003 | Bowdish et al. |
| 2005/0036691 | A1 | 2/2005 | Cathier |
| 2005/0036991 | A1 | 2/2005 | Fodor |
| 2005/0191298 | A1 | 9/2005 | Bell et al. |
| 2005/0221382 | A1 | 10/2005 | Rother |
| 2005/0271660 | A1 | 12/2005 | Wang |
| 2007/0110757 | A1 | 5/2007 | Wei et al. |
| 2008/0318841 | A1 | 12/2008 | Chtourou et al. |
| 2009/0028850 | A1 | 1/2009 | Rother et al. |
| 2009/0041764 | A1 | 2/2009 | Spuler et al. |
| 2010/0120665 | A1 | 5/2010 | Kaleko et al. |
| 2010/0135992 | A1 | 6/2010 | Rother et al. |

(Continued)

FOREIGN PATENT DOCUMENTS

| CN | 102170906 A | 8/2011 |
|---|---|---|
| EP | 0411306 A1 | 2/1991 |

(Continued)

OTHER PUBLICATIONS

Adam, S. et al., "D-dimer antigen: current concepts and future prospects," Blood, vol. 113(13), pp. 2878-2887 (2009).
Alexion Announces Presentation of Preliminary Results from Phase 1 Pilot Study of Eculizumab Treatment of Patients with Paroxysmal Nocturnal Hemoglobinuria; [online]; Alexion Pharmaceuticals: News; [Retrieved on Jun. 18, 2003]. Retrieved from the Internet: http://alexionpharmaceuticals.com/news/sub press.cfm? prid=242& selectyear=2002.

(Continued)

*Primary Examiner* — Lisa Cook
(74) *Attorney, Agent, or Firm* — Nelson Mullins Riley & Scarborough LLP; Jane E. Remillard, Esq.; Jill Gorny Sloper, Esq.

(57) ABSTRACT

The disclosure provides biomarker proteins, a change in the concentration or activity level of which are associated with atypical hemolytic uremic syndrome (aHUS) or clinically meaningful treatment of aHUS with a complement inhibitor. Also provided are compositions and methods for interrogating the concentration and/or activity of one or more of the biomarker proteins in a biological fluid. The compositions and methods are useful for, among other things, evaluating risk for developing aHUS, diagnosing aHUS, determining whether a subject is experiencing the first acute presentation of aHUS, monitoring progression or abatement of aHUS, and/or monitoring response to treatment with a complement inhibitor or optimizing such treatment.

19 Claims, 37 Drawing Sheets

(56) References Cited

U.S. PATENT DOCUMENTS

| | | |
|---|---|---|
| 2012/0225056 A1 | 9/2012 | Rother et al. |
| 2015/0079613 A1 | 3/2015 | McKnight et al. |

FOREIGN PATENT DOCUMENTS

| | | |
|---|---|---|
| WO | 91/15221 A1 | 10/1991 |
| WO | 92/10205 A1 | 6/1992 |
| WO | 2004/022096 A1 | 3/2004 |
| WO | 2004/029207 A2 | 4/2004 |
| WO | 2005074607 A2 | 8/2005 |
| WO | 2005/110481 A2 | 11/2005 |
| WO | 2007/038995 A1 | 4/2007 |
| WO | 2007/103134 A2 | 9/2007 |
| WO | 2007/149567 A2 | 12/2007 |
| WO | 2008/106644 A2 | 9/2008 |
| WO | 2008/153962 A2 | 12/2008 |
| WO | 2008/154251 A2 | 12/2008 |
| WO | 2009/056631 A2 | 5/2009 |
| WO | 2010/015608 A1 | 2/2010 |
| WO | 2010/054403 A1 | 5/2010 |
| WO | 2010/136311 A2 | 12/2010 |
| WO | 2011/137395 A1 | 11/2011 |
| WO | 2011/143637 A1 | 11/2011 |
| WO | 2011/163412 A1 | 12/2011 |
| WO | 2015/021166 A2 | 2/2015 |

OTHER PUBLICATIONS

Alexion Announces Results of Clinical Trial in Paroxysmal Nocturnal Hemoglobinuira Presented at the American Society of Hematology Annual Meeting; [online]; Alexion Pharmaceuticals, Inc.; [Retrieved on Jun. 17, 2003]; Retrieved rom the Internet: http://www.noonanrusso.com/news/view newsitem .aspx? I tem ID =382.

Alexion Pharmaceuticals Signs Agreement with Lonza Biologics for Commercial Manufacturing; [online]; Alexion Pharmaceuticals Inc.; [Retrieved on Jun. 17, 2003]; Retrieved from the Internet: http://www.noonanrusso.com/news/viewnewsitem.aspx?ItemID=394.

Alexion Pharmaceuticals: Complement Inhibitors; [online]; [Retrieved on Jun. 17, 2003]; Retrieved from the Internet: <http://www.alexionpharm.com/techplat/complement.cfm>.

Alexion receives FDA, European approval for orphan drug status of new treatment for paroxysmal nocturnal hemoglobinuria, Transplant News, Jan. 15, 2004, XP002497241, llfindarticles.com/g/articles/mi mOYUG/is 1 14/ai 17208612 <httg:llfindarticles.com/g/articles/mi mOYUG/is 1 14/ai 17208612>> [retrieved on Sep. 25, 2008].

Alexion Reports Presentation of Membranous Nephritis Clinical Trails; [online]; Alexion Pharmaceuticals: News; [Retrieved on Jun. 17, 2003]. Retrieved from the Internet: http://www.alexionpharm.com/news/sub press.cfm?prid=241&selectyear=2002.

Araten, D. et al., "High incidence of thrombosis in African-American and Latin-American patients with paroxysmal nocturnal haemoglobinuria," Thromb Haemost, vol. 93, pp. 88-91 (2005).

Artz, M. et al., "Renal Transplantation in Patients with Hemolytic Uremic Syndrome: High Rate of Recurrence and Increased Incidence of Acute Rejections," Transplantation, vol. 76 (5), pp. 821-826 (2003).

Atkinson, J., "Complement factor H and the hemolytic uremic syndrome," Journal of Experimental Medicine, vol. 204(6), pp. 1245-1248 (2007).

Audebert, H. et al., "Cerebral ischemic infarction in paroxysmal nocturnal hemoglobinuria," J. Neurol, vol. 252(1), pp. 1379-1386 (2005).

Becker, S. et al., "HIV-Associated Thrombotic Microangiopathy in the Era of Highly Active Antiretroviral Therapy: An observational Study," Clinical Infectious Diseases, vol. 39 pp. S267-S275 (2004).

Blom, A. et al. "A Novel Non-Synonymous Polymorphism (p.Arg240His) in C4b-Binding Protein Is Associated with Atypical Hemolytic Uremic Syndrome and Leads to Impaired Alternative Pathway Cofactor Activity," The Journal of Immunology, vol. 180(9), pp. 6385-6391 (2008).

Breslin, E., et al., "Outcome of Renal Transplantation in Patients with Non-Shiga Toxin-Associated Hemolytic Uremic Syndrome: Prognostic Significance of Genetic Background," Clin J. Am Soc Nephrol, vol. 1, pp. 88-99 (2006).

Brodsky, R.A., "New Insights into paroxysmal nocturnal hemoglobinuria," American Society of Hematology, vol. 516, pp. 24-28 (2006).

Caprioli, J. et al., "Genetics of HUS: the impact of MCP, CFH, and IF mutations on clinical presentation, response to treatment, and outcome," Blood, vol. 108 (4), pp. 1267-1279 (2006).

Caprioli, J. et al., "The Molecular Basis of Familial Hemolytic Uremic Syndrome: Mutation Analysis of Factor H Gene Reveals a Hot Spot in Short Consensus Repeat 20," Journal of Am Soc Nephrol, vol. 12, p. 297-307 (2001).

Chatelet, V. et al. "Safety and long-term efficacy of eculizumab in a renal; transplant patient with recurrent atypical hemolytic-uremic syndrome," American Journal of Transplantation, vol. 9(11) pp. 2644-2645, (2009) XP002739219.

Chen, N., et al., "C5L2 is critical for the biological activities of the anaphylatoxins C5a and C3a," Nature, vol. 446 (7132), pp. 203-207 (2007).

Clague, C.T. et al, "A low-hemolysis blood aspirator conserves blood during surgery," Biomed. Insrum. Technol., vol. 29(5), pp. 419-424 (1995).

Clinics, Biotechnology News, vol. 24(30), p. 10 (2004).

Cofiell, R., "Nephrology Dialysis Transplantation," Proceedings from 51st Congress of the European-Renal-Association (ERA)/European Dialysis-and-Transplant-Association, pp. 1-18 (2014).

Cofiell, R., "Biomarkers of Complement and Endothelial Activation, Inflammation, Thrombosis and Renal Injury in Patients (pts) With aHUS Treated With Eculizumab (ECU)," Blood, vol. 122 (21), 2 pages (2013).

Cofiell, R., Database Biosis Biosciences Information Service, 2 pages (2013).

Collard, C. et al., "Endothelial nuclear factor-KB translocation and vascular cell adhesion molecule- induction by complement: inhibition with anti-human C5 therapy or cGMP analogues," Art. Thromb. Vas., vol. 19, pp. 2623-2629 (1999).

Constantinescu, A. et al., "Non-Enteropathic Hemolytic Uremic Syndrome:; Causes and Short-Term Course," American Journal of Kidney Disease, vol. 43 (6) pp. 976-982 (2004).

Dmytrijuk, A., et al, "FDA Report: Eculizumab (Soliris) for the Treatment of Patients with Paroxysmal Nocturnal Hemoglobinuria," The Oncologist, vol. 13(9), pp. 993-1000 (2008).

Dodaro-Surrusco et al. "A patient guide: what to expect after a kidney transplant," pp. 1-76 (1995).

Dragon-Durey, M. et al., "Anti-Factor H Autoantibodies Associated with Atypical Hemolytic Uremic Syndrome," Journal of American Society of Nephrology, vol. 16, pp. 555-563 (2005).

Eculizumab: 5G1.1, h5G1.1, Long-Acting Anti-C5 Monoclonal Antibody 5G1-1, Long-Acting Anti-C5 Monoclonal Antibody 5G1.1, Drugs in R&D 2007, LNKD-Pubmed: 17249850, vol. 8(1), pp. 61-68, XP009161624 (2007).

Esparza-Gordillo, J. et al., "Predisposition to atypical hemolytic uremic syndrome involves the concurrence of different susceptibility alleles in the regulators of complement activation gene cluster in 1q32, Human Molecular Genetics," Human Molecular Genetics, vol. 14 (5), pp. 703-712 (2005).

European Extended Search Report. EP 15152757.9-1412. dated May 20, 2015. pp. 1-12.

Extended European Search Report. EP15152758.7, dated May 20, 2015, pp. 1-10.

Faas, S. J. et al., "Reduction of Biomarkers Related to Thrombotic Microangiopathy in Patients with AHUS Treated with Eculizumb," Haematologica, vol. 99 (S1) P1232, pp. 473-474 (2014).

Figueroa, J.E., et al., "Infectious Diseases Associated with Complement Deficiencies," Clinical Microbiology Reviews, vol. 4(3), pp. 359-395 (1991).

Fitch, J. et al., "Pharmacology and biological efficacy of a recombinant, humanized, single-chain antibody C5 complement inhibitor

(56) References Cited

OTHER PUBLICATIONS in patients undergoing coronary artery bypass graft surgery with cardiopulmonary bypass," Circulation, vol. 100(25), pp. 2499-2506 (1999).
Fremeaux-Bacchi, V. et al., "Complement factor I: a susceptibility gene for atypical haemolytic uraemic syndrome," J Med Genet, vol. 41(e84), pp. 1-6 (2004).
Fremeaux-Bacchi, V. et al., "Genetic and Functional Analyses of Membrane Cofactor Protein (CD46) Mutations in Atypical Hemolytic Uremic Syndrome," Journal of American Society, vol. 17, pp. 2017-2025 (2006).
Garba, I.H., et al "Total serum lactate dehydrogenase activity in acute Plasmodium falciparum malaria infection," Singapore Medical J., vol. 46(11), pp. 632-634 (2005).
Garcia, M. et al., "Effect of Preservatives on IgG aggregation, Complement-activating Effect and Hypotensive Activity of Horse Polyvalent Antivenom Used in Snakebite Envenomation," Biologicals, vol. 30, pp. 143-151 (2002).
Genes and Disease; [online]; Paroxysmal nocturnal hemoglobinuria; [Retrieved on Jun. 17, 2003]. Retrieved from the Internet: <http://www.ncbi.nlm.nih.gov/disease/PNH.html>.
George, J. et al., "The association of pregnancy with thrombotic thrombocytopenic purpura-hemolytic uremic syndrome," Curr Opin Hematol, vol. 10, pp. 339-344 (2003).
Goicoechea De Jorge, E. et al. "Activation is Required for Development of Atypical Haemolytic Uraemic Syndrome in CIH," Molecular Immunology, vol. 45, No. 16, Abstract 016, pp. 4100-4101 (2008).
Goicoechea De Jorge, E. et al., "Gain-of-function mutations in complement factor B are associated with atypical hemolytic uremic syndrome," PNAS, USA, vol. 104(1), pp. 240-245 (2007).
Gottschall, J. et al., "Quinine-Induced Immune Thrombocytopenia with Hemolytic Uremic Syndrome: Clinical and Serological Findings in Nine Patients and Review of Literature," American Journal of Hematology, vol. 47, pp. 283-289 (1994).
Gruppo, R. et al., "Eculizumab for 1-18 Congenital Atypical Hemolytic-Uremic Syndrome," New England Journal of Medicine, vol. 360 (5), pp. 544-546, ( 2009) XP055186116.
Hall, C. et al., "Primary prophylaxis with warfarin prevents thrombosis in paroxysmal nocturnal hemoglobinuria (PNH)," Blood, vol. 102 (10), pp. 3587-3591 (2003).
Harding, J., "Eculizumab," Drugs of the Future, Prous Science, vol. 29(7), pp. 673-676, (2004).
Hill, A. et al., "Improvement in the symptoms of smooth muscle dystonia during eculizumab therapy in paroxysmal nocturnal hemoglobinuria," Haematologica, vol. 90(12): Abstract #ECR40 (2005).
Hill, A. et al., "Nitric Oxide Consumption and Pulmonary Hypertension in Patients with Paroxysmal Nocturnal Hemoglobinuria," 47th Annual Meeting of the American Society of Hematology, Dec. 10-13, 2005, Blood, vol. 106, Abstract 1046, 1 page, (2005).
Richards, A. et al., "Factor H Mutations in Hemolytic Uremic Syndrome Cluster in Exons 18-20, a Domain Important for Host Cell Recognition," Am. J. Hum. Genet,, vol. 68, pp. 485-490 (2001).
Richards, A. et al., "Mutations in human complement regulator, membrane cofactor protein (CD46), predispose to development of familial hemolytic uremic syndrome," PNAS, USA, vol. 100 (22), pp. 12966-12971 (2003).
Richards, S. et al., "Evolution of GPI-Deficient Clones Predicts Clinical Course in Paroxysmal Nocturnal Haemoglobinuria," Blood, vol. 104, Abstract 172 (2004).
Rodary, C. et al., "Patient preference for either the EORTC QLQ-C30 or the FACIT Quality of Life (QOL) measures: a study performed in patient suffering from carcinoma of an unknown primary site (CUP)," European Journal of cancer, vol. 40, pp. 521-528 (2004).
Rookmaaker, M. et al., "Met-RANTES reduces endothelial progenitor cell homing to activated (glomerular) endothelium in vitro and in vivo," Am J Physiol Renal Physiol, vol. 293(2), pp. F624-F630 (2007).
Rosse, W. et al., "Immune-mediated hemolytic anemia," Hematology Am Soc Hematol Educ Program, 48-62 (2004) XP002497825.
Rosse, W.F. "A new way to prevent thrombosis?," Blood, vol. 110, No. 12, pp. 3821-3821, Dec. 1, 2007, XP055187205.
Bother, R. et al., "The clinical sequelae of intravascular hemolysis and extracellular plasma hemoglobin," JAMA, vol. 293(13), pp. 1653-1662 (2005).
Rother, R. et al., Discovery and development of the complement inhibitor eculizumab for the treatment of paroxysmal nocturnal hemoglobinuria, Nature Biotechnology, vol. 25(11), pp. 1256-1264 (2007).
Rother, R., et al., "Eculizumab, a C5 complement-blocking antibody, abolishes hemolysis and reduces transfusion dependency in patients with paroxysmal nocturnal hemoglobinuria (PNH)," Molecular Immunology, vol. 40(2-4), p. 197; XP009163498, (2003).
Shin, J. et al., "More on Eculizumab for Congenital Atypical Hemolytic-Uremic Syndrome," New England Journal of Medicine, vol. 360, 2009, pp. 2142-2143, XP055186122.
Stebler, C. et al., High-dose recombinant human erythropoietin for treatment of anemia in myelodysplastic syndromes and paroxysmal nocturnal hemoglobinuria: a pilot study, Exp. Hematol., vol. 18, pp. 1204-1208 (1990).
Strauss, R. et al., "Alternative pathway of complement in sickle cell disease," Pediat. Res. vol. 11, pp. 285-289 (1977).
Stuart, M. et al., "Sickle-cell disease," Lancet, vol. 364, pp. 1343-1360 (2004).
Taheri, D. et al. "Recurrence of hemolytic-uremic syndrome following live related renal transplantation" Arch Iran Vied, vol. 9(2), pp. 170-172 (2006).
Tang, X. et al., "Design of Freeze-Drying Processes for Pharmaceuticals: Practical Advice," Pharmaceutical Research, vol. 21 (2), pp. 191-200 (2004).
Thomas, T. et al., "Inhibition of complement activity by humanized anti-C5 antibody and single- chain Fv, Molecular Immunology," vol. 33(17-18), pp. 1389-1401 (1996).
Vakeva, A. et al., "Myocardial infarction and apoptosis after myocardial ischemia and reperfusion," Circulation, vol. 7, pp. 2259-2267 (1998).
Valavaara, R. et al., "Renal Complications of Mitomycin C Therapy with Special Reference to the Total Dose," cancer, vol. 55, pp. 47-50 (1985).
Ward, P. et al., "Complement-Derived Leukotactic Factors in Inflammatory Synovial Fluids of Humans," The Journal of Clinical Investigations, vol. 50(3), pp. 606-616 (1971).
Ward, P. et al., "Functions of C5a receptors," J. Mol. Med. vol. 87(4), pp. 375-378 (2009).
Warwicker, P. et al., "Genetic studies into inherited and sporadic hemolytic uremic syndrome," Kidney International, vol. 53, pp. 836-844 (1998).
Weitz, M. et al., "Prophylactic eculizuluab prior to kidney transplantation for atypical hemolytic uremic syndrome," Pediatr. Nephrol., vol. 26, pp. 1325-1329 (2011).
Whiss, P., "Pexelizumab Alexion," Current Opinion in Investigative Drugs, vol. 3(6), pp. 870-877 (2002).
Wurzner, R. et al., "Inhibition of Terminal Complement Complex Formation and Cell Lysis by Monoclonal Antibodies," Complement Inflamm., vol. 8, pp. 328-340 (1991).
Wurzner, R. et al., "Therapeutic strategies for atypical and recurrent hemolytic uremic syndromes (HUS)," complement and Kidney Disease, pp. 149-163, (2006) XP009161632.
Zuber, J. et al., "Use of eculizumab for atypical haemolytic uraemic syndrome and C3 glomerulopathies," Nature Reviews Nephrology, vol. 8(11), pp. 643-657 (2012).
Hill, A. et al., "Protection of erythrocytes from human complement-mediated lysis by membrane targeted recombinant soluble CD59: a new approach to PNH therapy," Blood, vol. 107(5), pp. 2131-2137 (2006).
Hill, A. et al., "Sustained Control of Hemolysis and Symptoms and Reduced Transfusion Requirements over a Period of 2 Years in Paroxysmal Nocturnal Hemoglobinuria (PNH) with Eculizumab Therapy," Blood, vol. 104, Abstract 2823 (2004) with ASH poster final 2004.ppt.

(56) References Cited

OTHER PUBLICATIONS

Hill, A. et al., "Sustained response and long-term safety of eculizumab in paroxysmal nocturnal hemoglobinuria," Blood, vol. 106(7), pp. 2559-2565 (2005).
Hill, A., et al., "Eculizumab, for the treatment of paroxysmal nocturnal hemglobinuria," Clin. Adv. In Hemal. & Onc., vol. 3 (11), pp. 849-850 (2005).
Hillmen, P. et al. "Eculizumab, a C5 complement blocking antibody, is the first therapy to reduce transfusion requirements in patients with paroxysmal nocturnal haemoglobinuria (PNH)," British Journal of Haematology, vol. 121, (Supplement 1), p. 87, XP009144758 (2003). 43rd Annual Scientific Meeting of the British Society for Haematology, Apr. 7-9, 2003.
Hillmen, P. et al., "Eculizumab, a C5 Complement-Blocking Antibody, Controls Hemolysis in Paroxysmal Nocturnal Hemoglobinuria (PNH) with Responses Maintained over prolonged Period of Therapy," Journal of the American Society of Hematology, vol. 102(11), Abstract 1858 (2003).
Hillmen, P. et al., "Effect of the complement inhibitor eculizumab on thromboembolism in patients with paroxysmal nocturnal hemoglobinuria," Blood, vol. 110(12), pp. 4123-4128 (2007).
Hillmen, P. et al., "The complement inhibitor eculizumab in paroxysmal nocturnal hemoglobinuria," The New England Journal of Medicine, vol. 355(12) pp. 1233-1243 (2006).
Hillmen, P., "Effect of Eculizumab on Hemolysis and Transfusion Requirements in Patients with Paroxysmal Nocturnal Hemoglobinuria," The New England Journal of Medicine, vol. 350(6), pp. 552-559 (2004).
Hillmen, P., et al., "Eculizumab, a C5 Complement blocking Antibody, Abolishes Hemolysis and Renders Hemolytic Patients with Paroxysmal Nocturnal Hemoglobinuria (PNH) Transfusion Independent," 44th ASH Annual Meeting. Blood, vol. 100 (11) (Abstract No. 154) (2002).
Hillmen, P., et al., "The terminal complement inhibitor eculizumab reduces thrombosis in patients with paroxysmal nocturnal hemoglobinuria," Blood 108(11):Abstract 123 (2006) XP002482084. 48th Annual Meeting of the American Society of Hematology. Dec. 9-12, 2006.
Hodgkins, K. et al., "Clinical Grand Rounds: Atypical Hemolytic Uremic Syndrome," American Journal of Nephrology, vol. 35(5), pp. 394-400 (2012).
Horvath, B. et al., "Measurement of von Willebrand factor as the marker of endothelial dysfunction in vascular diseases," Exp Clin Cardiol, vol. 9(1), pp. 31-34 (2004).
Inoue et al., "Molecular genetics of paroxysmal nocturnal hemoglobinuria," Int J Hematol., vol. 77(2), pp. 107-112. (2003).
International Search Report and Written Opinion, PCT/US2014/049957, dated Feb. 25, 2015, pp. 1-32.
Japanese Office Action, JP 2014-129867, dated May 28, 2015, pp. 1-13.
Jasinski, M. et al., "A Novel mechanisms of complement-independent clearance of red cells deficient in glycosyl phosphatidylinositol-linked proteins," Blood, vol. 103(7), pp. 2827-2834 (2004).
Kallio, E. et. al., "Blockade of complement inhibits obliterative bronchiolitis in rat tracheal allografts," American Journal of Respiratory and Critical Care Medicine, vol. 161 (4 Pt 1), pp. 1332-1339, XP002356727 (2000).
Kaplan, B. et al., "Eculizumab treatment of atypical hemolytic uremic syndrome," Expert Opinion on Orphan Drugs, vol. 1(2), pp. 167-176 (2013).
Kaplan, M., "Eculizumab Alexion," Current Opinion in Investogational Drugs, vol. 3(7), pp. 1017-1023, (2002).
Kato, G. et al., "Deconstructing sickle cell disease: reappraisal of the role of hemolysis in the development of clinical subphenotypes," Blood Reviews, vol. 21, pp. 37-47 (2007).
Kavanagh, D. et al, "Atypical haemolytic uraemic syndrome," British Medical Bulletin, vol. 77 and 78, pp. 5-22 (2006).
Kavanagh, D. et al., "Complement Regulatory Genes and Hemolytic Uremic Syndromes," Annual Review of Medicine, vol. 59. (1), pp. 293-309, (2008) XP055186136.
Kinoshita, Taroh, "Molecular pathogenesis of Paroxysmal Nocturnal Haemoglobinuria," XXVIth World Congress of the International Society of Haematology, Singapore, Aug. 25-29, 1996.
Krarup, A., "Simultaneous Activation of Complement and Coagulation by MBL-Associated Serine Protease 2," PLoS ONE, vol. 2(7), e623, pp. 1-8 (2007).
Lee, T. et al., "Neisseria meningitidis Bacteremia in Association with Deficiency of the Sixth Component," Infection and Immunity, vol. 24(3), pp. 656-660 (1979).
Loirat, C. et al., "Complement and the atypical hemolytic uremic syndrome in children," Pediatric Nephrology, Journal of the International Pediatric Nephrology Association, Springer, Berlin, DE, vol. 23. (11), pp. 1957-1972, (2008) XP019658955.
Luzzatto, L. et al., "Recent advances in biological and clinical aspects of paroxysmal nocturnal hemoglobinuria," Int. J. Hematol., vol. 84, pp. 104-112 (2006).
MacNeil, J. et al., "Eculizumab could be paroxysmal nocturnal hemoglobinuria breakthrough," 44th Annual Meeting of the American Society of Hematology, Medscape Medical News, (Dec. 13, 2002); [online]; Medscape from WebMD; [Retrieved on Jun. 17, 2003. Retrieved from the Internet: //www.medscape.com/viewarticle/446336 <http://www.medscape.com/viewarticle/446336>. XP0091 06338.
Mehla, R. et al., "Programming of neurotoxic cofactor CXCL-I 0 in HIV-I-associated dementia: abrogation of CXCL -1Q-induced neuro-glial toxicity in vitro by PKC activator," Journal of Neuroinflammation, vol. 9(239) 19 pages (2012).
Merck, Manual of Diagnosis and Therapy (The), Seventeenth Edition, Chapter 127 Anemias, pp. 849-883 (1999).
Meyers, G. et al., "Management Issues in Paroxysmal Nocturnal Hemoglobinuria," International Journal of Hematology, vol. 77, p. 125-132 (2003).
Miralbell, R. et al., "Renal Toxicity After Allogeneic Bone Marrow Transplantation: The Combined Effects of Total-Body Irradiation and Graft-Versus-Host Disease," Journal of Clinical Oncology, vol. 14 (2), pp. 579-585 (1996).
Modde, F. et al., "Comprehensive analysis of glomerular mRNA expression of pro- and antithrombotic genes in atypical haelnolytic-urelnic syndrolne (aHDS)," Virchows Arch, vol. 462(4), pp. 455-464 (2013).
Morgan, B. et al., "Complement therapeutics; history and current progress," Molecular Immunology, vol. 40(2-4), pp. 159-170, XP002687981 (2003).
Morley, B. et al., "Internal homologies of the Ba fragment from human complement component Factor B, a class III MHC antigen," The EMBO Journal, vol. 3(1), pp. 153-157 (1984).
Mortazavi, Y. et al., "The spectrum of PIG-A gene mutations in aplastic anemia/paroxysmal nocturnal hemoglobinuria (AA/PNH): a high incidence of multiple mutations and evidence of a mutational hot spot," Blood, vol. 101 (7), pp. 2833-2841 (2003).
Moyo, V. et al., "Natural history of paroxysmal nocturnal haemoglobinuria using modern diagnostic assays," British J Haematology, vol. 126, pp. 133-138 (2004).
Nangaku, M. et al., "CD59 Protects Glomerular Endothelial Cells from Immune-Mediated Thrombotic Microangiopathy in Rats," Journal of the American Society of Nephrology, vol. 9(4), pp. 590-597 (1998).
Nester, C. et al., "Atypical hemolytic uremic syndrome: what is it, how is it diagnosed, and how is it treated?" Hematology, vol. 2012, pp. 617-625 (2012).
Neumann, H. et al., "Haemolytic uraemic syndrome and mutations of the factor H gene: a registry-based study of German speaking countries," Journal of Med Genet, vol. 40, pp. 676-681 (2003).
Notice of Opposition for EP U.S. Pat. No. 1720571, dated Mar. 18, 2013.
Nurnberger, J. et al., "Eculizumab for Atypical Hemolytic-Uremic Syndrome," New England Journal of Medicine, vol. 360 (5), pp. 542-544 (2009) XP055045531.

(56) References Cited

OTHER PUBLICATIONS

Okamoto, Y. et al., "Determination of Soluble Tumor Necrosis Facto-Q Receptor Type I (TNFRI) and II (TNFRII) in the Urine of Healthy Japanese Subjects," Journal of Immunoassay and Immunochemistry, vol. 32(2), pp. 145-155 (2011).

Parker, C. et al., "Diagnosis and management of paroxysmal nocturnal hemoglobinuria," Blood, vol. 106(12), pp. 3699-3709 (2005).

Paroxysmal nocturnal hemoglobinuria, included; PNH, included phosphatidylinositol glycan, class A, pseudogene 1, included; pigap1, included piga-related processed gene, included [online]. OMIM-Online Medelian Inheritance in Man; John Hopkins University; [Retrieved on Jun. 18, 2003]. Retrieved from the Internet: <http://www.ncbi.nlm.nih.gov/entrez/query.fcgi?cmd=Retrieve&db=OMIM&dopt=detailed>.

Patel, M. et al., "Pexelizumab A novel therapy for myocardial ischemia-reperfusion," Drugs of Today, vol. 41(3), pp. 165-170 (2005).

Pratt, J.R. et al., "Effects of Complement Inhibition with Soluble Complement Receptor 1 on Vascular Injury and Inflammation during Renal Allograft Rejection in the Rat," American Journal of Pathology, vol. 149(6), pp. 2055-2066 (1996).

Rawal, N. et al., "C5 Convertase of the Alternative Pathway of Complement, Kinetic Analysis of the Free and Surface Bound Forms of the Enzyme," The Journal of Biological Chemistry, vol. 273(27), pp. 16828-16835 (1998).

Reiter, C. et al., "Cell-free hemoglobin limits nitric oxide bioavailability in sickle-cell disease," Nature Medicine, vol. 8 (12), pp. 1383-1389 (2002).

Cofiell, R., "Eculizumab Reduces Terminal Complement (TC) and Complement Alternative Pathway (CAP) Activation, Inflammation, Endothelial Damage, Thrombosis and Renal Injury in Atypical Hemolytic Uremic Syndrome (AHUS) Patients, Nephrology Dialysis Transplantation," Proceedings from 51st Congress of the European-Renal-Association (ERA)/ European Dialysis-and-Transplant-Association, Abstract MP036,pp. 1-18 (2014).

International Preliminary Report on Patentability, PCT/US2014/049957, dated Feb. 18, 2016, pp. 1-26.

Jungraithmayr, T. et al., "Successful renal transplantation in a 10 year old boy with factor H associated atypical hemolytic uremic syndrome (aHUS) with plasmapheresis and eculizumab," vol. 13, Supp. 1, p. 109, 5th Congress of the International Pediatric Transplant Association, Abstract # LB17, Apr. 18, 2009.

Mache, C. et al. "Complement Inhibitor Eculizumab in Atypical Hemolytic Uremic Syndrome," Clin J Am Soc Nephroi., vol. 4: 1312-1316 (Aug. 2009).

U.S. Appl. No. 13/128,523, Apr. 29, 2016.
U.S. Appl. No. 14/453,268, filed Aug. 6, 2014, Susan Faas McKnight.
U.S. Appl. No. 13/128,523, filed Oct. 25, 2011, Russell P. Rother.
U.S. Appl. No. 14/453,268, Feb. 1, 2016.
U.S. Appl. No. 13/128,523, Jan. 8, 2015.
U.S. Appl. No. 13/128,523, Jul. 17, 2014.
U.S. Appl. No. 13/128,523, Apr. 17, 2014 .

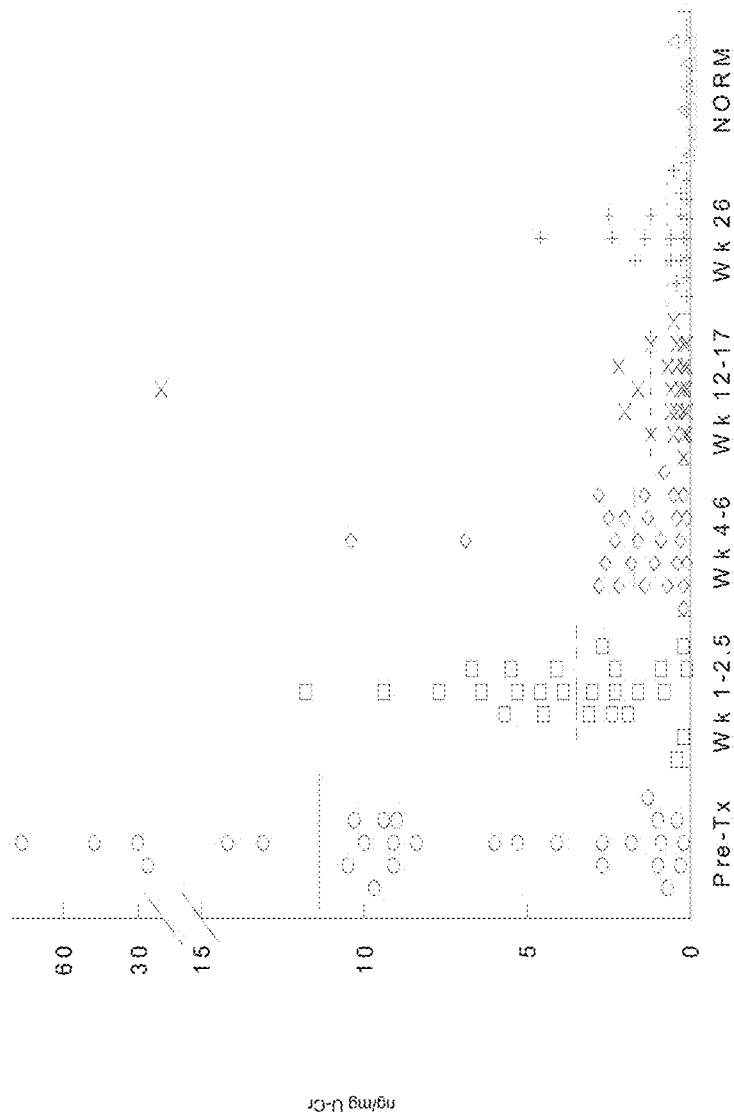

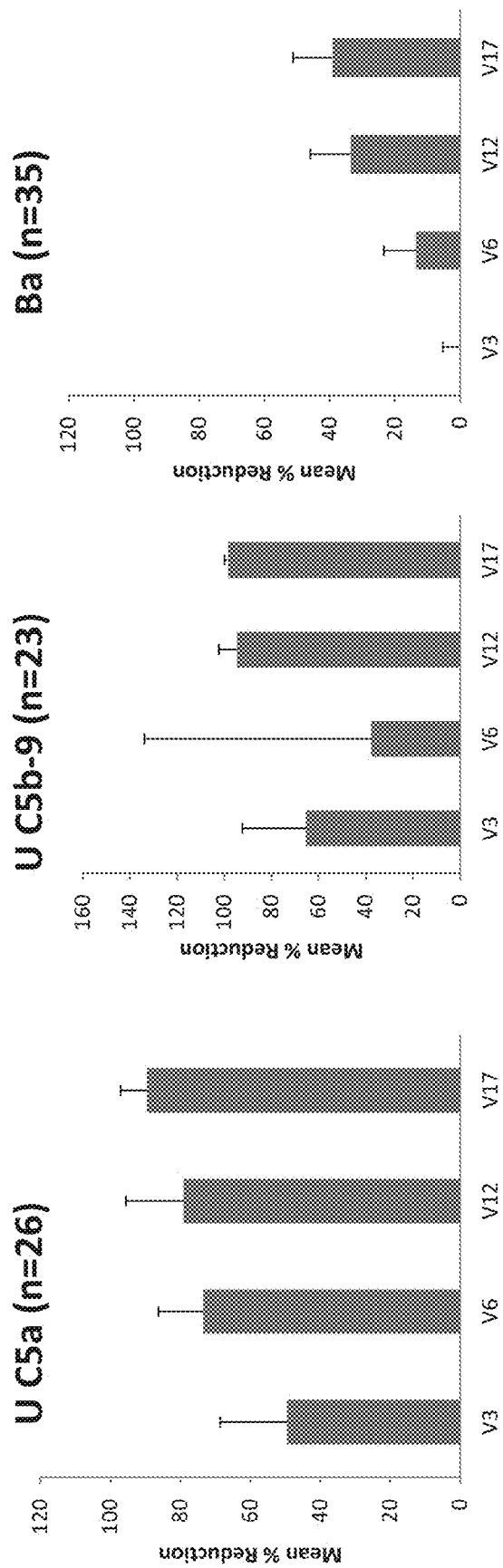

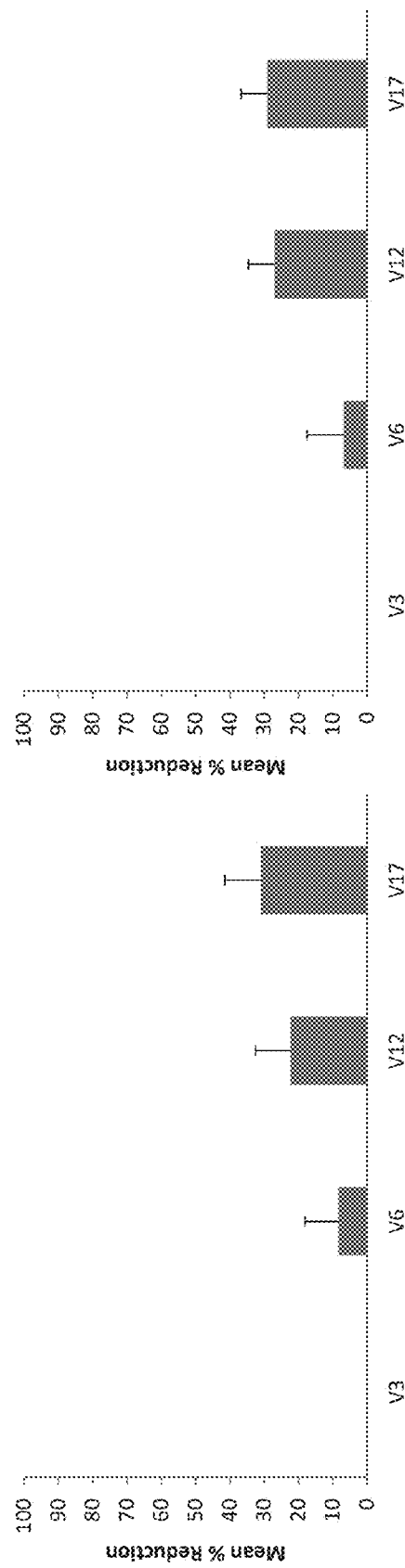

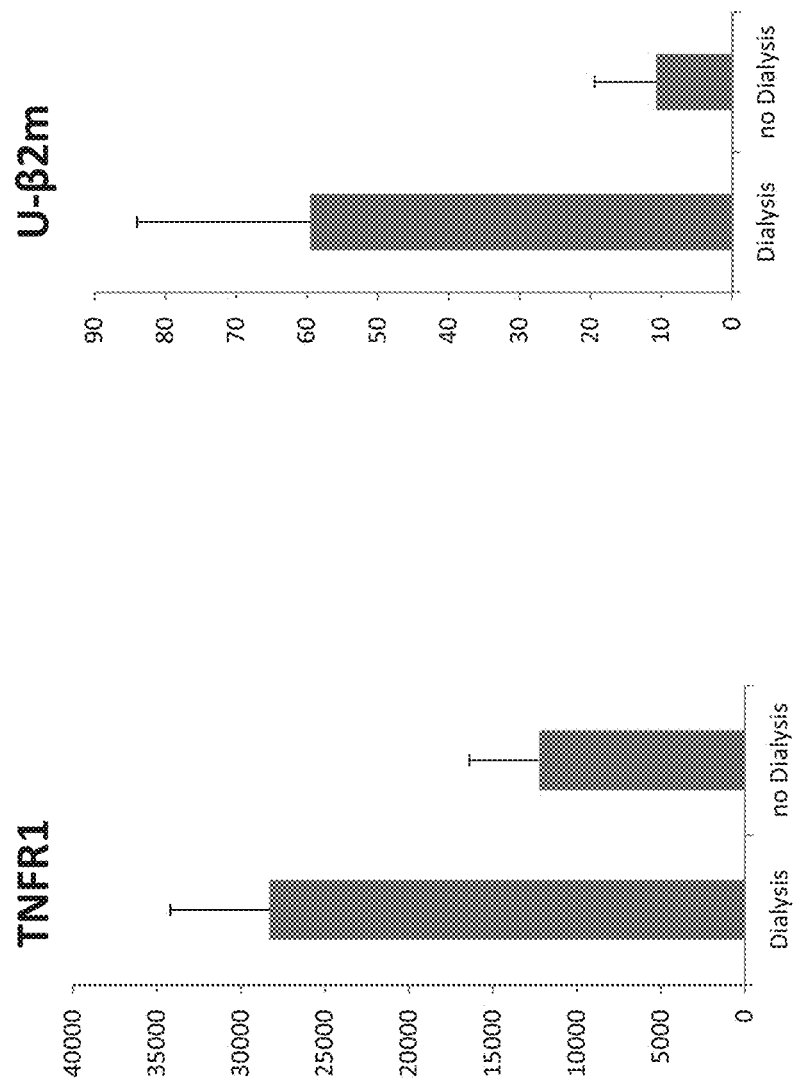

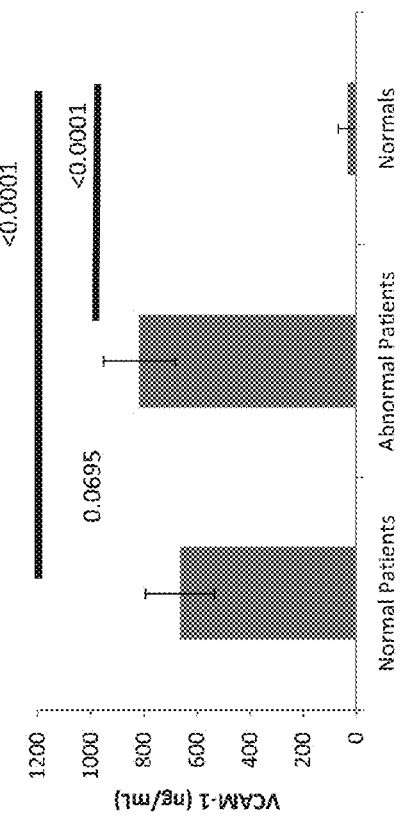
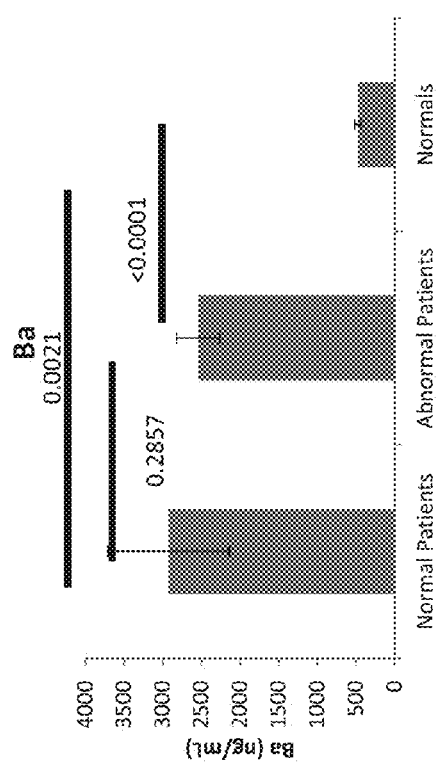
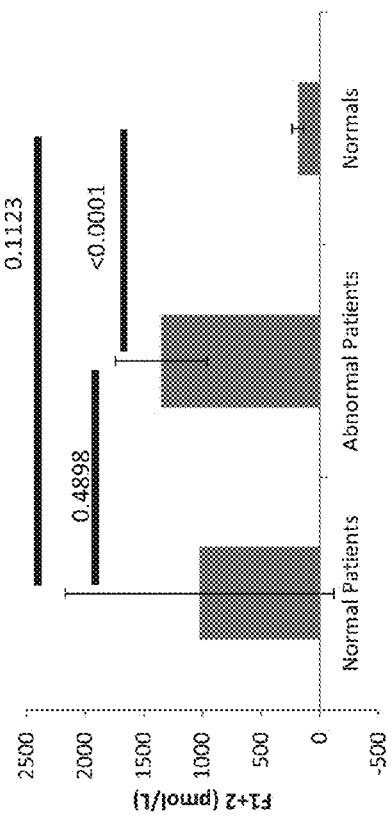
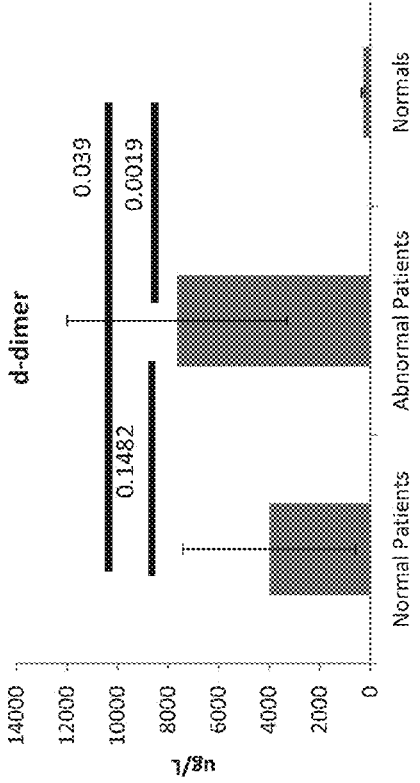

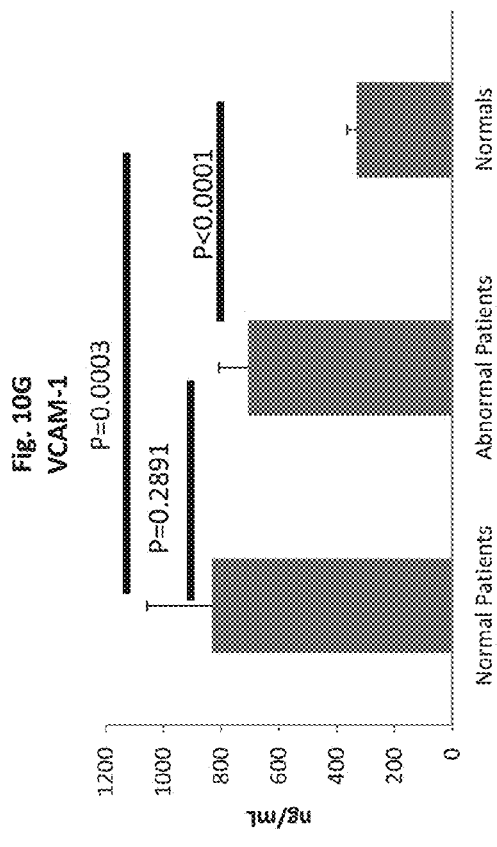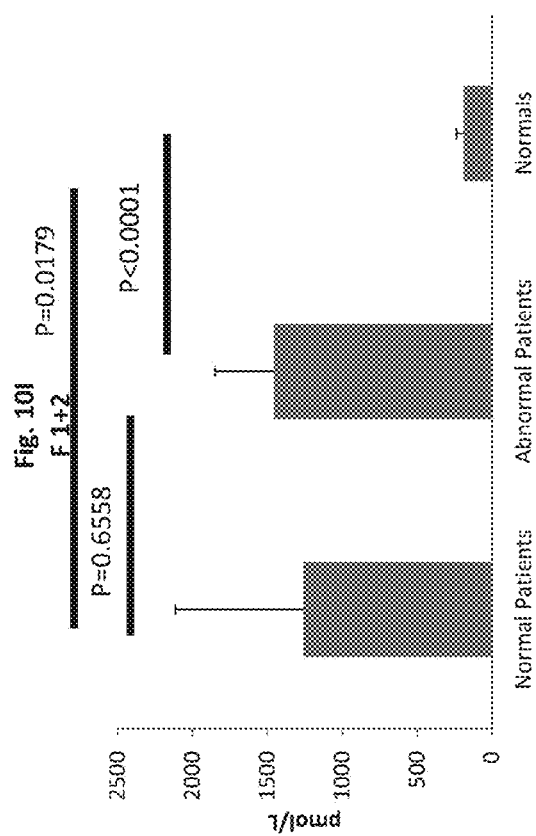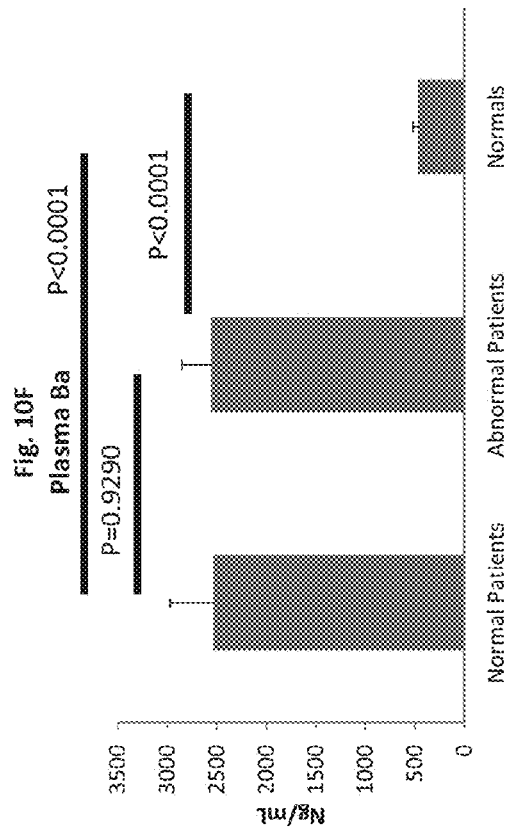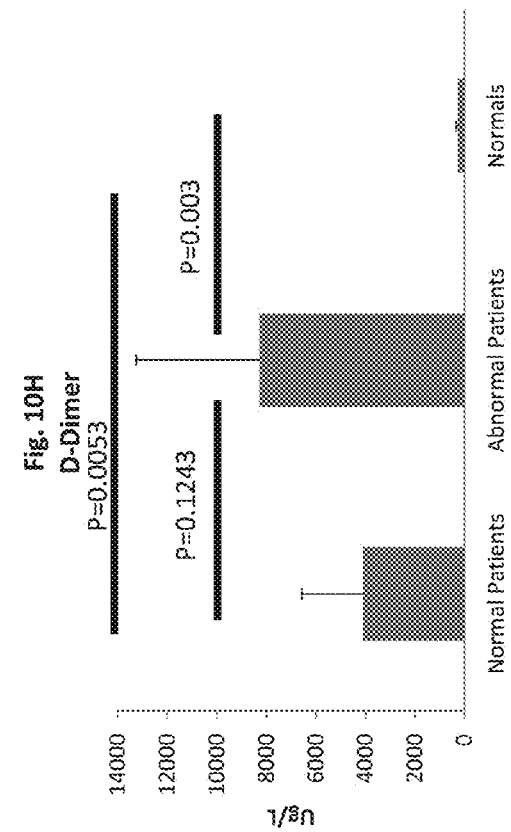

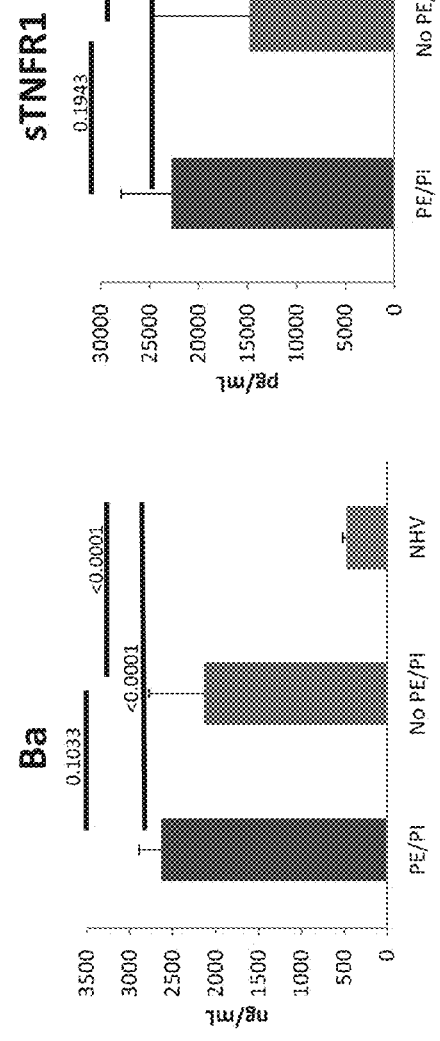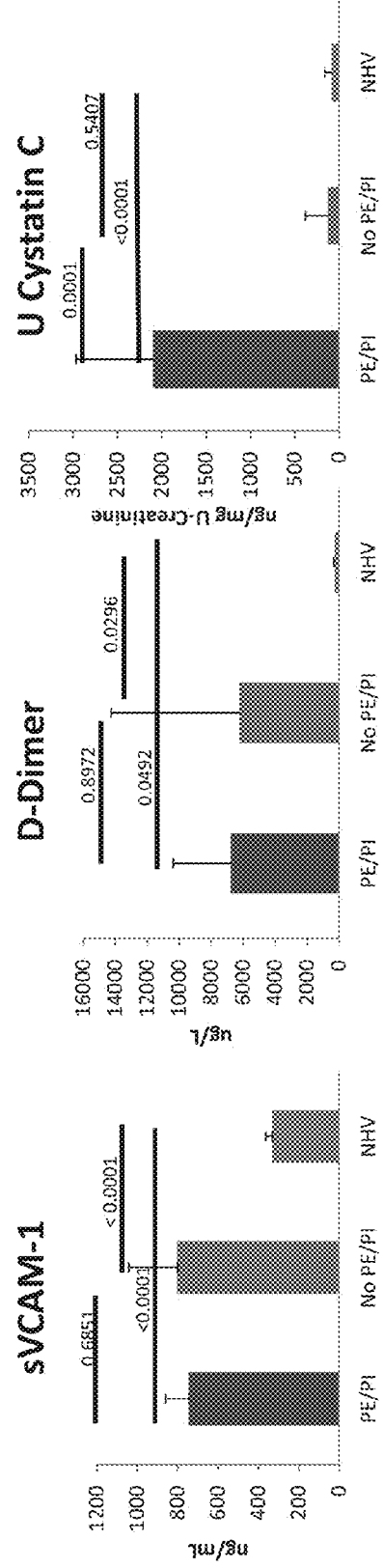
Fig. 17A, Fig. 17B, Fig. 17C, Fig. 17D, Fig. 17E

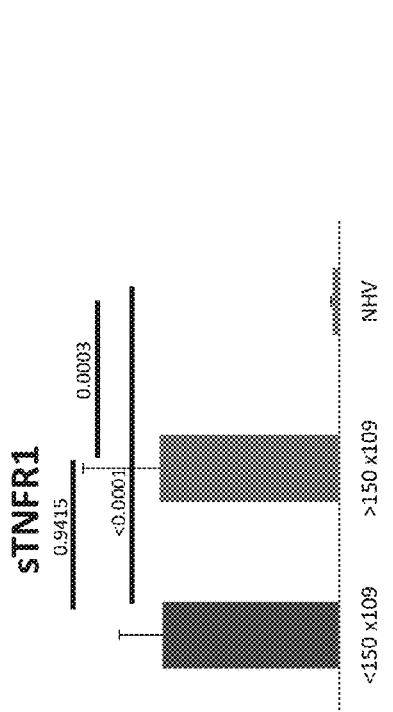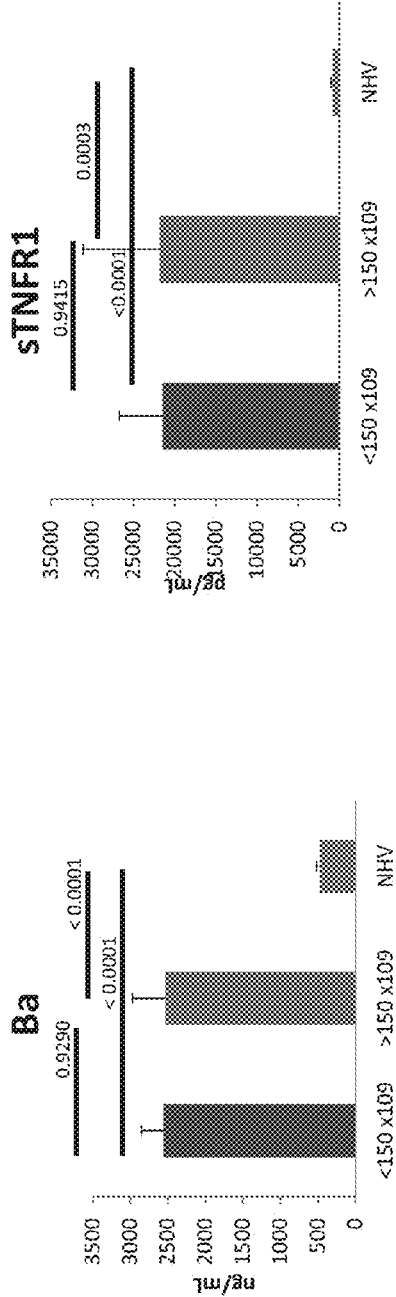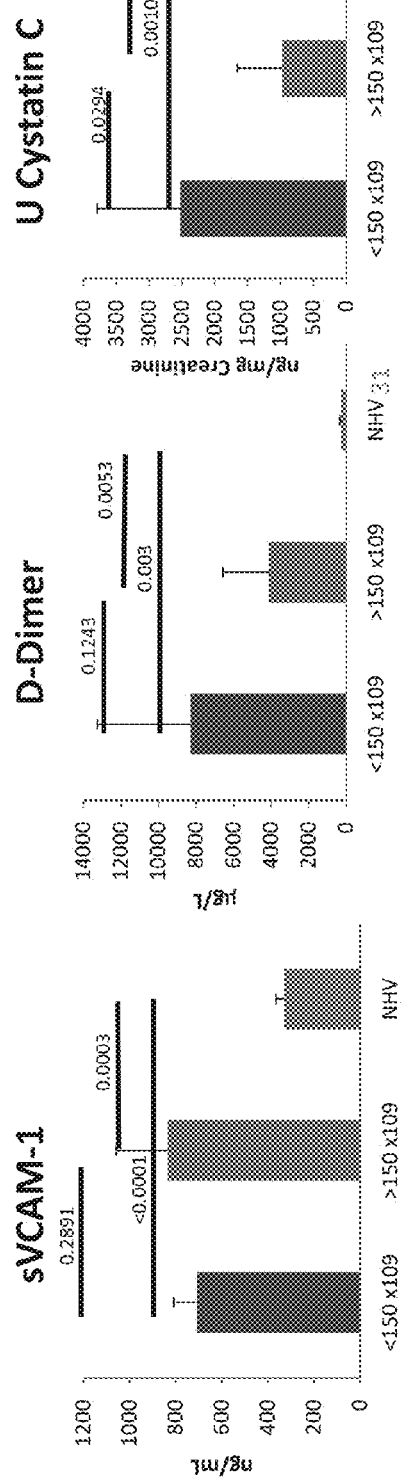
Fig. 18A Ba
Fig. 18B sTNFR1
Fig. 18C sVCAM-1
Fig. 18D D-Dimer
Fig. 18E U Cystatin C

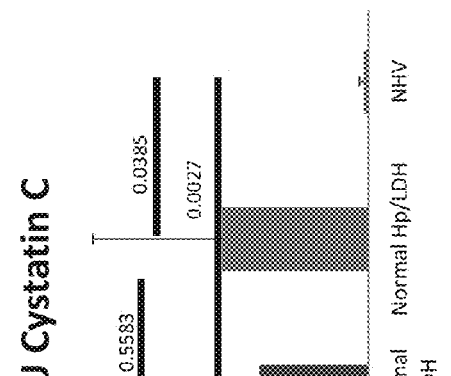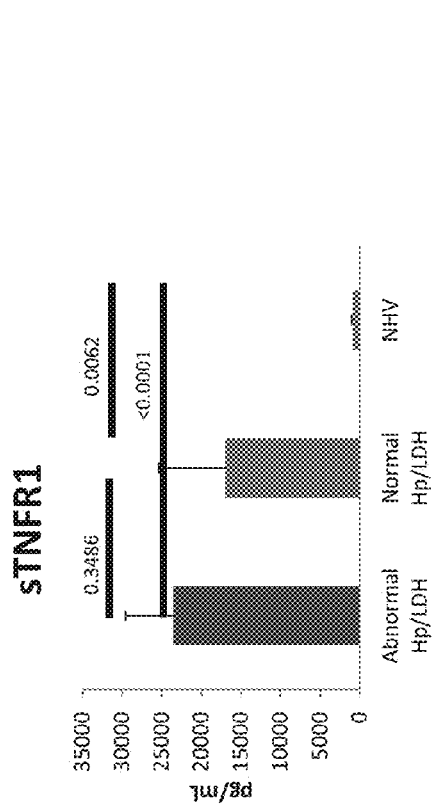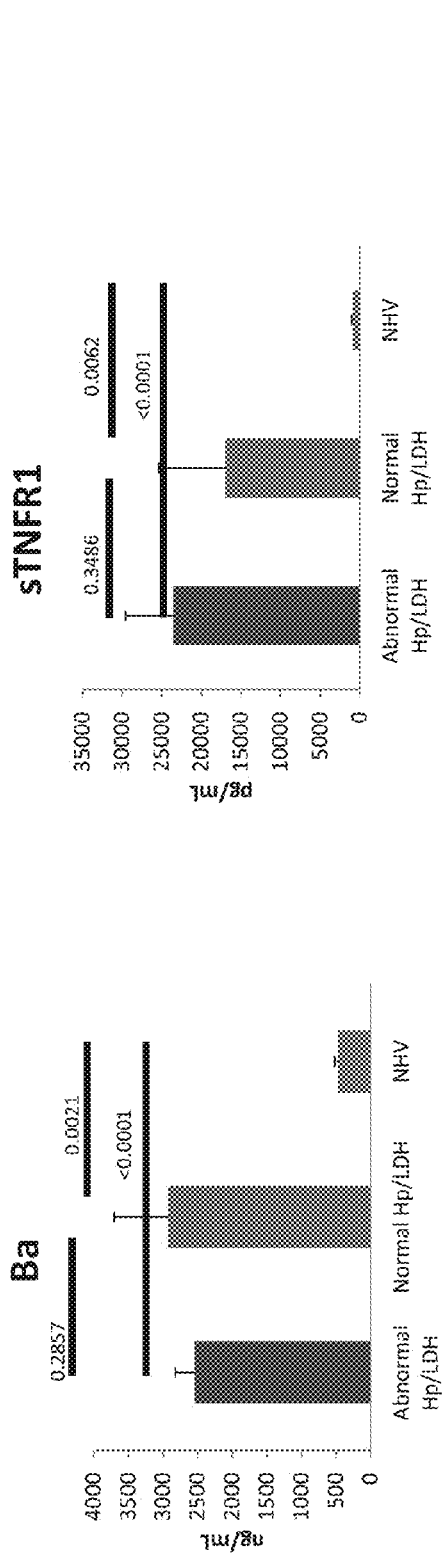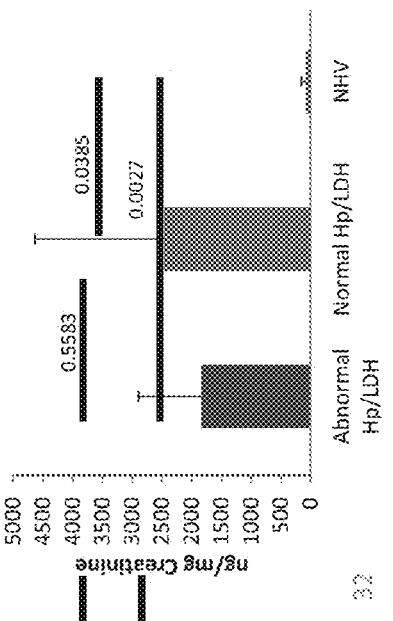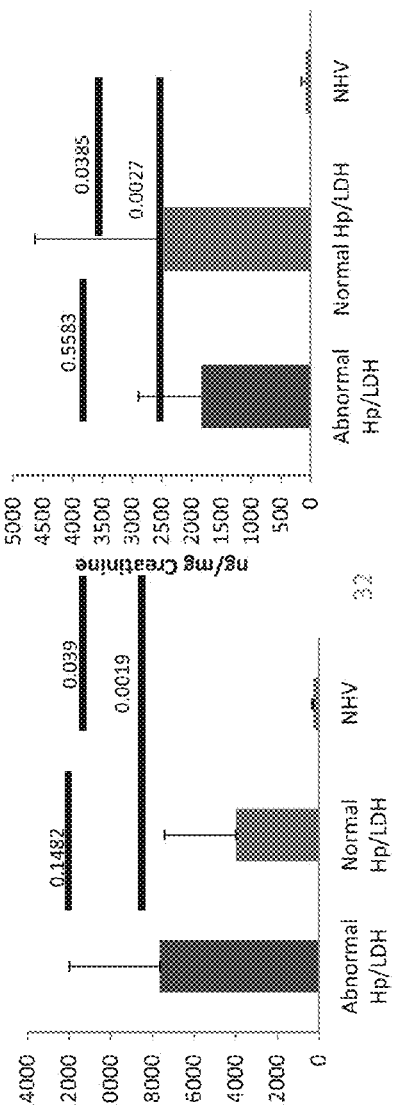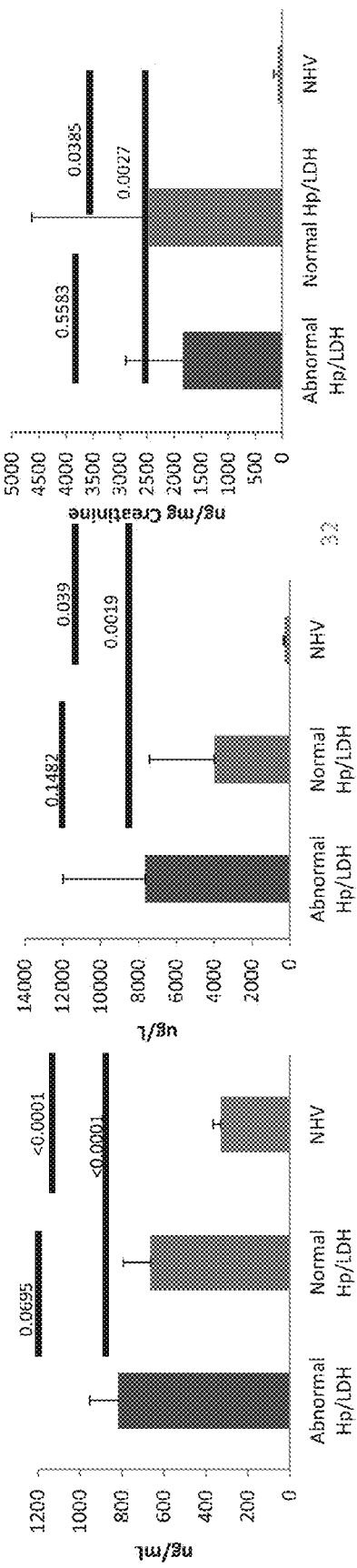

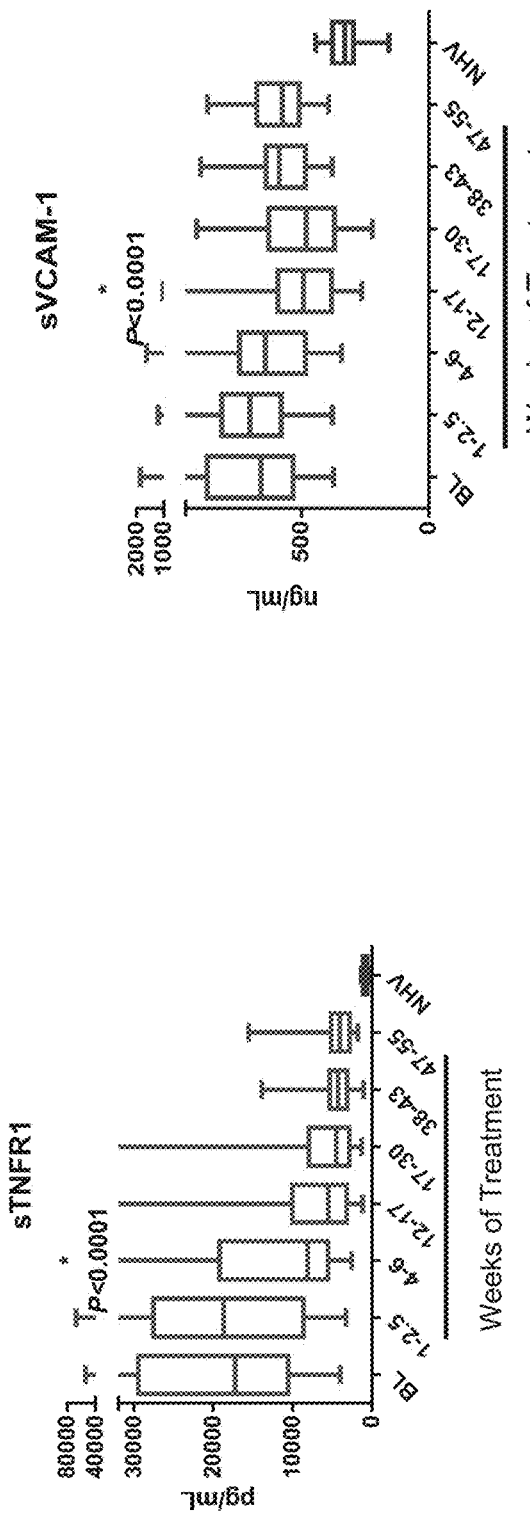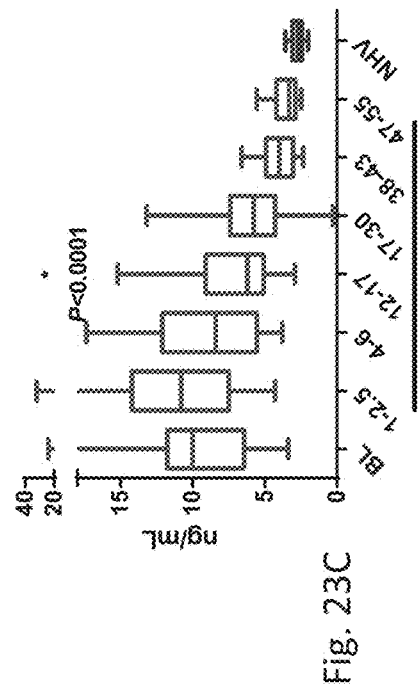
Fig. 23A
Fig. 23B
Fig. 23C

SEQUENCE LISTING

```
<160> NUMBER OF SEQ ID NOS: 6

<210> SEQ ID NO 1
<211> LENGTH: 244
<212> TYPE: PRT
<213> ORGANISM: Homo sapiens
<220> FEATURE:
<221> NAME/KEY: misc_feature
<222> LOCATION: (1)..(244)
<223> OTHER INFORMATION: Human Factor B fragment Ba

<400> SEQUENCE: 1

Leu Gly Leu Leu Ser Gly Gly Val Thr Thr Thr Pro Trp Ser Leu Ala
1               5                   10                  15

Arg Pro Gln Gly Ser Cys Ser Leu Glu Gly Val Glu Ile Lys Gly Gly
            20                  25                  30

Ser Phe Arg Leu Leu Gln Glu Gly Gln Ala Leu Glu Tyr Val Cys Pro
        35                  40                  45

Ser Gly Phe Tyr Pro Tyr Pro Val Gln Thr Arg Thr Cys Arg Ser Thr
    50                  55                  60

Gly Ser Trp Ser Thr Leu Lys Thr Gln Asp Gln Lys Thr Val Arg Lys
65                  70                  75                  80

Ala Glu Cys Arg Ala Ile His Cys Pro Arg Pro His Asp Phe Glu Asn
                85                  90                  95

Gly Glu Tyr Trp Pro Arg Ser Pro Tyr Tyr Asn Val Ser Asp Glu Ile
            100                 105                 110

Ser Phe His Cys Tyr Asp Gly Tyr Thr Leu Arg Gly Ser Ala Asn Arg
        115                 120                 125

Thr Cys Gln Val Asn Gly Arg Trp Ser Gly Gln Thr Ala Ile Cys Asp
    130                 135                 140

Asn Gly Ala Gly Tyr Cys Ser Asn Pro Gly Ile Pro Ile Gly Thr Arg
145                 150                 155                 160

Lys Val Gly Ser Gln Tyr Arg Leu Glu Asp Ser Val Thr Tyr His Cys
```

```
                    165                 170                 175
Ser Arg Gly Leu Thr Leu Arg Gly Ser Gln Arg Thr Cys Gln Glu
                180                 185                 190

Gly Gly Ser Trp Ser Gly Thr Glu Pro Ser Cys Gln Asp Ser Phe Met
            195                 200                 205

Tyr Asp Thr Pro Gln Glu Val Ala Glu Ala Phe Leu Ser Ser Leu Thr
        210                 215                 220

Glu Thr Ile Glu Gly Val Asp Ala Glu Asp Gly His Gly Pro Gly Glu
225                 230                 235                 240

Gln Gln Lys Arg

<210> SEQ ID NO 2
<211> LENGTH: 77
<212> TYPE: PRT
<213> ORGANISM: Homo sapiens
<220> FEATURE:
<221> NAME/KEY: misc_feature
<222> LOCATION: (1)..(77)
<223> OTHER INFORMATION: Human Complement Component C3a

<400> SEQUENCE: 2

Ser Val Gln Leu Thr Glu Lys Arg Met Asp Lys Val Gly Lys Tyr Pro
1               5                   10                  15

Lys Glu Leu Arg Lys Cys Cys Glu Asp Gly Met Arg Glu Asn Pro Met
            20                  25                  30

Arg Phe Ser Cys Gln Arg Arg Thr Arg Phe Ile Ser Leu Gly Glu Ala
        35                  40                  45

Cys Lys Lys Val Phe Leu Asp Cys Cys Asn Tyr Ile Thr Glu Leu Arg
    50                  55                  60

Arg Gln His Ala Arg Ala Ser His Leu Gly Leu Ala Arg
65                  70                  75

<210> SEQ ID NO 3
<211> LENGTH: 74
<212> TYPE: PRT
<213> ORGANISM: Homo sapiens
<220> FEATURE:
<221> NAME/KEY: misc_feature
<222> LOCATION: (1)..(74)
<223> OTHER INFORMATION: Human Complement Component C5a

<400> SEQUENCE: 3

Thr Leu Gln Lys Lys Ile Glu Glu Ile Ala Ala Lys Tyr Lys His Ser
1               5                   10                  15

Val Val Lys Lys Cys Cys Tyr Asp Gly Ala Cys Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser His Lys Asp Met Gln Leu Gly Arg
65                  70

<210> SEQ ID NO 4
<211> LENGTH: 155
<212> TYPE: PRT
<213> ORGANISM: Homo sapiens
<220> FEATURE:
<221> NAME/KEY: misc_feature
<222> LOCATION: (1)..(155)
<223> OTHER INFORMATION: Human Prothrombin Activation Fragment 1
```

```
<400> SEQUENCE: 4

Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
            20                  25                  30

Ser Ser Thr Ala Thr Asp Val Phe Trp Ala Lys Tyr Thr Ala Cys Glu
        35                  40                  45

Thr Ala Arg Thr Pro Arg Asp Lys Leu Ala Ala Cys Leu Glu Gly Asn
    50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
            100                 105                 110

Phe Cys Arg Asn Pro Asp Ser Ser Thr Thr Gly Pro Trp Cys Tyr Thr
        115                 120                 125

Thr Asp Pro Thr Val Arg Arg Gln Glu Cys Ser Ile Pro Val Cys Gly
    130                 135                 140

Gln Asp Gln Val Thr Val Ala Met Thr Pro Arg
145                 150                 155

<210> SEQ ID NO 5
<211> LENGTH: 129
<212> TYPE: PRT
<213> ORGANISM: Homo sapiens
<220> FEATURE:
<221> NAME/KEY: misc_feature
<222> LOCATION: (1)..(129)
<223> OTHER INFORMATION: Human Prothrombin Activation Fragment 2

<400> SEQUENCE: 5

Ser Glu Gly Ser Ser Val Asn Leu Ser Pro Leu Glu Gln Cys Val
1               5                   10                  15

Pro Asp Arg Gly Gln Gln Tyr Gln Gly Arg Leu Ala Val Thr Thr His
            20                  25                  30

Gly Leu Pro Cys Leu Ala Trp Ala Ser Ala Gln Ala Lys Ala Leu Ser
        35                  40                  45

Lys His Gln Asp Phe Asn Ser Ala Val Gln Leu Val Glu Asn Phe Cys
    50                  55                  60

Arg Asn Pro Asp Gly Asp Glu Glu Gly Val Trp Cys Tyr Val Ala Gly
65                  70                  75                  80

Lys Pro Gly Asp Phe Gly Tyr Cys Asp Leu Asn Tyr Cys Glu Glu Ala
                85                  90                  95

Val Glu Glu Glu Thr Gly Asp Gly Leu Asp Glu Asp Ser Asp Arg Ala
            100                 105                 110

Ile Glu Gly Arg Thr Ala Thr Ser Glu Tyr Gln Thr Phe Phe Asn Pro
        115                 120                 125

Arg

<210> SEQ ID NO 6
<211> LENGTH: 622
<212> TYPE: PRT
<213> ORGANISM: Homo sapiens
<220> FEATURE:
<221> NAME/KEY: misc_feature
<222> LOCATION: (1)..(622)
```

<223> OTHER INFORMATION: Human Prothrombin

<400> SEQUENCE: 6

```
Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Ala Asn Thr Phe Leu
        35                  40                  45

Glu Glu Val Arg Lys Gly Asn Leu Glu Arg Glu Cys Val Glu Glu Thr
    50                  55                  60

Cys Ser Tyr Glu Glu Ala Phe Glu Ala Leu Glu Ser Ser Thr Ala Thr
65                  70                  75                  80

Asp Val Phe Trp Ala Lys Tyr Thr Ala Cys Glu Thr Ala Arg Thr Pro
                85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
        115                 120                 125

Cys Gln Leu Trp Arg Ser Arg Tyr Pro His Lys Pro Glu Ile Asn Ser
    130                 135                 140

Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
                165                 170                 175

Arg Arg Gln Glu Cys Ser Ile Pro Val Cys Gly Gln Asp Gln Val Thr
            180                 185                 190

Val Ala Met Thr Pro Arg Ser Glu Gly Ser Ser Val Asn Leu Ser Pro
        195                 200                 205

Pro Leu Glu Gln Cys Val Pro Asp Arg Gly Gln Gln Tyr Gln Gly Arg
    210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
                245                 250                 255

Leu Val Glu Asn Phe Cys Arg Asn Pro Asp Gly Asp Glu Glu Gly Val
            260                 265                 270

Trp Cys Tyr Val Ala Gly Lys Pro Gly Asp Phe Gly Tyr Cys Asp Leu
        275                 280                 285

Asn Tyr Cys Glu Glu Ala Val Glu Glu Thr Gly Asp Gly Leu Asp
    290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
                325                 330                 335

Gly Leu Arg Pro Leu Phe Glu Lys Lys Ser Leu Glu Asp Lys Thr Glu
            340                 345                 350

Arg Glu Leu Leu Glu Ser Tyr Ile Asp Gly Arg Ile Val Glu Gly Ser
        355                 360                 365

Asp Ala Glu Ile Gly Met Ser Pro Trp Gln Val Met Leu Phe Arg Lys
    370                 375                 380

Ser Pro Gln Glu Leu Leu Cys Gly Ala Ser Leu Ile Ser Asp Arg Trp
385                 390                 395                 400
```

-continued

```
Val Leu Thr Ala Ala His Cys Leu Leu Tyr Pro Pro Trp Asp Lys Asn
            405                 410                 415

Phe Thr Glu Asn Asp Leu Leu Val Arg Ile Gly Lys His Ser Arg Thr
            420                 425                 430

Arg Tyr Glu Arg Asn Ile Glu Lys Ile Ser Met Leu Glu Lys Ile Tyr
        435                 440                 445

Ile His Pro Arg Tyr Asn Trp Arg Glu Asn Leu Asp Arg Asp Ile Ala
    450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
            485                 490                 495

Tyr Lys Gly Arg Val Thr Gly Trp Gly Asn Leu Lys Glu Thr Trp Thr
            500                 505                 510

Ala Asn Val Gly Lys Gly Gln Pro Ser Val Leu Gln Val Val Asn Leu
            515                 520                 525

Pro Ile Val Glu Arg Pro Val Cys Lys Asp Ser Thr Arg Ile Arg Ile
    530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
            565                 570                 575

Pro Phe Asn Asn Arg Trp Tyr Gln Met Gly Ile Val Ser Trp Gly Glu
            580                 585                 590

Gly Cys Asp Arg Asp Gly Lys Tyr Gly Phe Tyr Thr His Val Phe Arg
            595                 600                 605

Leu Lys Lys Trp Ile Gln Lys Val Ile Asp Gln Phe Gly Glu
    610                 615                 620
```

ATYPICAL HEMOLYTIC UREMIC SYNDROME (AHUS) BIOMARKER PROTEINS

CROSS-REFERENCE TO RELATED APPLICATIONS

This application is a continuation of U.S. patent application Ser. No. 14/453,268, filed Aug. 6, 2014, which claims priority to U.S. Provisional Application Nos. 61/913,180 and 61/863,299, filed Dec. 6, 2013 and Aug. 7, 2013, respectively. The entire contents of the aforementioned application and any patents, patent applications, and references cited throughout this specification are herein incorporated by reference in their entireties.

SEQUENCE LISTING

The instant application contains a Sequence Listing which has been submitted electronically in ASCII format and is hereby incorporated by reference in its entirety. Said ASCII copy, created on Jan. 29, 2016, is named AXJ_176CN_Sequence.txt and is 12,514 bytes in size.

TECHNICAL FIELD

The field of the invention is medicine, immunology, molecular biology, and protein chemistry.

BACKGROUND

Hemolytic uremic syndrome (HUS) is characterized by thrombocytopenia, microangiopathic hemolytic anemia, and acute renal failure. HUS is classified as one of two types: diarrheal-associated (D+ HUS; also referred to as shiga toxin producing *E. coli* (STEC)-HUS or typical HUS) and non-diarrheal or atypical HUS (aHUS). D+ HUS is the most common form, accounting for greater than 90% of cases and is caused by a preceding illness with a shiga-like toxin-producing bacterium, e.g., *E. coli* O157:H7. aHUS is rare and has a mortality rate of up to 25%. Many patients with this disease will sustain permanent neurological or renal impairment, e.g., at least 50% of aHUS patients progress to end-stage renal failure (ESRF). See, e.g., Kavanagh et al. (2006) *British Medical Bulletin* 77 and 78:5-22.

aHUS can be genetic, acquired, or idiopathic. Hereditable forms of aHUS can be associated with mutations in a number of human complement components including, e.g., complement factor H (CFH), membrane cofactor protein (MCP), complement factor I (CFI), C4b-binding protein (C4BP), complement factor B (CFB), and complement component 3 (C3). See, e.g., Caprioli et al. (2006) *Blood* 108:1267-1279. Certain mutations in the gene encoding CD55, though not yet implicated in aHUS, are associated with the severity of aHUS. See, e.g., Esparza-Gordillo et al. (2005) *Hum Mol Genet* 14:703-712.

Until recently, treatment options for patients with aHUS were limited and often involved plasma infusion or plasma exchange. In some cases, aHUS patients undergo uni- or bilateral nephrectomy or renal transplantation (see Artz et al. (2003) *Transplantation* 76:821-826). However, recurrence of the disease in treated patients is common. Recently, treatment of aHUS patients with the drug Soliris® was approved in the United States of America and in Europe. Despite finally having a useful drug for treatment of aHUS patients, there is still a need to diagnose patients with aHUS, as well as monitor the progression and abatement of aHUS.

SUMMARY

The present disclosure provides, among other things, a variety of proteins whose activity and/or concentration in a biological fluid is abnormal in patients afflicted with aHUS and/or those aHUS patients receiving complement inhibitor therapy. Hereinafter these proteins are referred to as "aHUS-associated biomarker proteins" or "aHUS biomarker proteins". For example, the inventors have observed that the concentrations and/or activities of several proteins in the blood (e.g., serum and/or plasma) and urine are abnormal in patients with aHUS. The inventors have also observed that, following administration of an antagonist anti-C5 antibody (eculizumab) to a human, the concentrations of a subset of these proteins change. In some instances, the concentration of one or more of the proteins is normalized. While the disclosure is not bound by any particular theory or mechanism of action, the inventors believe that monitoring a patient treated with a complement inhibitor (such as an anti-C5 antibody) for a change in concentration of one or more of these proteins—aHUS biomarker proteins—is useful for, e.g., diagnosing a patient as having or at risk of developing aHUS. Monitoring the status of one or more of these biomarker proteins can also be useful for determining whether an aHUS patient is responding to therapy with a complement inhibitor. Moreover, evaluating the status of one or more of the biomarkers is also useful for identifying a dose—a threshold dose—of a complement inhibitor, such as an anti-C5 antibody, that by virtue of its effect on the concentration of one or more of the aHUS biomarker proteins in the human is sufficient to achieve a clinically-meaningful effect on the disease (i.e., sufficient to treat a complement-associated disease such as aHUS).

Accordingly, in one aspect, the disclosure features a method for monitoring or evaluating the status of atypical hemolytic uremic syndrome (aHUS)-associated biomarker proteins in a subject (e.g., a mammal such as a human) or a method for assessing one or both of the concentration and activity level of at least one atypical hemolytic uremic syndrome (aHUS)-associated biomarker protein in a subject. The method comprises measuring in a biological fluid obtained from the subject one or both of (i) the concentration of at least one (e.g., at least two, three, four, five, six, seven, eight, nine, 10, 11, 12, 13, 14, 15, 16, 17, 18, 19, 20) aHUS-associated biomarker proteins in the biological fluid, wherein the aHUS-associated biomarker proteins are any of the biomarkers set forth in Table 1, e.g., one selected from the group consisting of: a proteolytic fragment of complement component factor B (e.g., Ba or Bb), soluble C5b9 (sC5b9), thrombomodulin, VCAM-1, von Willebrand Factor (vWF), soluble CD40 ligand (sCD40L), prothrombin fragment F1+2, D-dimer, CXCL10, MCP-1, TNFR1, IFN-γ, ICAM-1, IL-1 beta, IL-12 p70, complement component C5a, β2 microglobulin (β2M), clusterin, cystatin C, NAG, TIMP-1, NGAL, fatty acid binding protein 1 (FABP-1), CXCL9, KIM-1, IL-18, vascular endothelial cell growth factor (VEGF), IL-6, albumin, IL-8, and CCL5. The subject can be, e.g., a human having, suspected of having, or at risk for developing, aHUS. The subject can be one who has been (or is being) treated with an inhibitor of complement (e.g., an inhibitor of complement component C5 such as an anti-C5 antibody). The treatment can have occurred less than one month (e.g., less than 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 day) prior to obtaining the sample from the subject. The method can further include the step of determining whether the subject has or is at risk of developing aHUS. Where the subject has been treated or is being treated with a complement inhibitor (e.g., an anti-C5 antibody) under a predetermined dosing schedule, the method can further include determining whether the patient is responsive (therapeutically) to the complement inhibitor therapy.

In another aspect, the disclosure features a method for monitoring or evaluating the status of atypical hemolytic uremic syndrome (aHUS)-associated biomarker proteins in a subject (e.g., a mammal such as a human) or a method for assessing one or both of the concentration and activity level of at least one atypical hemolytic uremic syndrome (aHUS)-associated biomarker protein in a subject. The method comprises: (A) measuring in a biological fluid obtained from the subject the concentration of at least one (e.g., at least two, three, four, five, six, seven, eight, nine, 10, 11, 12, 13, 14, 15, 16, 17, 18, 19, 20) aHUS-associated biomarker proteins in the biological fluid, wherein the aHUS-associated biomarker proteins are any of the biomarkers set forth in Table 1, e.g., one selected from the group consisting of: a proteolytic fragment of complement component factor B (e.g., Ba or Bb), soluble C5b9 (sC5b9), thrombomodulin, VCAM-1, von Willebrand Factor (vWF), soluble CD40 ligand (sCD40L), prothrombin fragment F1+2, D-dimer, CXCL10, MCP-1, TNFR1, IFN-γ, ICAM-1, IL-1 beta, IL-12 p70, complement component C5a, β2 microglobulin (β2M), clusterin, cystatin C, NAG, TIMP-1, NGAL, fatty acid binding protein 1 (FABP-1), CXCL9, KIM-1, IL-18, vascular endothelial cell growth factor (VEGF), IL-6, albumin, IL-8, and CCL5; and (B) recording (e.g., in an electronic patient record) the results of the measurement(s) or communicating the results of the measurement(s) to the subject, the subject's guardian, or a medical professional in whose care the subject has been placed. The subject can be, e.g., a human having, suspected of having, or at risk for developing, aHUS. The subject can be one who has been (or is being) treated with an inhibitor of complement (e.g., an inhibitor of complement component C5 such as an anti-C5 antibody). The treatment can have occurred less than one month (e.g., less than 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 day) prior to obtaining the sample from the subject. The method can further include the step of determining whether the subject has or is at risk of developing aHUS. Where the subject has been treated or is being treated with a complement inhibitor (e.g., an anti-C5 antibody) under a predetermined dosing schedule, the method can further include determining whether the patient is responsive (therapeutically) to the complement inhibitor therapy.

In yet another aspect, the disclosure features a method for monitoring or determining whether a patient is at risk for developing thrombotic microangiopathy. The method includes (A) measuring in a biological fluid obtained from the subject the concentration of at least one (e.g., at least two, three, four) biomarker protein associated with thrombosis or coagulation in the biological fluid, wherein the biomarker proteins are any of such biomarkers set forth in Table 1 or Table 11, e.g., F1+2 or D-dimer; and (B) recording (e.g., in an electronic patient record) the results of the measurement(s) or communicating the results of the measurement(s) to the subject, the subject's guardian, or a medical professional in whose care the subject has been placed. The subject can be, e.g., a human having, suspected of having, or at risk for developing, aHUS. The subject can be one who has been (or is being) treated with an inhibitor of complement (e.g., an inhibitor of complement component C5 such as an anti-C5 antibody). The treatment can have occurred less than one month (e.g., less than 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 day) prior to obtaining the sample from the subject. The method can further include the step of determining whether the subject has or is at risk of developing aHUS (or confirming a diagnosis of aHUS) using any of the methods described herein. Where the subject has been treated or is being treated with a complement inhibitor (e.g., an anti-C5 antibody) under a predetermined dosing schedule, the method can further include determining whether the patient is responsive (therapeutically) to the complement inhibitor therapy, i.e., a reduction in the concentration of one or more of the thrombosis or coagulation-associated biomarkers occurs following treatment with the complement inhibitor.

In another aspect, the disclosure features a method for monitoring or evaluating the status of atypical hemolytic uremic syndrome (aHUS)-associated biomarker proteins in a subject (e.g., a mammal such as a human) or a method for assessing one or both of the concentration and activity level of at least one atypical hemolytic uremic syndrome (aHUS)-associated biomarker protein in a subject. The method comprises: (A) measuring in a biological fluid obtained from the subject the concentration of at least one (e.g., at least two, three, four, five, six, seven, eight, nine, 10, 11, 12, or 13) aHUS-associated biomarker proteins in the biological fluid, wherein the aHUS-associated biomarker proteins are any of the biomarkers set forth in Table 1, e.g., one selected from the group consisting of: a proteolytic fragment of complement component factor B (e.g., Ba or Bb), soluble C5b9 (sC5b9), C5a, thrombomodulin, VCAM-1, prothrombin fragment F1+2, D-dimer, sTNFR1, β2 microglobulin (β2M), clusterin, cystatin C, TIMP-1, and fatty acid binding protein 1 (FABP-1); and (B) recording (e.g., in an electronic patient record) the results of the measurement(s) or communicating the results of the measurement(s) to the subject, the subject's guardian, or a medical professional in whose care the subject has been placed. The subject can be, e.g., a human having, suspected of having, or at risk for developing, aHUS. The subject can be one who has been (or is being) treated with an inhibitor of complement (e.g., an inhibitor of complement component C5 such as an anti-C5 antibody). The treatment can have occurred less than one month (e.g., less than 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 day) prior to obtaining the sample from the subject. The method can further include the step of determining whether the subject has or is at risk of developing aHUS. Where the subject has been treated or is being treated with a complement inhibitor (e.g., an anti-C5 antibody) under a predetermined dosing schedule, the method can further include determining whether the patient is responsive (therapeutically) to the complement inhibitor therapy.

In some embodiments, any of the methods described herein can further comprise determining whether the subject has or is at risk for developing aHUS. In some embodiments, an elevated concentration, as compared to the concentration in a normal control biological fluid of the same type, of at least one of Ba, sC5b-9, C5a, sCD40L, prothrombin fragment F1+2, D-dimer, thrombomodulin, VCAM-1, vWF, FABP-1, β2M, clusterin, cystatin C, TIMP-1, albumin, NGAL, CXCL10, CXCL9, IL-18, TNFR1, VCAM-1, MCP-1, VEGF, CCL5, IL-6, IFNγ, indicates that the subject has, or is at risk for developing, aHUS.

In some embodiments, any of the methods described herein include determining whether the subject has responded to treatment with the complement inhibitor. In some embodiments, (a) a reduced concentration, as compared to the concentration in a sample of biological fluid of the same type obtained from the subject prior to treatment with the inhibitor, of at least one of CXCL10, MCP-1, TNFR1, IFN-γ, a proteolytic fragment of complement component factor B (e.g., Ba or Bb), soluble C5b9 (sC5b9), prothrombin fragment F1+2, d-dimer, thrombomodulin, VCAM-1, von Willebrand Factor (vWF), complement component C5a, sC5b9, β2 microglobulin (β2M), clusterin, cystatin C, NAG, TIMP-1, NGAL, fatty acid binding protein 1 (FABP-1), albumin, CXCL10, CXCL9, and KIM-1; or (b) an increased concentration, as compared to the concentration in a sample of biological fluid of the same type obtained from the subject prior to treatment with the inhibitor, of CCL5, indicates that the subject is responsive to treatment with the inhibitor.

In another aspect, the disclosure features a method for monitoring responsiveness of a subject (e.g., a mammal such as a human) to treatment with an inhibitor of complement component C5. The method includes: measuring the concentration of at least two aHUS-associated biomarker proteins in a biological fluid, wherein the aHUS-associated biomarker proteins are any of those set forth in Table 1, e.g., one selected from the group consisting of: a proteolytic fragment of complement component factor B (e.g., Ba or Bb), soluble C5b9 (sC5b9), thrombomodulin, VCAM-1, von Willebrand Factor (vWF), soluble CD40 ligand (sCD40L), prothrombin fragment F1+2, D-dimer, CXCL10, MCP-1, TNFR1, IFN-γ, ICAM-1, IL-1 beta, IL-12 p70, complement component C5a, β2 microglobulin (β2M), clusterin, cystatin C, NAG, TIMP-1, NGAL, fatty acid binding protein 1 (FABP-1), CXCL9, KIM-1, IL-18, vascular endothelial cell growth factor (VEGF), IL-6, albumin, IL-8, and CCL5. The biological fluid is obtained from a subject: (i) having, suspected of having, or at risk for developing, aHUS and (ii) who is being (or who has been, e.g., recently) treated with an inhibitor of complement component C5 under a predetermined dosing schedule. In accordance with such methods, (a) a reduced concentration, as compared to the concentration in a sample of biological fluid of the same type obtained from the subject prior to treatment with the inhibitor, of at least one of CXCL10, MCP-1, TNFR1, IFN-γ, a proteolytic fragment of complement component factor B (e.g., Ba or Bb), soluble C5b9 (sC5b9), prothrombin fragment F1+2, d-dimer, thrombomodulin, VCAM-1, von Willebrand Factor (vWF), complement component C5a, β2 microglobulin (β2M), clusterin, cystatin C, NAG, TIMP-1, NGAL, fatty acid binding protein 1 (FABP-1), albumin, CXCL10, CXCL9, and KIM-1; or (b) an increased concentration, as compared to the concentration in a sample of biological fluid of the same type obtained from the subject prior to treatment with the inhibitor, of CCL5, indicates that the subject is responsive to treatment with the inhibitor.

In some embodiments, any of the methods described herein include determining whether the subject has responded to treatment with the complement inhibitor. In some embodiments, a reduced concentration, as compared to the concentration in a sample of biological fluid of the same type obtained from the subject prior to treatment with the inhibitor, of at least one of a proteolytic fragment of complement component factor B (e.g., Ba or Bb), soluble C5b9 (sC5b9), C5a, thrombomodulin, VCAM-1, prothrombin fragment F1+2, D-dimer, sTNFR1, β2 microglobulin (β2M), clusterin, cystatin C, TIMP-1, and fatty acid binding protein 1 (FABP-1).

In another aspect, the disclosure features a method for monitoring responsiveness of a subject to treatment with an inhibitor of complement, wherein the method comprises: determining the concentration of at least two aHUS-associated biomarker proteins in a biological fluid obtained from the subject, wherein the aHUS-associated biomarker proteins are selected from the group consisting of: CXCL10, MCP-1, TNFR1, IFN-γ, IL-6, a proteolytic fragment of complement component factor B (e.g., Ba or Bb), soluble C5b9 (sC5b9), prothrombin fragment F1+2, d-dimer, thrombomodulin, VCAM-1, von Willebrand Factor (vWF), complement component C5a, β2 microglobulin (β2M), clusterin, cystatin C, NAG, TIMP-1, NGAL, fatty acid binding protein 1 (FABP-1), albumin, CXCL9, KIM-1, and CCL5. The subject has, is suspected of having, or is at risk for developing aHUS and the subject has been or is being treated with an inhibitor of complement. (A) a reduced concentration, as compared to the concentration in a sample of biological fluid of the same type obtained from the subject prior to treatment with the inhibitor, of at least one of CXCL10, MCP-1, TNFR1, IFN-γ, IL-6, a proteolytic fragment of complement component factor B (e.g., Ba or Bb), soluble C5b9 (sC5b9), prothrombin fragment F1+2, d-dimer, thrombomodulin, VCAM-1, von Willebrand Factor (vWF), complement component C5a, β2 microglobulin (β2M), clusterin, cystatin C, NAG, TIMP-1, NGAL, fatty acid binding protein 1 (FABP-1), albumin, CXCL9, and KIM-1; or (B) an increased concentration, as compared to the concentration in a sample of biological fluid of the same type obtained from the subject prior to treatment with the inhibitor, of CCL5, indicates that the subject is responsive to treatment with the inhibitor.

In yet another aspect, the disclosure features a method for reducing the number, frequency, or occurrence, likelihood of occurrence, or risk of developing, TMA, using a complement inhibitor in a manner sufficient to induce a physiological change in at least two biomarker proteins associated with thrombosis or coagulation. The method includes: (a) determining the concentration of at least two biomarker proteins in a biological fluid obtained from the subject, wherein the biomarker proteins are selected from Table 1 or 11 and relate to thrombosis and/or coagulation (e.g., D-dimer or F1+2); and (b) administering to a subject having, suspected of having, or at risk for developing, TMA an inhibitor of complement in an amount and with a frequency sufficient to cause a physiological change in at least each of two (2) of the biomarker proteins, wherein the physiological change is a reduction in the concentration of the at least two biomarker proteins relative to the concentration of the markers in an equivalent biological sample obtained from the subject prior to treatment with the complement inhibitor. The method can include both measuring the concentration of the biomarkers before and after treatment.

In yet another aspect, the disclosure features a method for determining whether an aHUS patient treated with a complement inhibitor under a predetermined dosing schedule is in need of: (i) treatment with a different complement inhibitor or (ii) treatment with the same complement inhibitor under a different dosing schedule. The method comprises: (A) determining whether the aHUS patient is responsive to treatment with the complement inhibitor under the predetermined dosing schedule, wherein the determining comprises: measuring in a biological fluid obtained from the subject one or both of the concentration and activity of at least two aHUS-associated biomarker proteins in the biological fluid, wherein the aHUS-associated biomarker proteins are selected from the group consisting of: a proteolytic fragment of complement component factor B (e.g., Ba or Bb), soluble C5b9 (sC5b9), thrombomodulin, VCAM-1, von Willebrand Factor (vWF), soluble CD40 ligand (sCD40L), prothrombin fragment F1+2, D-dimer, CXCL10, MCP-1, TNFR1, IFN-γ, ICAM-1, IL-1 beta, IL-12 p70, complement component C5a, P2 microglobulin (β2M), clusterin, cystatin C, NAG, TIMP-1, NGAL, fatty acid binding protein 1 (FABP-1), CXCL9, KIM-1, IL-18, vascular endothelial cell growth factor (VEGF), IL-6, albumin, IL-8, and CCL5, and wherein: (a) a reduced concentration, as compared to the concentration in a sample of biological fluid of the same type obtained from the subject prior to treatment with the inhibitor, of at least one of CXCL10, MCP-1, TNFR1, IFN-γ, a proteolytic fragment of complement component factor B (e.g., Ba or Bb), soluble C5b9 (sC5b9), prothrombin fragment F1+2, d-dimer, thrombomodulin, VCAM-1, von Willebrand Factor (vWF), complement component C5a, sC5b9, P2 microglobulin (β2M), clusterin, cystatin C, NAG, TIMP-1, NGAL, fatty acid binding protein 1 (FABP-1), albumin, CXCL10, CXCL9, and KIM-1; or (b) an increased concentration, as compared to the concentration in a sample of biological fluid of the same type obtained from the subject prior to treatment with the inhibitor, of CCL5, indicates that the subject is responsive to treatment with the inhibitor; and (B) if the patient is not responsive to treatment with the complement inhibitor, administering the patient a different complement inhibitor or the same complement inhibitor at a higher dose or more frequent dosing schedule as compared to the predetermined dosing schedule.

In yet another aspect, the disclosure features a method for determining whether an aHUS patient treated with a complement inhibitor under a predetermined dosing schedule is in need of: (i) treatment with a different complement inhibitor or (ii) treatment with the same complement inhibitor under a different dosing schedule. The method comprises: (A) determining whether the aHUS patient is responsive to treatment with the complement inhibitor under the predetermined dosing schedule, wherein the determining comprises: measuring in a biological fluid obtained from the subject one or both of the concentration and activity of at least two aHUS-associated biomarker proteins in the biological fluid, wherein the aHUS-associated biomarker proteins are selected from the group consisting of: a proteolytic fragment of complement component factor B (e.g., Ba or Bb), soluble C5b9 (sC5b9), C5a, thrombomodulin, VCAM-1, prothrombin fragment F1+2, D-dimer, sTNFR1, β2 microglobulin (β2M), clusterin, cystatin C, TIMP-1, and fatty acid binding protein 1 (FABP-1), and wherein: (a) a reduced concentration, as compared to the concentration in a sample of biological fluid of the same type obtained from the subject prior to treatment with the inhibitor, of at least one of a proteolytic fragment of complement component factor B (e.g., Ba or Bb), soluble C5b9 (sC5b9), C5a, thrombomodulin, VCAM-1, prothrombin fragment F1+2, D-dimer, sTNFR1, β2 microglobulin (β2M), clusterin, cystatin C, TIMP-1, and fatty acid binding protein 1 (FABP-1) indicates that the subject is responsive to treatment with the inhibitor; and (B) if the patient is not responsive to treatment with the complement inhibitor, administering the patient a different complement inhibitor or the same complement inhibitor at a higher dose or more frequent dosing schedule as compared to the predetermined dosing schedule.

The concentration of one or more of the proteins can be measured using, e.g., an immunoassay (e.g., enzyme linked immunosorbent assay (ELISA), a radioimmunoassay (RIA), Western blotting, or dot blotting) or cytometric bead array (CBA; see the working examples). Such methods as well as kits useful for performing the methods are described herein. Suitable methods for measuring the activity of vWF are known in the art and described herein.

In some embodiments of any of the methods described herein, the concentrations of at least five individual aHUS-associated biomarker proteins are measured. In some embodiments of any of the methods described herein, the concentrations of at least ten individual aHUS-associated biomarker proteins are measured. In some embodiments of any of the methods described herein, the concentrations of at least 15 individual aHUS-associated biomarker proteins are measured. In some embodiments of any of the methods described herein, the concentrations of at least 20 individual aHUS-associated biomarker proteins are measured.

In some embodiments of any of the methods described herein, the biological fluid is blood. In some embodiments, the biological fluid is a blood fraction, e.g., serum or plasma. In some embodiments, the biological fluid is urine. In some embodiments of any of the methods described herein, all of the measurements are performed on one biological fluid. In some embodiments of any of the methods described herein, measurements are performed on at least two different biological fluids obtained from the subject. In some embodiments, the concentrations of at least two individual aHUS-associated biomarker proteins are measured and the concentration of the first aHUS-associated biomarker protein is measured in one type of biological fluid and the second aHUS-associated biomarker protein is measured in a second type of biological fluid.

In some embodiments of any of the methods described herein, the concentrations of at least two (e.g., at least three, four, or all) of IFN-γ, ICAM-1, IL-1 beta, and IL-12 p70 are measured. In some embodiments of any of the methods described herein, the concentrations of both Ba and sC5b9 are measured. In some embodiments of any of the methods described herein, the concentrations of one or both of C5a and C5b9 are measured. In some embodiments of any of the methods described herein, the concentrations of at least two (e.g., at least three, four, five, six, or all) of β2M, clusterin, cystatin C, NAG, TIMP-1, NGAL, and FABP-1 are measured. In some embodiments of any of the methods described herein, the concentrations of CXCL10, CXCL9, and/or KIM-1 are measured. In some embodiments of any of the methods described herein, the concentrations of one or both of D-dimer and F1+2 are measured. In some embodiments of any of the methods described herein, the concentrations of at least two (e.g., at least three, four, or all) of sCD40L, prothrombin fragment F1+2, and D-dimer, are measured. In some embodiments of any of the methods described herein, the concentrations of thrombomodulin, VCAM-1, and/or vWF are measured. In some embodiments of any of the methods described herein, the concentrations of CXCL10, MCP-1, and/or TNFR1 are measured. In some embodiments of any of the methods described herein, the concentrations of at least two (e.g., at least three, four, or all) of IFN-γ, ICAM-1, IL-1 beta, and IL-12 p70 are measured.

In some embodiments of any of the methods described herein, the concentrations of one or more of CXCL9, CXCL10, IL-1 beta, IL-12 p'70, IFN-γ, MCP-1, CCL5, sCD40L, and/or sTNFR1 is measured in the serum of the subject. In some embodiments, the concentrations of one or more of complement component C5a, sC5b9, P2 microglobulin (β2M), clusterin, cystatin C, NAG, TIMP-1, NGAL, fatty acid binding protein 1 (FABP-1), CXCL10, CXCL9, and/or KIM-1 are measured in the urine of the subject. In some embodiments of any of the methods described herein, the concentrations of one or more of NGAL, a proteolytic fragment of complement component factor B (e.g., Ba or Bb), soluble C5b9 (sC5b9), prothrombin fragment F1+2, D-dimer, thrombomodulin, and/or von Willebrand Factor (vWF) are measured in the plasma of the subject.

In some embodiments, the concentrations of two or more (e.g., three, four, five, six, seven, eight, nine, 10, 11, 12, or 13) of a proteolytic fragment of complement component factor B (e.g., Ba or Bb), soluble C5b9 (sC5b9), C5a, thrombomodulin, VCAM-1, prothrombin fragment F1+2, D-dimer, sTNFR1, β2 microglobulin (β2M), clusterin, cystatin C, TIMP-1, and fatty acid binding protein 1 (FABP-1) are measured.

In some embodiments of any of the methods described herein, the concentration of at least two of the group consisting of Ba, sC5b-9, and C5a is measured. In some embodiments of any of the methods described herein, the concentration of one or both of Ba and sC5b9 is measured. In some embodiments of any of the methods described herein, the concentration of one or both of C5a and C5b9 are measured. In some embodiments of any of the methods described herein, the concentrations of at least two individual members of the group consisting of β2M, clusterin, cystatin C, albumin, TIMP-1, NGAL, and FABP-1 are measured. In some embodiments of any of the methods described herein, the concentrations of at least two individual members of the group consisting of CXCL10, CXCL9, IL-18, MCP-1, TNFR1, VEGF, IL-6, and IFNγ are measured. In some embodiments of any of the methods described herein, the concentration of one or both of d-dimer and F1+2 is measured. In some embodiments of any of the methods described herein, the concentrations of at least two individual members of the group consisting of sCD40L, prothrombin fragment F1+2, and d-dimer are measured. In some embodiments of any of the methods described herein, the concentration of thrombomodulin, VCAM-1, or vWF is measured. In some embodiments of any of the methods described herein, the concentration of TNFR1 is measured. In some embodiments of any of the methods described herein, the concentrations of at least two individual members of the group consisting of IFN-γ, CXCL10, CXCL9, IL-18, TNFR1, VCAM-1, MCP-1, VEGF, CCL5, and IL-6 are measured. In some embodiments of any of the methods described herein, the concentration of at least one aHUS-associated biomarker protein selected from the group consisting of IFN-γ, CXCL10, CXCL9, IL-18, TNFR1, VCAM-1, MCP-1, VEGF, and IL-6 is measured. In some embodiments of any of the methods described herein, the concentration of at least one aHUS-associated biomarker selected from the group consisting of β2 microglobulin (β2M), clusterin, cystatin C, NAG, TIMP-1, NGAL, fatty acid binding protein 1 (FABP-1), CXCL10, CXCL9, albumin, and KIM-1 is measured. In some embodiments of any of the methods described herein, the concentration of at least one aHUS-associated biomarker protein selected from the group consisting of: CXCL10, CXCL9, IL-18, MCP-1, TNFR1, VEGF, IL-6, CCL5, IFNγ, IL-8, ICAM-1, IL-1 beta, and IL-12 p70 is measured. In some embodiments of any of the methods described herein, the concentration of CXCL9, CXCL10, IL-1 beta, IL-12 p'70, IFN-γ, MCP-1, CCL5, sCD40L, or sTNFR1 is measured in the serum of the subject. In some embodiments of any of the methods described herein, the concentration of at least one aHUS-associated biomarker selected from the group consisting of β2 microglobulin (β2M), clusterin, cystatin C, NAG, TIMP-1, NGAL, fatty acid binding protein 1 (FABP-1), CXCL10, CXCL9, albumin, and KIM-1 is measured in the urine of the subject. In some embodiments of any of the methods described herein, the concentration of NGAL, a proteolytic fragment of complement component factor B (e.g., Ba or Bb), soluble C5b9 (sC5b9), prothrombin fragment F1+2, D-dimer, thrombomodulin, or von Willebrand Factor (vWF) is measured in the plasma of the subject. In some embodiments of any of the methods described herein, the concentration of Ba is measured (e.g., in the plasma sample obtained from the subject).

In some embodiments of any of the methods described herein, the method requires recording the measured value(s) of the concentration of the at least one aHUS biomarker protein. The recordation can be written or on a computer readable medium. The method can also include communicating the measured value(s) of the concentration of the at least one aHUS biomarker protein to the subject and/or to a medical practitioner in whose care the subject is placed.

In some embodiments, any of the methods described herein can include the step of administering to the subject the complement inhibitor at a higher dose or with an increased frequency of dosing, relative to the predetermined dosing schedule, if the subject is not responsive to treatment with the inhibitor under the predetermined dosing schedule.

In some embodiments of any of the methods described herein, the complement inhibitor is administered to the subject under a predetermined dosing schedule based, in part, on the body weight of the subject. For example, in the case of an antagonist anti-C5 antibody (e.g., eculizumab), for subjects having a body weight greater than or equal to 40 kg, the antibody can be administered to the subject for at least 7 weeks under the following schedule: at least 800 mg of the antibody, once per week for four consecutive weeks; at least 800 mg of the antibody once during the fifth week; and at least 800 mg of the antibody bi-weekly thereafter. In some embodiments, the antibody is administered to the subject for at least 7 weeks under the following schedule: at least 900 mg of the antibody, once per week for four consecutive weeks; at least 1200 mg of the antibody once during the fifth week; and at least 1200 mg of the antibody bi-weekly thereafter.

In some embodiments of any of the methods described herein, for subjects having a body weight less than 40 kg but greater than or equal to 30 kg, the antibody can administered to the subject for at least 7 weeks under the following schedule: at least 500 mg of the antibody, once per week for two consecutive weeks; at least 700 mg of the antibody once during the third week; and at least 700 mg of the antibody bi-weekly thereafter. In some embodiments, the antibody is administered to the subject for at least 5 weeks under the following schedule: at least 600 mg of the antibody, once per week for two consecutive weeks; at least 900 mg of the antibody once during the third week; and at least 900 mg of the antibody bi-weekly thereafter.

In some embodiments of any of the methods described herein, the body weight of the subject is less than 30 kg, but is greater than or equal to 20 kg and the antibody is administered to the subject for at least 5 weeks under the following schedule: at least 500 mg of the antibody, once per week for two consecutive weeks; at least 500 mg of the antibody once during the third week; and at least 500 mg of the antibody bi-weekly thereafter. In some embodiments, the antibody is administered to the subject for at least 5 weeks under the following schedule: at least 600 mg of the antibody, once per week for two consecutive weeks; at least 600 mg of the antibody once during the third week; and at least 600 mg of the antibody bi-weekly thereafter.

In some embodiments of any of the methods described herein, the body weight of the subject is less than 20 kg, but is greater than or equal to 10 kg and the antibody is administered to the subject for at least 4 weeks under the following schedule: at least 500 mg of the antibody once a week for one week; at least 200 mg of the antibody once during the second week; and at least 200 mg of the antibody bi-weekly thereafter. In some embodiments, the antibody is administered to the subject for at least 4 weeks under the following schedule: at least 600 mg of the antibody once a week for one week; at least 300 mg of the antibody once during the second week; and at least 300 mg of the antibody bi-weekly thereafter.

In some embodiments of any of the methods described herein, the body weight of the subject is less than 10 kg, but is greater than or equal to 5 kg and the antibody is administered to the subject for at least 5 weeks under the following schedule: at least 200 mg of the antibody, once per week for one week; at least 200 mg of the antibody once during the second week; and at least 200 mg of the antibody once every three weeks thereafter. In some embodiments, the antibody is administered to the subject for at least 5 weeks under the following schedule: at least 300 mg of the antibody, once per week for one week; at least 300 mg of the antibody once during the second week; and at least 300 mg of the antibody every three weeks thereafter. Additional exemplary anti-C5 antibody dosing schedules (e.g., chronic dosing schedules) for aHUS are described in International patent application publication no. WO 2010/054403 (e.g., Tables 1 and 2 of WO 2010/054403), the disclosure of which is incorporated herein by reference in its entirety.

In some embodiments of any of the methods described herein, the inhibitor is antibody or an antigen binding fragment thereof, a small molecule, a polypeptide, a polypeptide analog, a peptidomimetic, or an aptamer. In some embodiments, the inhibitor can be one that inhibits one or more of complement components C1, C2, C3, C4, C5, C6, C7, C8, C9, Factor D, Factor B, properdin, MBL, MASP-1, MASP-2, or biologically active fragments of any of the foregoing. In some embodiments of any of the methods described herein, the complement inhibitor inhibits one or both of the generation of the anaphylatoxic activity associated with C5a and/or the assembly of the membrane attack complex associated with C5b.

The compositions can also contain naturally occurring or soluble forms of complement inhibitory compounds such as CR1, LEX-CR1, MCP, DAF, CD59, Factor H, cobra venom factor, FUT-175, complestatin, and K76 COOH.

In some embodiments, the complement inhibitor can be a complement receptor 2 (CR2)-factor H (FH) molecule comprising: a) a CR2 portion comprising CR2 (e.g., human CR2) or a fragment thereof, and b) a FH portion comprising a FH or a fragment thereof, wherein the CR2-FH molecule or fragment thereof is capable of binding to a CR2 ligand, and wherein the CR2-FH molecule is capable of inhibiting complement activation of the alternative pathway. Exemplary CR2-FH fusion proteins are described and exemplified in, e.g., International patent application publication nos. WO 2007/149567 and WO 2011/143637, the disclosures of each of which are incorporated herein by reference in their entirety. In some embodiments, the complement inhibitor comprises a targeting domain such as CR2 or an anti-C3d antibody as described in, e.g., International patent application publication no. WO 2011/163412, the disclosure of which is incorporated herein by reference in its entirety. Fusions of targeting domains with other complement inhibitors such as CD59, CD55, and factor H-like molecules can be used in the methods described herein as a complement inhibitor. See WO 2011/163412, above.

In some embodiments of any of the methods described herein, the inhibitor of complement is an antagonist antibody or antigen-binding fragment thereof. The antibody or antigen-binding fragment thereof can be selected from the group consisting of a humanized antibody, a recombinant antibody, a diabody, a chimerized or chimeric antibody, a monoclonal antibody, a deimmunized antibody, a fully human antibody, a single chain antibody, an Fv fragment, an Fd fragment, an Fab fragment, an Fab' fragment, and an F(ab')$_2$ fragment.

In some embodiments of any of the methods described herein, the antagonist antibody is an anti-C5 antibody such as eculizumab. In some embodiments, the antagonist antibody is pexelizumab, a C5-binding fragment of anti-C5 antibody.

In some embodiments of any of the methods described herein, the inhibitor of complement is selected from the group consisting of MB 12/22, MB12/22-RGD, ARC187, ARC1905, SSL7, and OmCI.

In some embodiments of any of the methods described herein, the subset of aHUS-associated biomarker proteins from which a practitioner may determine the concentration of one or more (e.g., two, three, four, five, six, seven, eight, nine, 10, or more) of can be: Ba, thrombomodulin, VCAM-1, TNFR1, F1+2, D-dimer, CXCL10, IL-6, clusterin, TIMP-1, FABP-1, β2M, and cystatin C.

In yet another aspect, the disclosure features an array comprising a plurality of binding agents, wherein each binding agent of the plurality has a unique address on the array, wherein the array comprises no more than 500 unique addresses, wherein each binding agent of the plurality binds to a different biological analyte protein, and wherein the array comprises binding agents that bind to four or more analyte proteins set forth in Table 1, e.g., selected from the group consisting of: a proteolytic fragment of complement component factor B (e.g., Ba or Bb), soluble C5b9 (sC5b9), thrombomodulin, VCAM-1, von Willebrand Factor (vWF), soluble CD40 ligand (sCD40L), prothrombin fragment F1+2, D-dimer, CXCL10, MCP-1, TNFR1, IFN-γ, ICAM-1, IL-1 beta, IL-12 p70, complement component C5a, β2 microglobulin (β2M), clusterin, cystatin C, NAG, TIMP-1, NGAL, fatty acid binding protein 1 (FABP-1), CXCL9, KIM-1, IL-18, vascular endothelial cell growth factor (VEGF), IL-6, albumin, IL-8, and CCL5. The array is useful in any of the methods described herein. In some embodiments, the array is a protein chip. In some embodiments, each address of the array is a well of an assay plate. In some embodiments, each address of the array is a particle (e.g., a bead) having immobilized thereupon a binding agent.

As used herein, the term "binding agent" includes any naturally occurring, synthetic or genetically engineered agent, such as protein, that binds an antigen (e.g., an aHUS biomarker protein). Binding agents can be or be derived from naturally-occurring antibodies. A binding protein or agent can function similarly to an antibody by binding to a specific antigen to form a complex. Binding agents or proteins can include isolated antigen-binding fragments of antibodies.

In some embodiments, the array comprises antibodies that bind to at least two (e.g., at least three, four, five, six, seven, eight, nine, 10, 11, 12, 13, 14, 15, 16, 17, 18, 19, 20, 21, 22, 23, 24, or 25) of the analyte proteins. For example, the array can comprise binding agents/antibodies that bind to at least two (e.g., three, four, five, six, seven, eight, nine, 10, 11, 12, or 13) of a proteolytic fragment of complement component factor B (e.g., Ba or Bb), soluble C5b9 (sC5b9), C5a, thrombomodulin, VCAM-1, prothrombin fragment F1+2, D-dimer, sTNFR1, β2 microglobulin (β2M), clusterin, cystatin C, TIMP-1, and fatty acid binding protein 1 (FABP-1).

In some embodiments, the array comprises no more than 200 (e.g., no more than 175, 150, 125, 100, 90, 80, 70, 60, 50, 45, 40, 35, 30, 25, or 20) unique addresses.

In yet another aspect, the disclosure features a diagnostic kit comprising one or more of any of the arrays described herein and, optionally, instructions for (a) obtaining and/or processing a biological sample (e.g., a biological fluid) from a subject and/or (b) measuring one or more analytes in a biological sample (e.g., a biological fluid) from a subject.

In another aspect, the disclosure features a diagnostic kit comprising: (a) an assay plate and (b) at least three binding agents, each binding agent capable of binding to a different biological analyte, wherein the analytes are those depicted in Table 1, e.g., selected from the group consisting of: a proteolytic fragment of complement component factor B (e.g., Ba or Bb), soluble C5b9 (sC5b9), thrombomodulin, VCAM-1, von Willebrand Factor (vWF), soluble CD40 ligand (sCD40L), prothrombin fragment F1+2, D-dimer, CXCL10, MCP-1, TNFR1, IFN-γ, ICAM-1, IL-1 beta, IL-12 p70, complement component C5a, β2 microglobulin (β2M), clusterin, cystatin C, NAG, TIMP-1, NGAL, fatty acid binding protein 1 (FABP-1), CXCL9, KIM-1, IL-18, vascular endothelial cell growth factor (VEGF), IL-6, albumin, IL-8, and CCL5. In some embodiments, the diagnostic kit comprises one or more means for measuring the activity of vWF in human plasma.

In another aspect, the disclosure features a method for diagnosing a subject as having, or being at risk for developing, atypical hemolytic uremic syndrome (aHUS). The method includes: measuring in a biological fluid the concentration of at least two aHUS-associated biomarker proteins selected from the group consisting of: a proteolytic fragment of complement component factor B (e.g., Ba or Bb), soluble C5b9 (sC5b9), thrombomodulin, VCAM-1, von Willebrand Factor (vWF), soluble CD40 ligand (sCD40L), prothrombin fragment F1+2, D-dimer, CXCL10, MCP-1, TNFR1, IFN-γ, ICAM-1, IL-1 beta, IL-12 p70, complement component C5a, (32 microglobulin (β2M), clusterin, cystatin C, NAG, TIMP-1, NGAL, fatty acid binding protein 1 (FABP-1), CXCL9, KIM-1, IL-18, vascular endothelial cell growth factor (VEGF), IL-6, albumin, IL-8, and CCL5. The biological fluid is one obtained from a subject suspected of having or at risk for developing aHUS. In accordance with the methods, an elevated concentration, as compared to the concentration in a normal control biological fluid of the same type, of at least one of Ba, sC5b-9, C5a, sCD40L, prothrombin fragment F1+2, d-dimer, thrombomodulin, VCAM-1, vWF, FABP-1, β2M, clusterin, cystatin C, TIMP-1, albumin, NGAL, CXCL10, CXCL9, IL-18, TNFR1, VCAM-1, MCP-1, VEGF, CCL5, IL-6, or IFNγ, indicates that the subject has, or is at risk for developing, aHUS. In some embodiments, the at least two aHUS-associated biomarkers can be selected from Table 11, i.e., at least two (e.g., three, four, five, six, seven, eight, nine, 10, 11, 12, or 13) of a proteolytic fragment of complement component factor B (e.g., Ba or Bb), soluble C5b9 (sC5b9), C5a, thrombomodulin, VCAM-1, prothrombin fragment F1+2, D-dimer, sTNFR1, P2 microglobulin (β2M), clusterin, cystatin C, TIMP-1, and fatty acid binding protein 1 (FABP-1).

As used herein, the term "normal," when used to modify the term "individual" or "subject" refers to an individual or group of individuals who does/do not have a particular disease or condition (e.g., aHUS) and is also not suspected of having or being at risk for developing the disease or condition. The term "normal" is also used herein to qualify a biological specimen or sample (e.g., a biological fluid) isolated from a normal or healthy individual or subject (or group of such subjects), for example, a "normal control sample" or "normal control biological fluid".

In yet another aspect, the disclosure features a method for determining whether a patient is experiencing a first acute atypical hemolytic uremic syndrome (aHUS) manifestation. The method comprises: measuring one or both of the concentration of D-dimer (e.g., the plasma concentration of d-dimer) and the concentration of fatty acid binding protein 1 (FABP-1) (e.g., the urine concentration of FABP-1), wherein an elevation in the d-dimer concentration, relative to the concentration of d-dimer in a normal control sample, and an elevation in the FABP-1 concentration, relative to the concentration of FABP-1 in a normal control sample, indicates that the aHUS patient is experiencing a first acute aHUS manifestation. In some embodiments, the elevation of one or both of d-dimer and FABP-1 can be significant elevations.

In another aspect, the disclosure features a method for treating atypical hemolytic uremic syndrome (aHUS), the method comprising administering to a subject having, suspected of having, or at risk for developing, aHUS an inhibitor of complement (e.g., an inhibitor of complement component C5) in an amount and with a frequency sufficient to effect a physiological change in at least one (e.g., at least two, three, four, five, six, seven, eight, nine, 10, 11, 12, 13, 14, 15, 16, 17, 18, 19, 20, 21, 22, 23, 24, or 25) aHUS-associated biomarker proteins, wherein the physiological change is selected from the group consisting of: (a) a reduced concentration, as compared to the concentration in a sample of biological fluid of the same type obtained from the subject prior to treatment with the inhibitor, of at least one of CXCL10, MCP-1, TNFR1, IFN-γ, a proteolytic fragment of complement component factor B (e.g., Ba or Bb), soluble C5b9 (sC5b9), prothrombin fragment F1+2, d-dimer, thrombomodulin, VCAM-1, von Willebrand Factor (vWF), complement component C5a, sC5b9, P2 microglobulin (β2M), clusterin, cystatin C, NAG, TIMP-1, NGAL, fatty acid binding protein 1 (FABP-1), albumin, CXCL10, CXCL9, and KIM-1; or (b) an increased concentration, as compared to the concentration in a sample of biological fluid of the same type obtained from the subject prior to treatment with the inhibitor, of CCL5. In some embodiments, the at least one aHUS-associated biomarker can be selected from Table 11, i.e., at least one (e.g., two, three, four, five, six, seven, eight, nine, 10, 11, 12, or 13) of a proteolytic fragment of complement component factor B (e.g., Ba or Bb), soluble C5b9 (sC5b9), C5a, thrombomodulin, VCAM-1, prothrombin fragment F1+2, D-dimer, sTNFR1, P2 microglobulin (β2M), clusterin, cystatin C, TIMP-1, and fatty acid binding protein 1 (FABP-1).

In yet another aspect, the disclosure features a method for treating atypical hemolytic uremic syndrome (aHUS) using a complement inhibitor in a manner sufficient to induce a physiological change in at least two aHUS-associated biomarker proteins. The method includes: (a) determining the concentration of at least two aHUS-associated biomarker proteins in a biological fluid obtained from the subject, wherein the aHUS-associated biomarker proteins are selected from the group consisting of: CXCL10, MCP-1, TNFR1, IFN-γ, IL-6, a proteolytic fragment of complement component factor B (e.g., Ba or Bb), soluble C5b9 (sC5b9), prothrombin fragment F1+2, d-dimer, thrombomodulin, VCAM-1, von Willebrand Factor (vWF), complement component C5a, β2 microglobulin (β2M), clusterin, cystatin C, NAG, TIMP-1, NGAL, fatty acid binding protein 1 (FABP-1), albumin, CXCL9, KIM-1, and CCL5; and (b) administering to a subject having, suspected of having, or at risk for developing, aHUS an inhibitor of complement in an amount and with a frequency sufficient to cause a physiological change in at least each of two (2) aHUS-associated biomarker proteins, wherein the physiological change is selected from the group consisting of: (a) a reduced concentration, as compared to the concentration in a sample of biological fluid of the same type obtained from the subject prior to treatment with the inhibitor, of at least one of CXCL10, MCP-1, TNFR1, IFN-γ, IL-6, a proteolytic fragment of complement component factor B (e.g., Ba or Bb), soluble C5b9 (sC5b9), prothrombin fragment F1+2, d-dimer, thrombomodulin, VCAM-1, von Willebrand Factor (vWF), complement component C5a, β2 microglobulin (β2M), clusterin, cystatin C, NAG, TIMP-1, NGAL, fatty acid binding protein 1 (FABP-1), albumin, CXCL9, or KIM-1; and (b) an increased concentration in a biological fluid of obtained from the subject, as compared to the concentration in a sample of biological fluid of the same type obtained from the subject prior to treatment with the inhibitor, of CCL5. The method can also include determining whether the physiological changes occurred. In some embodiments, the at least two aHUS-associated biomarkers can be selected from Table 11, i.e., at least two (e.g., three, four, five, six, seven, eight, nine, 10, 11, 12, or 13) of a proteolytic fragment of complement component factor B (e.g., Ba or Bb), soluble C5b9 (sC5b9), C5a, thrombomodulin, VCAM-1, prothrombin fragment F1+2, D-dimer, sTNFR1, β2 microglobulin (β2M), clusterin, cystatin C,TIMP-1, and fatty acid binding protein 1 (FABP-1).

In some embodiments, the methods can further include the step of measuring the concentrations of at least two individual aHUS-associated biomarker proteins in a biological fluid, wherein the aHUS-associated biomarker proteins are selected from the group consisting of: a proteolytic fragment of complement component factor B (e.g., Ba or Bb), soluble C5b9 (sC5b9), thrombomodulin, VCAM-1, von Willebrand Factor (vWF), soluble CD40 ligand (sCD40L), prothrombin fragment F1+2, D-dimer, CXCL10, MCP-1, TNFR1, IFN-γ, ICAM-1, IL-1 beta, IL-12 p70, complement component C5a, β2 microglobulin (β2M), clusterin, cystatin C, NAG, TIMP-1, NGAL, fatty acid binding protein 1 (FABP-1), CXCL9, KIM-1, IL-18, vascular endothelial cell growth factor (VEGF), IL-6, albumin, IL-8, and CCL5. The biological fluid is obtained from the subject. In some embodiments, the at least two aHUS-associated biomarkers can be selected from Table 11, i.e., at least two (e.g., three, four, five, six, seven, eight, nine, 10, 11, 12, or 13) of a proteolytic fragment of complement component factor B (e.g., Ba or Bb), soluble C5b9 (sC5b9), C5a, thrombomodulin, VCAM-1, prothrombin fragment F1+2, D-dimer, sTNFR1, β2 microglobulin (β2M), clusterin, cystatin C, TIMP-1, and fatty acid binding protein 1 (FABP-1).

In some embodiments, any of the methods described herein can include determining whether the at least two (e.g., at least three, four, five, six, seven, eight, nine, 10, 11, 12, 13, 14, 15, 16, 17, 18, 19, 20, 21, 22, 23, 24, or 25) physiological changes have occurred. In some embodiments, the concentrations of at least two of IFN-γ, ICAM-1, IL-1 beta, and IL-12 p70 are reduced. In some embodiments, the concentrations of both Ba and sC5b9 are reduced. In some embodiments, the concentration (e.g., the urine concentration) of each of C5a and sC5b9 is reduced. In some embodiments of any of the methods described herein, the concentrations (e.g., the urine concentration) of at least two (e.g., at least three, four, five, six, or all) of β2M, clusterin, cystatin C, NAG, TIMP-1, NGAL, and FABP-1 are reduced. In some embodiments, the concentrations (e.g., the urine concentration) of CXCL10, CXCL9, and/or KIM-1 are reduced. In some embodiments, the concentrations (e.g., plasma concentration) of one or both of D-dimer and F1+2 are reduced. In some embodiments, the concentrations (e.g., the serum and/or plasma concentrations) of at least two (e.g., at least three, or all) of sCD40L, prothrombin fragment F1+2, and D-dimer are reduced. In some embodiments, the concentrations of thrombomodulin, VCAM-1, and/or vWF are reduced. In some embodiments, the concentrations (e.g., serum concentrations) of CXCL10, MCP-1, and TNFR1 are reduced. In some embodiments, the concentrations (e.g., the serum concentrations) of at least two (e.g., at least three, four, or all) of IFN-γ, ICAM-1, IL-1 beta, and IL-12 p70 are reduced. In some embodiments, the at least two physiological changes can be a reduction in concentration of at least two aHUS-associated biomarkers selected from Table 11, i.e., at least two (e.g., three, four, five, six, seven, eight, nine, 10, 11, 12, or 13) of a proteolytic fragment of complement component factor B (e.g., Ba or Bb), soluble C5b9 (sC5b9), C5a, thrombomodulin, VCAM-1, prothrombin fragment F1+2, D-dimer, sTNFR1, β2 microglobulin (β2M), clusterin, cystatin C, TIMP-1, and fatty acid binding protein 1 (FABP-1).

In some embodiments of any of the methods described herein, the Ba concentration (e.g., plasma Ba concentration) is reduced by at least 10% by week 6 post-initiation of treatment. In some embodiments of any of the methods described herein, the Ba concentration (e.g., plasma Ba concentration) is reduced by at least 30% by week 12 post-initiation of treatment. In some embodiments of any of the methods described herein, the C5a concentration (e.g., urinary C5a concentration) is reduced by at least 40% by week 3 post-initiation of treatment. In some embodiments of any of the methods described herein, the C5a concentration (e.g., urinary C5a concentration) is reduced by at least 70% by week 6 post-initiation of treatment. In some embodiments of any of the methods described herein, the C5b-9 concentration (e.g., urinary or plasma C5b-9 concentration) is reduced by at least 50% by week 3 post-initiation of treatment. In some embodiments of any of the methods described herein, the F1+2 concentration (e.g., the plasma concentration of F1+2) is reduced by at least 20% by week 6 post-initiation of treatment. In some embodiments of any of the methods described herein, the d-dimer concentration (e.g., the plasma concentration of d-dimer) is reduced by at least 40% by week 6 post-initiation of treatment. In some embodiments of any of the methods described herein, the thrombomodulin concentration (e.g., the serum concentration of thrombomodulin) is reduced by at least 20% by week 12 post-initiation of treatment. In some embodiments of any of the methods described herein, the VCAM-1 concentration (e.g., the serum concentration of VCAM-1) is reduced by at least 20% by week 12 post-initiation of treatment.

In some embodiments of any of the methods described herein, the inhibitor of complement is administered to the subject in an amount and with a frequency sufficient to effect a physiological change in three or more aHUS-associated biomarkers. In some embodiments, the inhibitor of complement is administered to the subject in an amount and with a frequency sufficient to effect a physiological change in at least four aHUS-associated biomarkers. In some embodiments, the inhibitor of complement is administered to the subject in an amount and with a frequency sufficient to effect a physiological change in at least five aHUS-associated biomarkers. In some embodiments, the inhibitor of complement is administered to the subject in an amount and with a frequency sufficient to effect a physiological change in at least 10 aHUS-associated biomarkers. In some embodiments, the inhibitor of complement component C5 is administered to the subject in an amount and with a frequency sufficient to effect a physiological change in 15 or more aHUS-associated biomarkers.

In some embodiments, a physiological change in at least two (e.g., at least three, four, five, six, seven, eight, nine, 10, 11, 12, 13, 14, 15, 16, 17, 18, 19, 20, 21, 22, 23, 24, or 25 or more) aHUS-associated biomarker proteins occurs within two days, three days, four days, five days, six days, one week, two weeks, three weeks, four weeks, six weeks, two months, nine weeks, or three months or more after administration (e.g., chronic administration) of the inhibitor.

In some embodiments, the concentration of at least one (e.g., at least two, three, four, five, six, seven, eight, nine, 10, 11, 12, 13, 14, 15, 16, 17, 18, 19, 20, 21, 22, 23, 24, or 25) aHUS-associated biomarker protein is reduced by at least 5 (e.g., at least 10, 15, 20, 25, 30, 35, 40, 45, 50, 55, 60, 65, or 70) % following administration of the inhibitor.

In some embodiments, the concentration of at least one (e.g., at least two, three, four, five, six, seven, eight, nine, 10, 11, 12, 13, 14, 15, 16, 17, 18, 19, 20, 21, 22, 23, 24, or 25) aHUS-associated biomarker protein is reduced to within 50 (e.g., 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1) % of the normal concentration of the biomarker protein following administration of one or more doses of the inhibitor.

In some embodiments of any of the methods described herein, the concentration of FABP-1 (e.g., urinary FABP-1) is reduced by at least 80% (e.g., 85, 90, 95, or up to 100%) following administration of an inhibitor of human complement (e.g., an anti-C5 antibody). In some embodiments of any of the methods described herein, the concentration of cystatin-C (e.g., urinary cystatin-C) is reduced by at least 80% (e.g., 85, 90, 95, 99, or up to 100%) following administration of an inhibitor of human complement (e.g., an anti-C5 antibody). In some embodiments of any of the methods described herein, the concentration of clusterin (e.g., urinary clusterin) is reduced by at least 80% (e.g., 85, 90, 95, 98, or up to 100%) following administration of an inhibitor of human complement (e.g., an anti-C5 antibody). In some embodiments of any of the methods described herein, the concentration of a proteolytic fragment of factor B (e.g., Ba) is reduced by at least 10% (e.g., 15, 20, 25, 30, or 40%) following administration of an inhibitor of human complement (e.g., an anti-C5 antibody). In some embodiments of any of the methods described herein, the concentration of sTNFR1 is reduced by at least 80% (e.g., 85, 90, or more %) following administration of an inhibitor of human complement (e.g., an anti-C5 antibody). In some embodiments of any of the methods described herein, the concentration of thrombomodulin or sVCAM-1 is reduced by at least 80% (e.g., 85, 90, 95, or up to 100%) following administration of an inhibitor of human complement (e.g., an anti-C5 antibody). In some embodiments of any of the methods described herein, the concentration of one or both of F1+2 or D-dimer is reduced by at least 80% (e.g., 85, 90, 95, or more %) following administration of an inhibitor of human complement (e.g., an anti-C5 antibody).

In some embodiments of any of the methods described herein, the concentration of at least one (e.g., at least two, three, four, five, six, seven, eight, nine, 10, 11, 12, 13, 14, 15, 16, 17, 18, 19, 20, 21, 22, 23, 24, or 25) of the aHUS-associated biomarker proteins is normalized following administration of the inhibitor. In some embodiments, the concentrations (e.g., the urine concentrations) of at least three of (β2 microglobulin (β2M), clusterin, cystatin C, NAG, TIMP-1, NGAL, fatty acid binding protein 1 (FABP-1), CXCL10, CXCL9, and KIM-1 are normalized.

As used herein, the term "normalized" or like grammatical terms, when used in the context of the effect of a complement inhibitor therapy on the concentration or activity of an aHUS biomarker protein, refers to a concentration or activity measured in a biological fluid of a biomarker protein that has been brought within 50 (e.g., 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1) % of the average concentration or activity range of the aHUS biomarker protein as measured in a sample of the same type of biological fluid obtained from a group of healthy individuals (normal individuals). For example, treatment of an aHUS patient with a complement inhibitor can normalize an elevated urine clusterin concentration to within, e.g., 20% of the normal average urine concentration range of clusterin. In some embodiments, treatment with the complement inhibitor would restore the urine concentration of clusterin to within the normal average urine concentration range of clusterin.

In some embodiments of any of the methods described herein, the subject has received dialysis at least once (e.g., at least twice, thrice, four times, or five times or more) within the three months (e.g., 11, 10, 9, 8, 7, 6, 5, 4, 3, 2, or 1 week(s)) prior to treatment with the inhibitor. For example, in some embodiments the subject received dialysis one time two months before receiving the complement inhibitor therapy. In another example, the subject may be one who has received dialysis three times within the three month period just prior to receiving the complement inhibitor therapy. In some embodiments of any of the methods described herein, relative to the concentration in a healthy subject, the concentrations of one or more of TNFR1, Ba, thrombomodulin fragment F1+2, and sC5b9 are elevated. In some embodiments of any of the methods described herein, relative to the concentrations (e.g., the urine concentrations) in a healthy human, the concentrations of one or more of β2M, sC5b9, C5a, cystatin C, clusterin, TIMP-1, and NGAL are elevated.

In some embodiments of any of the methods described herein, the subject (e.g., a human subject) is experiencing a first acute aHUS manifestation. For example, prior to treatment with the complement inhibitor, the subject can have elevated concentrations, relative to the normal concentrations, of one or both of D-dimer and FABP-1.

In some embodiments of any of the methods described herein, the subject (e.g., a human subject) is one having aHUS, but deemed to be in clinical remission (e.g., the subject is one having normal levels of platelets or other hematologic markers such as LDH or haptoglobin). In some embodiments, such a subject is one having elevated levels of one or more of the aHUS biomarkers described herein including, but not limited, one or more of Ba, D-dimer, VCAM-1, and prothrombin fragments 1+2.

It is understood that for any of the methods described herein, the concentration and/or activity of one or more aHUS biomarker proteins can be determined. For example, in some embodiments, a practitioner may measure the activity of vWF in a biological sample obtained from the subject as a proxy for the concentration of vWF (or other biomarker proteins) in the sample. Methods for assessing relative activity of the aHUS biomarker proteins set forth in Table 1 are known in the art.

As discussed in detail herein (for example, in the working examples), aHUS is a genetic, life threatening disease involving chronic complement dysregulation. Patients afflicted with the disease suffer from, among other things, thrombotic microangiopathy (TMA), which can result in stroke and kidney failure. Eculizumab, an antagonist anti-C5 antibody, has been shown to dramatically reduce TMA, normalize platelet levels, and improve renal function of aHUS patients. Yet, even with the clear and robust clinical benefit of complement inhibitor therapy for aHUS patients, some patients still experience elevated levels of several aHUS biomarker proteins in the face of treatment. For example, the inventors have discovered that, in some patients, a proteolytic fragment of complement component factor B (e.g., Ba or Bb) levels (e.g., in plasma) do not normalize following treatment with an antagonist anti-C5 antibody. In addition, for some patients, levels of prothrombin fragment 1+2, D-dimer, thrombomodulin, VCAM-1, TNFR1, and CXCL10 levels are reduced but do not normalize over time. While the disclosure is not bound by any particular theory or mechanism of action, these observations suggest that, for some patients, low levels of inflammation and coagulopathy may persist even with complement inhibitor therapy. Thus, the disclosure contemplates methods in which a complement inhibitor is administered in combination with a second therapy to address the low level of persistent inflammation in some patients with aHUS.

Thus, in yet another aspect, the disclosure features a method for treating atypical hemolytic uremic syndrome (aHUS). The method comprises administering (e.g., chronically administering) to a subject (e.g., a human subject) having, suspected of having, or at risk for developing, aHUS a therapeutically effective amount of an inhibitor of complement (e.g., an inhibitor of complement component C5) and a therapeutically effective amount of: (i) an anti-coagulant, (ii) a fibrinolytic agent; (iii) an anti-inflammatory agent; or (iv) an inhibitor of IL-6, IL-8, CXCL-9, IL-18, or VEGF. In some embodiments, two inhibitors of complement can be used (e.g., an inhibitor of C5 and an inhibitor of C3, such as, an anti-Factor B antibody, an anti-C3 antibody, or an anti-C3b antibody). In some embodiments, at the time of discontinuing therapy with an inhibitor of C5, an inhibitor of complement component C3 can be administered to the patient for a time sufficient to reduce upstream alternative pathway activation.

In some embodiments, the methods can include monitoring the status of one or more aHUS biomarkers and determining whether to start a second therapy (in addition to complement inhibitor therapy) or modify the dosing regimen of one or more second therapies being administered to an aHUS patient. For example, during treatment (e.g., chronic treatment) with a complement inhibitor, the concentration of one or more aHUS associated biomarker proteins can be measured in one or more biological fluids obtained from the subject. If the concentration of one or more of the biomarker proteins has not normalized and/or remains elevated, a medical practitioner may elect to administer to the subject one or more additional secondary agents (e.g., anti-inflammatories) to address any pathophysiological effects resulting from the elevated biomarkers.

The complement inhibitor can be any of those described herein. In some embodiments of any of the methods described herein, the inhibitor is antibody or an antigen binding fragment thereof, a small molecule, a polypeptide, a polypeptide analog, a peptidomimetic, or an aptamer. In some embodiments, the inhibitor can be one that inhibits one or more of complement components C1, C2, C3, C4, C5, C6, C7, C8, C9, Factor D, Factor B, properdin, MBL, MASP-1, MASP-2, or biologically active fragments of any of the foregoing. In some embodiments of any of the methods described herein, the complement inhibitor inhibits one or both of the generation of the anaphylatoxic activity associated with C5a and/or the assembly of the membrane attack complex associated with C5b.

The compositions can also contain naturally occurring or soluble forms of complement inhibitory compounds such as CR1, LEX-CR1, MCP, DAF, CD59, Factor H, cobra venom factor, FUT-175, complestatin, and K76 COOH.

In some embodiments of any of the methods described herein, the inhibitor of complement is an antagonist antibody or antigen-binding fragment thereof. The antibody or antigen-binding fragment thereof can be selected from the group consisting of a humanized antibody, a recombinant antibody, a diabody, a chimerized or chimeric antibody, a monoclonal antibody, a deimmunized antibody, a fully human antibody, a single chain antibody, an Fv fragment, an Fd fragment, an Fab fragment, an Fab' fragment, and an F(ab')$_2$ fragment.

In some embodiments of any of the methods described herein, the antagonist antibody is an anti-C5 antibody such as eculizumab. In some embodiments, the antagonist antibody is pexelizumab, a C5-binding fragment of anti-C5 antibody.

In some embodiments of any of the methods described herein, the inhibitor of complement is selected from the group consisting of MB12/22, MB12/22-RGD, ARC187, ARC1905, SSL7, and OmCI.

In some embodiments, the anti-coagulant is selected from the group consisting of: a coumarin, heparin, a factor Xa inhibitor, and a thrombin inhibitor. Examples of anti-coagulants include, e.g., warfarin (Coumadin), aspirin, heparin, phenindione, fondaparinux, idraparinux, and thrombin inhibitors (e.g., argatroban, lepirudin, bivalirudin, or dabigatran).

In some embodiments, the fibrinolytic agent is selected from the group consisting of ancrod, ε-aminocaproic acid, antiplasmin-a$_1$, prostacyclin, and defibrotide.

In some embodiments, the anti-inflammatory agent is an anti-cytokine agent such as an antagonist antibody (or antigen-binding fragment thereof) or a soluble cytokine receptor, which binds to an inflammatory cytokine and inhibits the activity of the cytokine. The anti-cytokine agent can be, e.g., a TNF inhibitor (e.g., an anti-TNF antibody or soluble TNF receptor protein) or an anti-CD20 agent.

Anti-inflammatory agents also include, e.g., steroids (e.g., dexamethasone), non-steroidal anti-inflammatory drugs (NSAIDs) (e.g., indomethacin, naproxen, sulindac, diclofenac, aspirin, flurbiprofen, oxaprozin, salsalate, difunisal, piroxicam, etodolac, meclofenamate, ibuprofen, fenoprofen, ketoprofen, nabumetone, tolmetin, choline magnesium salicylate, COX-2 inhibitors, TNF alpha antagonists (etanercept, adalimumab, infliximab, golimumab), disease modifying anti-rheumatic drugs (DMARDS) (e.g., sulfasalazine, methotrexate), cyclosporin, retinoids and corticosteroids.

In yet another aspect, the disclosure features a method for determining whether the concentration of one or more aHUS-associated biomarker proteins are elevated in a patient having, suspected of having, or at risk for developing, atypical hemolytic uremic syndrome (aHUS), wherein the method comprises: (i) measuring in a biological sample obtained from the patient the concentration of each of at least two aHUS-associated biomarkers from Table 11 (infra), i.e., selected from the group consisting of: a proteolytic fragment of factor B, C5a, soluble C5b-9 (sC5b-9), soluble TNFR1 (sTNFR1), soluble VCAM-1 (sVCAM-1), thrombomodulin, prothrombin fragments 1 and 2 (F1+2), D-dimer, clusterin, TIMP-1, FABP-1, beta-2 microglobulin (β2m), and cystatin-C, and (ii) determining whether the patient has an elevated concentration of each of at least two of the aHUS-associated biomarkers as compared to a normal control concentration of the same at least two biomarkers. In some embodiments, the at least two aHUS-associated biomarker proteins are measured using an immunoassay, such as, an enzyme-linked immunosorbent assay (ELISA) or a radioimmunoassay (RIA). The biological fluid can be, e.g., blood, a blood fraction (e.g., plasma or serum), or urine. It is understood that any combination of any two or more (e.g., three, four, five, six, seven, eight, nine, 10, 11 or 12) of the aforementioned aHUS-biomarkers can be measured and analyzed in accordance with the methods described herein.

In another aspect, the disclosure features a method for diagnosing a patient as having atypical hemolytic uremic syndrome (aHUS) (or confirming a diagnosis of aHUS, e.g., where the patient has met two or more of the inclusion criteria discussed under Example 1), wherein the method comprises: (i) measuring in a biological sample obtained from a patient suspected of having aHUS or at risk of developing aHUS the concentration of each of at least two aHUS-associated biomarkers selected from the group consisting of: a proteolytic fragment of factor B, C5a, soluble C5b-9 (sC5b-9), soluble TNFR1 (sTNFR1), soluble VCAM-1 (sVCAM-1), thrombomodulin, prothrombin fragments 1 and 2 (F1+2), D-dimer, clusterin, TIMP-1, FABP-1, beta-2 microglobulin (β2m), and cystatin-C, and (ii) diagnosing a patient as having aHUS (or confirming a diagnosis of aHUS) if the concentration of each of at least two of the aHUS-associated biomarkers are elevated as compared to a normal control concentration of the same at least two biomarkers. In some embodiments, the at least two aHUS-associated biomarker proteins are measured using an immunoassay, such as, an enzyme-linked immunosorbent assay (ELISA) or a radioimmunoassay (RIA). The biological fluid can be, e.g., blood, a blood fraction (e.g., plasma or serum), or urine. It is understood that any combination of any two or more (e.g., three, four, five, six, seven, eight, nine, 10, 11 or 12) of the aforementioned aHUS-biomarkers can be measured and analyzed in accordance with the methods described herein.

A normal control concentration, as used in any of the methods described herein, can be (or can be based on), e.g., the concentration of a given aHUS-associated biomarker protein in a biological sample or biological samples obtained from one or more (e.g., two, three, four, five, six, seven, eight, nine, 10, 15, 20, 25, 30, 35, or 40 or more) healthy individuals. In some embodiments, a normal control concentration of a biomarker can be (or can be based on), e.g., the concentration of the biomarker in a pooled sample obtained from two or more (e.g., two, three, four, five, six, seven, eight, nine, 10, 15, 20, 25, 30, 35, or 40 or more) healthy individuals. In some embodiments of any of the methods described herein, the pooled samples can be from healthy individuals or, at least, individuals who do not have or are not suspected of having (nor at risk for developing) aHUS. For example, determining whether a subject is one having aHUS can involve comparing the measured concentration of one or more complement component proteins (e.g., Table 1 or Table 11) in a biological sample (or several different types of biological samples) obtained from the patient and comparing the measured concentration to the average concentration of the same proteins in the pooled healthy samples. Such healthy human control concentrations can be, in some embodiments, a range of values, or a median or mean value obtained from the range.

In some embodiments, the concentration of at least one aHUS-associated biomarker is measured in two or more types of biological fluid. In some embodiments, the concentration of the first of the at least two aHUS biomarker proteins is measured in one type of biological fluid and the concentration of the second of the at least two aHUS biomarker proteins is measured in a second type of fluid.

In some embodiments of any of the methods described herein, the concentration of the proteolytic fragment of factor B is measured. The fragment can be, e.g., Ba. The biological sample can be a plasma sample. As described in Table 11, the normal control concentration of Ba can be less than 1000 ng/mL. The normal control concentration of Ba can be less than 600 ng/mL. The normal control concentration of Ba can be between 300 and 600 ng/mL.

In some embodiments, the concentration of Ba in the biological sample is deemed elevated when it is at least two fold greater than the normal control concentration of Ba. In some embodiments, the concentration of Ba in the biological sample is deemed elevated when it is at least five fold greater than the normal control concentration of Ba. In some embodiments, the concentration of Ba in the biological sample is deemed elevated when it is at least 1500 ng/mL. In some embodiments, the concentration of Ba in the biological sample is deemed elevated when it is at least 2500 ng/mL.

In some embodiments of any of the methods described herein, the concentration of C5a is measured. The biological sample in which C5a is measured can be a urine sample. And in some embodiments, the normal control concentration of C5a is less than 2 ng per mg of urinary creatinine. In some embodiments, the normal control concentration of C5a is less than 1 ng per mg of urinary creatinine. In some embodiments, the normal control concentration of C5a is between 0 and 0.7 ng per mg of urinary creatinine.

In some embodiments of any of the methods described herein, the concentration of C5a in the biological sample is deemed elevated when it is at least two fold greater than the normal control concentration of C5a. In some embodiments, the concentration of C5a in the biological sample is deemed elevated when it is at least ten fold greater than the normal control concentration of C5a. In some embodiments, the concentration of C5a in the biological sample is deemed elevated when it is at least forty fold greater than the normal control concentration of C5a. In some embodiments, the concentration of C5a in the biological sample is deemed elevated when it is at least 5 ng per mg of urinary creatinine. In some embodiments, the concentration of C5a in the biological sample is deemed elevated when it is at least 9 ng per mg of urinary creatinine.

In some embodiments of any of the methods described herein, the concentration of sC5b-9 is measured. The biological sample in which sC5b-9 is measured can be a urine sample. And in some embodiments, the normal control concentration of sC5b-9 is less than 2 ng per mg of urinary creatinine. The normal control concentration of sC5b-9 can be less than 1 ng per mg of urinary creatinine. In some embodiments, the normal control concentration of sC5b-9 is between 0 and 0.6 ng per mg of urinary creatinine.

In some embodiments of any of the methods described herein, the concentration of sC5b-9 in the biological sample is deemed elevated when it is at least ten fold greater than the normal control concentration of sC5b-9. In some embodiments, the concentration of sC5b-9 in the biological sample is deemed elevated when it is at least fifty fold greater than the normal control concentration of sC5b-9. In some embodiments, the concentration of sC5b-9 in the biological sample is deemed elevated when it is at least one hundred fold greater than the normal control concentration of sC5b-9. In some embodiments, the concentration of sC5b-9 in the biological sample is deemed elevated when it is at least 20 ng per mg of urinary creatinine. In some embodiments, the concentration of sC5b-9 in the biological sample is deemed elevated when it is at least 30 ng per mg of urinary creatinine.

In some embodiments of any of the methods described herein, the concentration of sTNFR1 is measured. The biological sample in which sTNFR1 is measured can be a serum sample. And in some embodiments, the normal control concentration of sTNFR1 is less than 2000 pg/mL. In some embodiments, the normal control concentration of sTNFR1 is less than 1500 pg/mL. In some embodiments, the normal control concentration of sTNFR1 is between 400 and 1500 pg/mL.

In some embodiments of any of the methods described herein, the concentration of sTNFR1 in the biological sample is deemed elevated when it is at least two fold greater than the normal control concentration of sTNFR1. In some embodiments, the concentration of sTNFR1 in the biological sample is deemed elevated when it is at least five fold greater than the normal control concentration of sTNFR1. In some embodiments, the concentration of sTNFR1 in the biological sample is deemed elevated when it is at least fifteen fold greater than the normal control concentration of sTNFR1. In some embodiments, the concentration of sTNFR1 in the biological sample is deemed elevated when it is at least 10,000 pg/mL. In some embodiments, the concentration of sTNFR1 in the biological sample is deemed elevated when it is at least 15,000 pg/mL.

In some embodiments of any of the methods described herein, the concentration of sVCAM-1 is measured. The biological sample in which sVCAM-1 is measured can be a serum sample. And in some embodiments, the normal control concentration of sVCAM-1 is less than 500 ng/mL. In some embodiments, the normal control concentration of sVCAM-1 is less than 300 ng/mL. In some embodiments, the normal control concentration of sVCAM-1 is between 100 and 500 ng/mL.

In some embodiments of any of the methods described herein, the concentration of sVCAM-1 in the biological sample is deemed elevated when it is at least 10% greater than the normal control concentration of sVCAM-1. In some embodiments, the concentration of sVCAM-1 in the biological sample is deemed elevated when it is at least 30% greater than the normal control concentration of sVCAM-1. In some embodiments, the concentration of sVCAM-1 in the biological sample is deemed elevated when it is at least 50% greater than the normal control concentration of sVCAM-1. In some embodiments, the concentration of sVCAM-1 in the biological sample is deemed elevated when it is at least 550 ng/mL. In some embodiments, the concentration of sVCAM-1 in the biological sample is deemed elevated when it is at least 650 ng/mL.

In some embodiments of any of the methods described herein, the concentration of thrombomodulin is measured. The biological sample in which thrombomodulin is measured can be a plasma sample. And in some embodiments, the normal control concentration of thrombomodulin is less than 5 ng/mL. In some embodiments, the normal control concentration of thrombomodulin is less than 3 ng/mL. In some embodiments, the normal control concentration of thrombomodulin is between 2 and 6 ng/mL.

In some embodiments of any of the methods described herein, the concentration of thrombomodulin in the biological sample is deemed elevated when it is at least 10% greater than the normal control concentration of thrombomodulin. In some embodiments, the concentration of thrombomodulin in the biological sample is deemed elevated when it is at least 30% greater than the normal control concentration of thrombomodulin. In some embodiments, the concentration of thrombomodulin in the biological sample is deemed elevated when it is at least 50% greater than the normal control concentration of thrombomodulin. In some embodiments, the concentration of thrombomodulin in the biological sample is deemed elevated when it is at least 8 ng/mL. In some embodiments, the concentration of thrombomodulin in the biological sample is deemed elevated when it is at least 10 ng/mL.

In some embodiments of any of the methods described herein, the concentration of F1+2 is measured. The biological sample in which F1+2 is measured can be a plasma sample. And in some embodiments, the normal control concentration of F1+2 is less than 400 pmol/L. In some embodiments, the normal control concentration of F1+2 is less than 300 pmol/L. In some embodiments, the normal control concentration of F1+2 is between 50 and 400 pmol/L.

In some embodiments of any of the methods described herein, the concentration of F1+2 in the biological sample is deemed elevated when it is at least 30% greater than the normal control concentration of F1+2. In some embodiments, the concentration of F1+2 in the biological sample is deemed elevated when it is at least 50% greater than the normal control concentration of F1+2. In some embodiments, the concentration of F1+2 in the biological sample is deemed elevated when it is at least 100% greater than the normal control concentration of F1+2. In some embodiments, the concentration of F1+2 in the biological sample is deemed elevated when it is at least 900 pmol/L. In some embodiments, the concentration of F1+2 in the biological sample is deemed elevated when it is at least 1000 pmol/L.

In some embodiments of any of the methods described herein, the concentration of D-dimer is measured. The biological sample in which D-dimer is measured can be a plasma sample. And in some embodiments, the normal control concentration of D-dimer is less than 500 µg/L. In some embodiments, the normal control concentration of D-dimer is less than 400 µg/L. In some embodiments, the normal control concentration of D-dimer is between 100 and 500 µg/L.

In some embodiments of any of the methods described herein, the concentration of D-dimer in the biological sample is deemed elevated when it is at least two-fold greater than the normal control concentration of D-dimer. In some embodiments, the concentration of D-dimer in the biological sample is deemed elevated when it is at least five-fold greater than the normal control concentration of D-dimer. In some embodiments, the concentration of D-dimer in the biological sample is deemed elevated when it is at least ten-fold greater than the normal control concentration of D-dimer. In some embodiments, the concentration of D-dimer in the biological sample is deemed elevated when it is at least 1500 µg/L. In some embodiments, the concentration of D-dimer in the biological sample is deemed elevated when it is at least 2500 µg/L.

In some embodiments of any of the methods described herein, the concentration of clusterin is measured. The biological sample in which clusterin is measured can be a urine sample. And in some embodiments, the normal control concentration of clusterin is less than 500 ng per mg of urinary creatinine. The normal control concentration of clusterin can be, e.g., less than 400 ng per mg of urinary creatinine. In some embodiments, the normal control concentration of clusterin is between 0 and 500 ng per mg of urinary creatinine.

In some embodiments of any of the methods described herein, the concentration of clusterin in the biological sample is deemed elevated when it is at least two-fold greater than the normal control concentration of clusterin. In some embodiments, the concentration of clusterin in the biological sample is deemed elevated when it is at least five-fold greater than the normal control concentration of clusterin. In some embodiments, the concentration of clusterin in the biological sample is deemed elevated when it is at least ten-fold greater than the normal control concentration of clusterin. In some embodiments, the concentration of clusterin in the biological sample is deemed elevated when it is at least 900 ng per mg of urinary creatinine. In some embodiments, the concentration of clusterin in the biological sample is deemed elevated when it is at least 1200 ng per mg of urinary creatinine.

In some embodiments of any of the methods described herein, the concentration of TIMP-1 is measured. The biological sample in which TIMP-1 is measured can be a urine sample. And in some embodiments, the normal control concentration of TIMP-1 is less than 10 ng per mg of urinary creatinine. In some embodiments, the normal control concentration of TIMP-1 is less than 5 ng per mg of urinary creatinine. In some embodiments, the normal control concentration of TIMP-1 is between 0 and 10 ng per mg of urinary creatinine.

In some embodiments of any of the methods described herein, the concentration of TIMP-1 in the biological sample is deemed elevated when it is at least two-fold greater than the normal control concentration of TIMP-1. In some embodiments, the concentration of TIMP-1 in the biological sample is deemed elevated when it is at least ten-fold greater than the normal control concentration of TIMP-1. In some embodiments, the concentration of TIMP-1 in the biological sample is deemed elevated when it is at least twenty-fold greater than the normal control concentration of TIMP-1. In some embodiments, the concentration of TIMP-1 in the biological sample is deemed elevated when it is at least 15 ng per mg of urinary creatinine. In some embodiments, the concentration of TIMP-1 in the biological sample is deemed elevated when it is at least 20 ng per mg of urinary creatinine.

In some embodiments of any of the methods described herein, the concentration of FABP-1 (also referred to herein as L-FABP-1) is measured. The biological sample in which C5a is measured can be a urine sample. And in some embodiments, the normal control concentration of FABP-1 is less than 20 ng per mg of urinary creatinine. In some embodiments, the normal control concentration of FABP-1 is less than 15 ng per mg of urinary creatinine. In some embodiments, the normal control concentration of FABP-1 is between 0 and 20 ng per mg of urinary creatinine.

In some embodiments of any of the methods described herein, the concentration of FABP-1 in the biological sample is deemed elevated when it is at least two-fold greater than the normal control concentration of FABP-1. In some embodiments, the concentration of FABP-1 in the biological sample is deemed elevated when it is at least ten-fold greater than the normal control concentration of FABP-1. In some embodiments, the concentration of FABP-1 in the biological sample is deemed elevated when it is at least twenty-fold greater than the normal control concentration of FABP-1. In some embodiments, the concentration of FABP-1 in the biological sample is deemed elevated when it is at least 40 ng per mg of urinary creatinine. In some embodiments, the concentration of FABP-1 in the biological sample is deemed elevated when it is at least 50 ng per mg of urinary creatinine.

In some embodiments of any of the methods described herein, the concentration of β2m is measured. The biological sample in which β2m is measured can be a urine sample. And in some embodiments, the normal control concentration of β2m is less than 5 µg per mg of urinary creatinine. In some embodiments, the normal control concentration of β2m is less than 3 µg per mg of urinary creatinine. In some embodiments, the normal control concentration of β2m is between 0 and 5 µg per mg of urinary creatinine.

In some embodiments of any of the methods described herein, the concentration of β2m in the biological sample is deemed elevated when it is at least two-fold greater than the normal control concentration of β2m. In some embodiments of any of the methods described herein, the concentration of β2m in the biological sample is deemed elevated when it is at least ten-fold greater than the normal control concentration of β2m. In some embodiments, the concentration of β2m in the biological sample is deemed elevated when it is at least twenty-fold greater than the normal control concentration of β2m. In some embodiments, the concentration of β2m in the biological sample is deemed elevated when it is at least 15 µg per mg of urinary creatinine. In some embodiments, the concentration of β2m in the biological sample is deemed elevated when it is at least 20 µg per mg of urinary creatinine.

In some embodiments of any of the methods described herein, the concentration of cystatin-C is measured. The biological sample in which cystatin-C is measured can be a urine sample. And in some embodiments, the normal control concentration of cystatin-C is less than 400 ng per mg of urinary creatinine. In some embodiments, the normal control concentration of cystatin-C is less than 300 ng per mg of urinary creatinine. In some embodiments, the normal control concentration of cystatin-C is between 0 and 400 ng per mg of urinary creatinine.

In some embodiments of any of the methods described herein, the concentration of cystatin-C in the biological sample is deemed elevated when it is at least two-fold greater than the normal control concentration of cystatin-C. In some embodiments, the concentration of cystatin-C in the biological sample is deemed elevated when it is at least ten-fold greater than the normal control concentration of cystatin-C. In some embodiments, the concentration of cystatin-C in the biological sample is deemed elevated when it is at least twenty-fold greater than the normal control concentration of cystatin-C. In some embodiments, the concentration of cystatin-C in the biological sample is deemed elevated when it is at least 900 ng per mg of urinary creatinine. In some embodiments, the concentration of cystatin-C in the biological sample is deemed elevated when it is at least 1200 ng per mg of urinary creatinine.

In some embodiments of any of the methods described herein, the concentrations of two or more of proteolytic fragments of factor B, C5a, and sC5b-9 are measured. In some embodiments of any of the methods described herein, the concentrations of C5a and sC5b-9 are measured. In some embodiments of any of the methods described herein, the concentrations of sVCAM-1 and thrombomodulin are measured. In some embodiments of any of the methods described herein, the concentrations of F1+2 and D-dimer are measured. In some embodiments of any of the methods described herein, the concentrations of two or more of clusterin, TIMP-1, β2m, FABP-1, and cystatin-C are measured.

In yet another aspect, the disclosure features a method for assessing the level of alternative pathway activation in a patient having aHUS, suspected of having aHUS, or at risk for developing aHUS, before, during, or after treatment with a complement inhibitor, such as, an anti-C5 antibody. The method comprises: measuring the concentration of a proteolytic fragment of factor B (e.g., Ba or Bb) in a biological sample obtained from a patient treated with an inhibitor of complement (e.g., an inhibitor of human complement component C5, such as, an anti-C5 antibody).

In yet another aspect, the disclosure features a method for determining whether a patient has responded to therapy with a complement inhibitor (e.g., had a reduction in risk of developing thrombosis or had a reduction in the number, frequency, or occurrence of thrombotic microangiopathy), the method comprising measuring the concentration of one or more biomarkers of thrombosis or coagulation set forth in Table 1 or 11, e.g., F1+2, D-dimer, vWF, or thrombomodulin, in a biological sample obtained from a patient at elevated risk of, suffering from, or suspected of having, thrombotic microangiopathy (TMA) and treated with a complement inhibitor; and determining that the patient has responded to the therapy if the concentration of the one or more biomarkers in the biological sample is reduced, as compared to the concentration of the one or more biomarkers in a biological sample of the same type obtained from the patient prior to treatment with the complement inhibitor or determining that the patient has not responded to the therapy if the concentration of the one or more biomarkers in the biological sample is not reduced, as compared to the concentration of the one or more biomarkers in a biological sample of the same type obtained from the patient prior to treatment with the complement inhibitor. In some embodiments, the patient has, is suspected of having, or is at risk for developing, aHUS.

In another aspect, the disclosure features a method for determining whether an aHUS patient has responded to therapy with a complement inhibitor, the method comprising measuring the concentration of one or more biomarkers of terminal complement activation set forth in Table 1 or 11, e.g., C5a and/or sC5b-9, in a biological sample obtained from a patient having, suspected of having, or at risk for developing, aHUS and treated with a complement inhibitor (e.g., an anti-C5 antibody); and determining that the patient has responded to the therapy if the concentration of the one or more biomarkers in the biological sample is reduced, as compared to the concentration of the one or more biomarkers in a biological sample of the same type obtained from the patient prior to treatment with the complement inhibitor or determining that the patient has not responded to the therapy if the concentration of the one or more biomarkers in the biological sample is not reduced, as compared to the concentration of the one or more biomarkers in a biological sample of the same type obtained from the patient prior to treatment with the complement inhibitor. Thus, the method can be used to assess or monitor terminal complement blockade in an aHUS patient treated with a complement inhibitor. In embodiments in which the patient is non-responsive, or less responsive to therapy, the method can also include changing the dose amount or dose frequency of the complement inhibitor or electing a different complement inhibitor (e.g., an inhibitor of C3 activation) for use in treating the patient.

In another aspect, the disclosure features a method for determining whether an aHUS patient has responded to therapy with a complement inhibitor, the method comprising measuring the concentration of one or more biomarkers of vascular inflammation or endothelial activation set forth in Table 1 or 11, e.g., sTNFR1, sVCAM-1, or thrombomodulin, in a biological sample obtained from a patient having, suspected of having, or at risk for developing, aHUS; and determining that the patient has responded to the therapy if the concentration of the one or more biomarkers in the biological sample is reduced, as compared to the concentration of the one or more biomarkers in a biological sample of the same type obtained from the patient prior to treatment with the complement inhibitor or determining that the patient has not responded to the therapy if the concentration of the one or more biomarkers in the biological sample is not reduced, as compared to the concentration of the one or more biomarkers in a biological sample of the same type obtained from the patient prior to treatment with the complement inhibitor. Thus, the method can be used to assess or monitor vascular inflammation in an aHUS patient treated with a complement inhibitor. In embodiments in which the patient is non-responsive, or less responsive to therapy, the method can also include changing the dose amount or dose frequency of the complement inhibitor or electing a different complement inhibitor (e.g., an inhibitor of C3 activation) for use in treating the patient.

In another aspect, the disclosure features a method for determining whether an aHUS patient has responded to therapy with a complement inhibitor, the method comprising measuring the concentration of one or more biomarkers of renal injury set forth in Table 1 or 11, e.g., clusterin, TIMP-1, FABP-1, β2m, and/or cystatin-C, in a biological sample obtained from a patient having, suspected of having, or at risk for developing, aHUS; and determining that the patient has responded to the therapy if the concentration of the one or more biomarkers in the biological sample is reduced, as compared to the concentration of the one or more biomarkers in a biological sample of the same type obtained from the patient prior to treatment with the complement inhibitor or determining that the patient has not responded to the therapy if the concentration of the one or more biomarkers in the biological sample is not reduced, as compared to the concentration of the one or more biomarkers in a biological sample of the same type obtained from the patient prior to treatment with the complement inhibitor. Thus, the method can be used to assess or monitor renal injury in an aHUS patient treated with a complement inhibitor. In embodiments in which the patient is non-responsive, or less responsive to therapy, the method can also include changing the dose amount or dose frequency of the complement inhibitor or electing a different complement inhibitor (e.g., an inhibitor of C3 activation) for use in treating the patient.

The inventors have also discovered that, in aHUS patients, the relative elevation of terminal complement activation markers C5a and sC5b-9 concentrations (e.g., urinary concentrations) are much higher than the relative elevation of levels of complement alternative pathway activation markers (e.g., Ba) in these patients. That is, the median concentration of C5a and sC5b-9 in aHUS patients was 45 and 305 fold higher, respectively, than the median concentration of these markers in normal healthy humans, whereas the median concentration of Ba was only approximately 5-fold higher than the median concentration of Ba in normal healthy humans. While not being bound by any particular theory or mechanism of action, the inventors believe that the ratio of terminal complement activation over alternative pathway activation is a useful diagnostic tool for aHUS. Thus, in another aspect, the disclosure features a method of diagnosing aHUS or confirming a diagnosis of aHUS, which method includes comparing the level of activation of terminal complement (e.g., sC5b-9 or C5a) to the level of activation of upstream alternative pathway activation (e.g., Ba or Bb) (relative to normal healthy humans), wherein a higher degree of terminal activation relative to the alternative pathway activation is an indication that the patient has aHUS. For example, a ratio indicative of aHUS could be, e.g., approximately 45:5 or 305:5, fold-induction of terminal complement activation to fold-induction alternative pathway activation. Moreover, the inventors believe that this ratio can be useful for distinguishing aHUS from other complement-associated diseases, such as, thrombotic thrombocytopenic purpura (TTP), which may not exhibit such a difference in terminal complement and upstream alternative pathway activation levels.

"Polypeptide," "peptide," and "protein" are used interchangeably and mean any peptide-linked chain of amino acids, regardless of length or post-translational modification. The proteins described herein can contain or be wild-type proteins or can be variants that have not more than 50 (e.g., not more than one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST software. Appropriate parameters for measuring alignment, including any algorithms needed to achieve maximal alignment over the full-length of the sequences being compared can be determined by known methods.

As used herein, the term "antibody" includes both whole antibodies and antigen-binding fragments of the whole antibodies. Whole antibodies include different antibody isotypes including IgM, IgG, IgA, IgD, and IgE antibodies. The term "antibody" includes a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be a purified or a recombinant antibody.

As used herein, the term "antibody fragment," "antigen-binding fragment," or similar terms refer to a fragment of an antibody that retains the ability to bind to a target antigen (e.g., human C5) and inhibit the activity of the target antigen. Such fragments include, e.g., a single chain antibody, a single chain Fv fragment (scFv), an Fd fragment, an Fab fragment, an Fab' fragment, or an F(ab')$_2$ fragment. An scFv fragment is a single polypeptide chain that includes both the heavy and light chain variable regions of the antibody from which the scFv is derived. In addition, intrabodies, minibodies, triabodies, and diabodies are also included in the definition of antibody and are compatible for use in the methods described herein. See, e.g., Todorovska et al. (2001) *J Immunol Methods* 248(1):47-66; Hudson and Kortt (1999) *J Immunol Methods* 231(1):177-189; Poljak (1994) *Structure* 2(12):1121-1123; and Rondon and Marasco (1997) *Annual Review of Microbiology* 51:257-283, the disclosures of each of which are incorporated herein by reference in their entirety. Bispecific antibodies (including DVD-Ig antibodies; see below) are also embraced by the term "antibody." Bispecific antibodies are monoclonal, preferably human or humanized, antibodies that have binding specificities for at least two different antigens.

As used herein, the term "antibody" also includes, e.g., single domain antibodies such as camelized single domain antibodies. See, e.g., Muyldermans et al. (2001) *Trends Biochem Sci* 26:230-235; Nuttall et al. (2000) *Curr Pharm Biotech* 1:253-263; Riechmann et al. (1999) *J Immunol Meth* 231:25-38; PCT application publication nos. WO 94/04678 and WO 94/25591; and U.S. Pat. No. 6,005,079, all of which are incorporated herein by reference in their entireties. In some embodiments, the disclosure provides single domain antibodies comprising two VH domains with modifications such that single domain antibodies are formed.

Unless otherwise defined, all technical and scientific terms used herein have the same meaning as commonly understood by one of ordinary skill in the art to which this disclosure pertains. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for treating complement-associated disorders in a subject, will be apparent from the following description, the examples, and from the claims.

BRIEF DESCRIPTION OF THE DRAWINGS

FIG. 1A is a dot plot depicting the concentration of C5a (in ng/mg of urinary creatine) in the urine of aHUS patients both before treatment with eculizumab (Pre-Tx) and various weeks after initiating treatment with eculizumab. The concentration of urinary C5a was also measured in the urine from normal, healthy individuals (NORM).

FIG. 1D is a bar graph depicting the mean percentage (%) reduction in urinary C5a levels (Y-axis) over time in aHUS patients (N=26) post initiation of treatment with eculizumab. The x-axis indicates the week of the aHUS patient visit for evaluation post-initiation of treatment, e.g., V3 is the patient visit for evaluation at week 3 post-initiation of treatment.

FIG. 1E is a bar graph depicting the mean percentage (%) reduction in urinary sC5b-9 levels (Y-axis) over time in aHUS patients (N=23) post initiation of treatment with eculizumab. The x-axis indicates the week of the aHUS patient visit for evaluation post-initiation of treatment, e.g., V3 is the patient visit for evaluation at week 3 post-initiation of treatment.

FIG. 1F is a bar graph depicting the mean percentage (%) reduction in plasma Ba levels (Y-axis) over time in aHUS patients (N=35) post initiation of treatment with eculizumab. The x-axis indicates the week of the aHUS patient visit for evaluation post-initiation of treatment, e.g., V3 is the patient visit for evaluation at week 3 post-initiation of treatment.

FIG. 6C is a bar graph depicting the mean percentage (%) reduction in plasma thrombomodulin levels (Y-axis) over time in aHUS patients (N=33) post initiation of treatment with eculizumab. The x-axis indicates the week of the aHUS patient visit for evaluation post-initiation of treatment, e.g., V3 is the patient visit for evaluation at week 3 post-initiation of treatment.

FIG. 6D is a bar graph depicting the mean percentage (%) reduction in serum VCAM-1 levels (Y-axis) over time in aHUS patients (N=36) post initiation of treatment with eculizumab. The x-axis indicates the week of the aHUS patient visit for evaluation post-initiation of treatment, e.g., V3 is the patient visit for evaluation at week 3 post-initiation of treatment.

FIGS. 9A-9E are a series of bar graphs depicting the mean levels of several aHUS biomarker proteins in aHUS patients that were subjected to dialysis (Dialysis), as compared to those aHUS patients that were not subjected to dialysis (no Dialysis) prior to enrollment in the study described herein. FIG. 9A depicts the mean concentration of serum TNFR1 (in pg/mL); FIG. 9B depicts the mean concentration of urinary β2M (in µg/mg of urinary creatine); FIG. 9C depicts the concentration of plasma Ba (in ng/mL); FIG. 9D depicts the concentration of urinary sC5b9 (in ng/mg of urinary creatine); and FIG. 9E depicts the concentration of urinary C5a (in ng/mL).

FIGS. 10B-10E are a series of bar graphs, each one depicting the concentration of a given biomarker in patients with normal hematologic markers LDH and haptoglobin ("normal patients" or patients deemed to be in clinical remission), patients with abnormal (elevated) hematologic markers ("abnormal patients" or patients with active aHUS presentation), and healthy subjects ("normals"). FIG. 10B depicts the levels of plasma Ba (ng/mL) in these subject populations. FIG. 10C depicts the level of serum VCAM-1 (ng/mL) in the subject populations. FIG. 10E depicts the level of plasma prothrombin fragments 1+2 (pmol/L) in the populations, and FIG. 10D depicts the level of plasma D-dimer (in µg/L). The P values for the respective group comparisons are shown in the figures.

FIGS. 10E-10I are a series of bar graphs, each one depicting the concentration of a given biomarker in patients with normal platelet levels ("normal patients"), patients with abnormal (reduced) platelet levels ("abnormal patients"), and healthy subjects ("normals"). FIG. 10F depicts the levels of plasma Ba (ng/mL) in these subject populations. FIG. 10G depicts the level of serum VCAM-1 (ng/mL) in the subject populations. FIG. 10I depicts the level of plasma prothrombin fragments 1+2 (pmol/L) in the populations, and FIG. 10H depicts the level of plasma D-dimer (in µg/L). The P values for the respective group comparisons are shown in the figures.

FIG. 14A depicts the concentration of cystatin C (CysC) (in ng/mg of urinary creatine) in the urine of aHUS patients with normal platelet counts (>150,000 per µL of blood) as compared to patients with reduced platelet counts (<150,000 per µL of blood). FIG. 14B depicts the concentration of clusterin (in ng/mg of urinary creatine) in the urine of aHUS patients with normal platelet counts (>150,000 per µL of blood) as compared to patients with reduced platelet counts (<150,000 per µL of blood). FIG. 14C depicts the concentration of VCAM-1 in the serum of aHUS patients with normal LDH levels as compared to patients with elevated LDH levels. FIG. 14D depicts the concentration of d-dimer (in µg/L) in the plasma of aHUS patients with normal LDH levels as compared to patients with elevated LDH levels. The p values for each observation are indicated in the figures.

FIGS. 17A-E are a series of bar graphs depicting the observation that certain aHUS-associated biomarkers are elevated in aHUS patients prior to treatment with a complement inhibitor, regardless of whether the patients have received plasma exchange (PE) or plasma infusion (PI) therapy. FIG. 17A depicts the concentration of Factor B proteolytic fragment Ba (in ng/mL) in the plasma of normal healthy volunteers (NHV), aHUS patients receiving PE or PI therapy (PE/PI), or aHUS patients not receiving PE/PI therapy (no PE/PI). FIG. 17B depicts the concentration of sTNFR1 (in pg/mL) in the serum of normal healthy volunteers (NHV), aHUS patients receiving PE or PI therapy (PE/PI), or aHUS patients not receiving PE/PI therapy (no PE/PI). FIG. 17C depicts the concentration of sVCAM-1 (in ng/mL) in the serum of normal healthy volunteers (NHV), aHUS patients receiving PE or PI therapy (PE/PI), or aHUS patients not receiving PE/PI therapy (no PE/PI). FIG. 17D depicts the concentration of D-dimer (in µg/L) in the plasma of normal healthy volunteers (NHV), aHUS patients receiving PE or PI therapy (PE/PI), or aHUS patients not receiving PE/PI therapy (no PE/PI). FIG. 17E depicts the concentration of cystatin-C (in ng/mg of urinary creatinine) in the urine of normal healthy volunteers (NHV), aHUS patients receiving PE or PI therapy (PE/PI), or aHUS patients not receiving PE/PI therapy (no PE/PI). The p values for each observation are indicated in the figures.

FIGS. 18A-E are a series of bar graphs depicting the observation that certain aHUS-associated biomarkers are elevated in aHUS patients prior to treatment with a complement inhibitor, regardless of platelet levels in the patients. FIG. 18A depicts the concentration of Factor B proteolytic fragment Ba (in ng/mL) in the plasma of normal healthy volunteers (NHV), aHUS patients having normal platelet levels (>150×10$^9$), or aHUS patients having reduced platelet counts (<150×10⁹). FIG. 18B depicts the concentration of sTNFR1 (in pg/mL) in the serum of normal healthy volunteers (NHV), aHUS patients having normal platelet levels (>150×10⁹), or aHUS patients having reduced platelet counts (<150×10⁹). FIG. 18C depicts the concentration of sVCAM-1 (in ng/mL) in the serum of normal healthy volunteers (NHV), aHUS patients having normal platelet levels (>150×10⁹), or aHUS patients having reduced platelet counts (<150×10⁹). FIG. 18D depicts the concentration of D-dimer (in μg/L) in the plasma of normal healthy volunteers (NHV), aHUS patients having normal platelet levels (>150×10⁹), or aHUS patients having reduced platelet counts (<150×10⁹). FIG. 18E depicts the concentration of cystatin-C (in ng/mg of urinary creatinine) in the urine of normal healthy volunteers (NHV), aHUS patients having normal platelet levels (>150×10⁹), or aHUS patients having reduced platelet counts (<150×10⁹). The p values for each observation are indicated in the figures.

FIGS. 19A-E are a series of bar graphs depicting the observation that certain aHUS-associated biomarkers are elevated in aHUS patients prior to treatment with a complement inhibitor, regardless of haptoglobin (Hp) or lactate dehydrogenase (LDH) levels. FIG. 19A depicts the concentration of Factor B proteolytic fragment Ba (in ng/mL) in the plasma of normal healthy volunteers (NHV), aHUS patients having normal Hp and LDH levels, or aHUS patients having elevated (abnormal) Hp/LDH. FIG. 19B depicts the concentration of sTNFR1 (in pg/mL) in the serum of normal healthy volunteers (NHV), aHUS patients having normal Hp and LDH levels, or aHUS patients having elevated (abnormal) Hp/LDH. FIG. 19C depicts the concentration of sVCAM-1 (in ng/mL) in the serum of normal healthy volunteers (NHV), aHUS patients having normal Hp and LDH levels, or aHUS patients having elevated (abnormal) Hp/LDH. FIG. 19D depicts the concentration of D-dimer (in μg/L) in the plasma of normal healthy volunteers (NHV), aHUS patients having normal Hp and LDH levels, or aHUS patients having elevated (abnormal) Hp/LDH. FIG. 19E depicts the concentration of cystatin-C (in ng/mg of urinary creatinine) in the urine of normal healthy volunteers (NHV), aHUS patients having normal Hp and LDH levels, or aHUS patients having elevated (abnormal) Hp/LDH. The p values for each observation are indicated in the figures.

FIG. 20A depicts the change over time in the concentration of urinary C5a (ng/mg of urinary creatinine) of aHUS patients following eculizumab treatment, as compared to the concentration of urinary C5a in the urine of normal healthy volunteers (NHV). FIG. 20B depicts the change over time in the concentration of urinary sC5b-9 (ng/mg of urinary creatinine) of aHUS patients following eculizumab treatment, as compared to the concentration of urinary sC5b-9 in the urine of normal healthy volunteers (NHV). The Box-Whisker plots show median, $25^{Th}$, and $75^{th}$ percentiles and range. *First time point at which levels were significantly reduced vs. baseline (BL); P values versus baseline at each timepoint were calculated using a restricted maximum likelihood-based repeated measures approach (Mixed Model). P values compared with NHV were calculated using the Wilcoxon Rank Sum test.

FIG. 20A depicts the change over time in the concentration of urinary FABP-1 (ng/mg of urinary creatinine) of aHUS patients following eculizumab treatment, as compared to the concentration of urinary FABP-1 in the urine of normal healthy volunteers (NHV). FIG. 21B depicts the change over time in the concentration of urinary cystatin-C (ng/mg of urinary creatinine) of aHUS patients following eculizumab treatment, as compared to the concentration of urinary cystatin-C in the urine of normal healthy volunteers (NHV). FIG. 21C depicts the change over time in the concentration of urinary clusterin (ng/mg of urinary creatinine) of aHUS patients following eculizumab treatment, as compared to the concentration of urinary clusterin in the urine of normal healthy volunteers (NHV). The Box-Whisker plots show median, $25^{Th}$, and $75^{th}$ percentiles and range. *First time point at which levels were significantly reduced vs. baseline (BL); P values versus baseline at each timepoint were calculated using a restricted maximum likelihood-based repeated measures approach (Mixed Model). P values compared with NHV were calculated using the Wilcoxon Rank Sum test.

FIGS. 23A-C are Box-Whisker plots depicting the longitudinal effects of sustained eculizumab treatment on the concentration of biomarker proteins associated with inflammation, endothelial cell activation, and tissue damage in aHUS patients. FIG. 23A depicts the change over time in the concentration of sTNFR1 (pg/mL) in the serum of aHUS patients following eculizumab treatment, as compared to the concentration of sTNFR1 in the serum of normal healthy volunteers (NHV). FIG. 23B depicts the change over time in the concentration of sVCAM-1 (ng/mL) in the serum of aHUS patients following eculizumab treatment, as compared to the concentration of the analyte in the serum of normal healthy volunteers (NHV). FIG. 23C depicts the change over time in the concentration of thrombomodulin (ng/mL) in the plasma of aHUS patients following eculizumab treatment, as compared to the concentration of the analyte in the plasma of normal healthy volunteers (NHV). The Box-Whisker plots show median, $25^{Th}$, and $75^{th}$ percentiles and range. *First time point at which levels were significantly reduced vs. baseline (BL); P values versus baseline at each timepoint were calculated using a restricted maximum likelihood-based repeated measures approach (Mixed Model). P values compared with NHV were calculated using the Wilcoxon Rank Sum test.

FIG. 24A depicts the change over time in the concentration of F1+2 (pmol/L) in the plasma of aHUS patients following eculizumab treatment, as compared to the concentration of the analyte in the plasma of normal healthy volunteers (NHV). FIG. 24B depicts the change over time in the concentration of D-dimer (μg/L) in the plasma of aHUS patients following eculizumab treatment, as compared to the concentration of the analyte in the plasma of normal healthy volunteers (NHV). The Box-Whisker plots show median, $25^{Th}$, and $75^{th}$ percentiles and range. *First time point at which levels were significantly reduced vs. baseline (BL); P values versus baseline at each timepoint were calculated using a restricted maximum likelihood-based repeated measures approach (Mixed Model). P values compared with NHV were calculated using the Wilcoxon Rank Sum test.

OVERVIEW OF THE COMPLEMENT SYSTEM

Figure 1B:
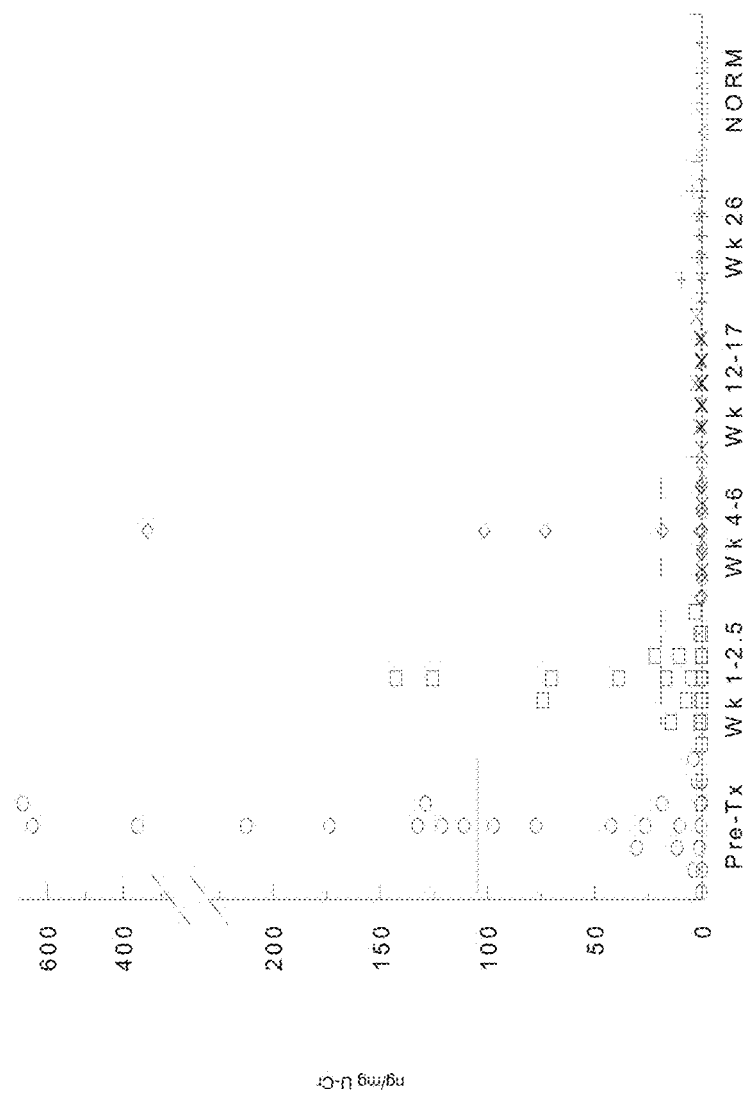
FIG. 1B is a dot plot depicting the concentration of sC5b-9 (in ng/mg of urinary creatine) in the urine of aHUS patients both before treatment with eculizumab (Pre-Tx) and various weeks after initiating treatment with eculizumab. The concentration of urinary C5b9 was also measured in the urine from normal, healthy individuals (NORM).

The complement system acts in conjunction with other immunological systems of the body to defend against intrusion of cellular and viral pathogens. There are at least 25 complement proteins, which are found as a complex collection of plasma proteins and membrane cofactors. The plasma proteins make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lytic functions. A concise summary of the biologic activities associated with complement activation is provided, for example, in The Merck Manual, $16^{th}$ Edition.

The complement cascade progresses via the classical pathway, the alternative pathway, or the lectin pathway. These pathways share many components, and while they differ in their initial steps, they converge and share the same "terminal complement" components (C5 through C9) responsible for the activation and destruction of target cells.

The classical pathway (CP) is typically initiated by antibody recognition of, and binding to, an antigenic site on a target cell. The alternative pathway (AP) can be antibody independent, and can be initiated by certain molecules on pathogen surfaces. Additionally, the lectin pathway is typically initiated with binding of mannose-binding lectin (MBL) to high mannose substrates. These pathways converge at the point where complement component C3 is cleaved by an active protease to yield C3a and C3b. Other pathways activating complement attack can act later in the sequence of events leading to various aspects of complement function. C3a is an anaphylatoxin. C3b binds to bacterial and other cells, as well as to certain viruses and immune complexes, and tags them for removal from the circulation. This opsonic function of C3b is generally considered to be the most important anti-infective action of the complement system. C3b also forms a complex with other components unique to each pathway to form classical or alternative C5 convertase, which cleaves complement component C5 (hereinafter referred to as "C5") into C5a and C5b.

Cleavage of C5 releases biologically active species such as for example C5a, a potent anaphylatoxin and chemotactic factor, and C5b which through a series of protein interactions leads to the formation of the lytic terminal complement complex, C5b-9. C5a and C5b-9 also have pleiotropic cell activating properties, by amplifying the release of downstream inflammatory factors, such as hydrolytic enzymes, reactive oxygen species, arachidonic acid metabolites and various cytokines.

C5b combines with C6, C7, and C8 to form the C5b-8 complex at the surface of the target cell. Upon binding of several C9 molecules, the membrane attack complex (MAC, C5b-9, terminal complement complex—TCC) is formed. When sufficient numbers of MACs insert into target cell membranes the openings they create (MAC pores) mediate rapid osmotic lysis of the target cells. Lower, non-lytic concentrations of MACs can produce other effects. In particular, membrane insertion of small numbers of the C5b-9 complexes into endothelial cells and platelets can cause deleterious cell activation. In some cases activation may precede cell lysis.

As mentioned above, C3a and C5a are activated complement components. These can trigger mast cell degranulation, which releases histamine from basophils and mast cells, and other mediators of inflammation, resulting in smooth muscle contraction, increased vascular permeability, leukocyte activation, and other inflammatory phenomena including cellular proliferation resulting in hypercellularity. C5a also functions as a chemotactic peptide that serves to attract pro-inflammatory granulocytes to the site of complement activation. C5a receptors are found on the surfaces of bronchial and alveolar epithelial cells and bronchial smooth muscle cells. C5a receptors have also been found on eosinophils, mast cells, monocytes, neutrophils, and activated lymphocytes.

DETAILED DESCRIPTION

As described herein and exemplified in the working Examples, the inventors identified biomarkers for aHUS. For example, it has been discovered that an elevated or, in some cases, reduced concentration of certain proteins is associated with the presence of aHUS. Similarly, a reduced or elevated concentration (or activity) of certain proteins in a biological fluid obtained from an aHUS patient treated with a complement inhibitor indicates that the patient has responded to therapy with the inhibitor. Accordingly, analysis of the concentration and/or activity level of such proteins can be employed to evaluate, among other things, risk for aHUS, diagnose aHUS, monitor progression or abatement of aHUS, and/or monitor treatment response to a complement inhibitor.

aHUS Biomarker Proteins and Applications aHUS biomarker proteins (as well as exemplary biological fluids in which they are found) are set forth in Table 1. The protein sequence associated with the name of each of the biomarkers listed in Table 1 in GenBank (National Center for Biotechnology Information (NCBI)) as available as of the filing date of the present application are incorporated herein by reference.

TABLE 1

| Biomarker | Abbr. | Serum | Plasma | Urine | NCBI Reference Seq no.* |
|---|---|---|---|---|---|
| Markers of Inflammation/platelet or endothelial activation ||||||
| Chemokine (C-X-C motif) ligand 9 | CXCL9 | X | | | NP_002407.1 |
| Chemokine (C-X-C motif) ligand 10 | CXCL-10 | X | | | NP_001556.2 |
| Interleukin-1 beta | IL-1β | X | | | NP_000567.1 |
| Interleukin-6 | IL-6 | X | | | NP_000591.1 |
| Interleukin-8 | IL-8 | X | | | NP_000575.1 |
| Interleukin-12 p70 | IL-12p70 | X | | | NP_000873.2 (p35) NP_002178.2 (p40) |
| Interferon-gamma | IFN-γ | X | | | NP_000610.2 |
| platelet-selectin | p-selectin | X | | | NP_002996.2 |
| endothelial-selectin | e-selectin | X | | | NP_000441.2 |
| Intercellular Adhesion Molecule-1 | ICAM-1 | X | | | NP_000192.2 |

TABLE 1-continued

| Biomarker | Abbr. | Tissue Source | | | NCBI Reference Seq no.* |
|---|---|---|---|---|---|
| | | Serum | Plasma | Urine | |
| Vascular cell adhesion molecule-1 | VCAM-1 | X | | | NP_001069.1 |
| Monocyte chemotactic protein-1 | MCP-1 | X | | | NP_002973.1 |
| Vascular endothelial growth factor | VEGF | X | | | NP_001020537.2 |
| Regulated on Activation, Normal T cell Expressed and Secreted (CCL5) | CCL5 | X | | | NP_002976.2 |
| Soluble CD40 ligand | sCD40L | X | | | NP_000065.1** |
| Soluble Tumor necrosis factor receptor 1 | sTNFR1 | X | | | NP_001056.1** |
| Interleukin-18 | IL-18 | X | | | NP_001553.1 |
| Markers of Inflammation/Renal Injury | | | | | |
| neutrophil gelatinase-associated lipocalin | NGAL | | | X | NP_005555.2 |
| Kidney injury molecule-1 | KIM-1 | | | X | NP_001092884.1 |
| Osteopontin | OPN | | | X | NP_001035147.1 |
| tissue inhibitor of metalloproteinases-1 | TIMP-1 | | | X | NP_003245.1 |
| Interleukin-18 | IL-18 | | | X | Supra |
| Chemokine (C-X-C motif) ligand 9 | CXCL9 | | | X | Supra |
| Chemokine (C-X-C motif) ligand 10 | CXCL10 | | | X | Supra |
| clusterin | CLU | | | X | NP_001822.3 |
| Cystatin C | CyC | | | X | NP_000090.1 |
| albumin | ALB | | | X | NP_000468.1 |
| Liver-fatty acid binding protein | L-FABP | | | X | NP_001434.1 |
| Beta-2-microglobulin | β2M | | | X | NP_004039.1 |
| Trefoil factor 3 | TFF-3 | | | X | NP_003217.3 |
| N-acetyl-beta-D-glucosaminidase | NAG | | | X | NP_000511.2 |
| π-glutathione S-transferase | π-GST | | | X | NP_000843.1 |
| Alpha-glutathione S-transferase | α-GST | | | X | NP_665683.1 |
| Complement | | | | | |
| Complement Ba | Ba | | X | | SEQ ID NO: 1; See also FIG. 2 of Morley and Campbell (1984) EMBO J 3(1):153-157. |
| Complement C3a | C3a | | X | | SEQ ID NO: 2 |
| Complement C5a | C5a | | X | X | SEQ ID NO: 3 |
| Soluble MAC | sC5b9 | | X | X | NA |
| CH50 (hemolysis) | CH50 | X | | | NA |
| Complement C5 | C5 | X | X | | NP_001726.2 |
| Thrombosis/coagulation | | | | | |
| D-dimer | D-dimer | | X | | P02671*** |
| Prothrombin F1 + 2 | F1 + 2 | | X | | Activation fragment 1 (SEQ ID NO: 4) corresponds to amino acids 44-198 of SEQ ID NO: 6. Activation fragment 2 (SEQ ID NO: 5) corresponds to amino acids 199-327 of SEQ ID NO: 4. |
| Von Willebrand factor | vWF | | X | | NP_000543.2 |
| Von Willebrand factor activity | vWF activity | | X | | Id. |
| Thrombomodulin | TM | | X | | NP_000352.1 |

*The NCBI accession number for an exemplary human sequence is provided for each biomarker protein recited in the Table.
**The soluble form of the receptor is generated by proteolytic processing of the membrane bound form of the receptor.
***UniProtKB (consortium: European Bioinformatics Institute, Cambridge, UK; Swiss Institute of Bioinformatics; Geneva, Switzerland; and Protein Information Resource, Washington, D.C.) designation for human fibrinogen alpha, which is cleaved by thrombin to form fibrin. D-dimer is a degradation product of fibrin. A description of the cleavage-based transition of fibrinogen to fibrin to D-dimer is set forth in Soheir et al. (2009) *Blood* 113(13):2878-2887, the disclosure of which at least as it relates to the formation of D-dimer is incorporated herein in its entirety.

Biomarkers provided herein can be used alone or in combination as an indicator to, e.g., evaluate risk for developing aHUS, diagnosing aHUS, determining whether a subject is experiencing the first acute presentation of aHUS, monitoring progression or abatement of aHUS, and/or monitoring response to treatment with a complement inhibitor or optimizing such treatment. In some embodiments, an individual aHUS biomarker protein described herein may be used. In some embodiments, at least two, three, four, five, six, seven, eight, nine, 10, 11, 12, 13, 14, 15, 16, 17, 18, 19, 20, 21, 22, 23, 24, or 25 or more) aHUS biomarker proteins selected from Table 1 may be used in combination as a panel.

In some embodiments, the aHUS biomarker proteins are selected from a proteolytic fragment of complement component factor B (e.g., Ba or Bb), soluble C5b9 (sC5b9), thrombomodulin, VCAM-1, von Willebrand Factor (vWF), soluble CD40 ligand (sCD40L), prothrombin fragment F1+2, D-dimer, CXCL10, MCP-1, TNFR1, IFN-γ, ICAM-1, IL-1 beta, IL-12 p70, complement component C5a, β2 microglobulin (β2M), clusterin, cystatin C, NAG, TIMP-1, NGAL, fatty acid binding protein 1 (FABP-1), CXCL9, KIM-1, IL-18, vascular endothelial cell growth factor (VEGF), IL-6, albumin, IL-8, and CCL5. The concentration and/or activity of one or more of the biomarkers in Table 1 (or any of the subsets of biomarkers mentioned herein) can be measured.

In some embodiments, an elevation in the d-dimer concentration, relative to the concentration of d-dimer in a normal control sample, and an elevation in the FABP-1 concentration, relative to the concentration of FABP-1 in a normal control sample, indicates that the aHUS patient is experiencing a first acute aHUS manifestation. In some instances, that elevation of one or both of these aHUS biomarker proteins is a significant elevation as compared to the normal control.

In some embodiments, an elevation in the concentration of one or more of TNFR1, Ba, C5b-9, F1+2, β2M, clusterin, TIMP-1, NGAL, CysC, and C5a (see Table 7) in a biological sample obtained from an aHUS patient, relative to the control concentration of the analytes obtained, e.g., from a pool of samples from aHUS patients who have not received repeated dialysis, indicates that the patient is one who has received repeated dialysis.

In some embodiments, an elevation in the concentration of one or both of C5a and FABP-1 (e.g., urinary C5a and FABP-1) in a biological sample obtained from an aHUS patient, relative to the control concentration of the analytes obtained, e.g., from a pool of samples from aHUS patients who have not received a kidney transplant, indicates that the patient is one who has received a kidney transplant.

In some embodiments, an elevation in the concentration of cystatin C (e.g., urinary cystatin C) in a biological sample obtained from an aHUS patient, relative to the control concentration of the analytes obtained, e.g., from a pool of samples from aHUS patients who have not received repeated plasma therapy, indicates that the patient is one who has received repeated plasma therapy.

In some embodiments, a post-treatment reduction in Ba concentration (e.g., plasma Ba concentration) of at least 10 (e.g., at least 15, 20, 25, 30, 35, 40, 45, or 50) %, relative to the Ba concentration in a sample of the same type of biological fluid obtained from the subject prior to treatment, indicates that the subject has or is likely to achieve a complete thrombomicroangiopathy (TMA) response (i.e., cessation of TMA events). In some embodiments, the reduction occurs by week 12 following the first treatment with the complement inhibitor. In some embodiments, the reduction occurs within weeks 12-17 following the first treatment with the complement inhibitor. In some embodiments, the reduction occurs by week 26 following the first treatment with the complement inhibitor.

In some embodiments, a post-treatment reduction in one or both of CCL5 and sCD40L of at least 10 (e.g., at least 15, 20, 25, 30, 35, 40, 45, or 50) %, relative to the respective concentration in sample(s) of the same type of biological fluid obtained from the subject prior to treatment, indicates that the subject has or is likely to achieve increased platelet counts (e.g., platelet recovery). In some embodiments, a post-treatment reduction in Ba concentration (e.g., plasma Ba concentration) of at least 10 (e.g., at least 15, 20, 25, 30, 35, 40, 45, or 50) % (or normalization of Ba concentrations), relative to the Ba concentration in a sample of the same type of biological fluid obtained from the subject prior to treatment, indicates that the subject has or is likely to have achieved a complete thrombomicroangiopathy (TMA) response (i.e., cessation of TMA events).

In some embodiments, the status of one or more of the aHUS biomarkers described herein can be predictive of improvement in the estimated glomerular filtration rate (eGFR) for an aHUS patient treated with a complement inhibitor. For example, a reduction in the concentration of prothrombin F1+2 (e.g., within 4, 5, or 6 weeks post initial treatment in a chronic treatment regimen) and/or d-dimer (e.g., within 12, 13, 14, 15, 16, or 17 weeks post initial treatment in a chronic treatment regimen) indicates that an aHUS patient treated with a complement inhibitor has achieved or is likely to achieve a clinically meaningful improvement in eGFR. Achievement or likely achievement of a clinically meaningful improvement in eGFR is also indicated by a normalization of IL-6 and IFN-γ concentration (e.g., within 4, 5, or 6 weeks post initial treatment with a complement inhibitor in a chronic treatment regimen). Achievement or likely achievement of a clinically meaningful improvement in eGFR is also indicated by a normalization of Ba, CXCL9, CXCL10, and vWF concentration (e.g., within 12, 13, 14, 15, 16, or 17 weeks post initial treatment with a complement inhibitor in a chronic treatment regimen). In some embodiments, achievement or likely achievement of a clinically meaningful improvement in eGFR is also indicated by a normalization of Ba, CXCL9, CXCL10, β2M (e.g., in urine), CysC (e.g., in urine), vWF, d-dimer, clusterin (e.g., in urine), and/or FABP-1 (e.g., in urine) concentration (e.g., within 26 weeks post initial treatment with a complement inhibitor in a chronic treatment regimen).

Methods for monitoring or evaluating the status of one or more atypical hemolytic uremic syndrome (aHUS)-associated biomarker proteins in a subject (e.g., a mammal, e.g., a human) include: measuring in a biological fluid obtained from the subject one or both of (i) the concentration of at least one (e.g., at least two, three, four, five, six, seven, eight, nine, 10, 11, 12, 13, 14, 15, 16, 17, 18, 19, or 20) aHUS-associated biomarker protein in the biological fluid.

Measuring or determining protein expression levels in a biological sample may be performed by any suitable method (see, e.g., Harlow and Lane (1988) "Antibodies: A Laboratory Manual", Cold Spring Harbor Laboratory: Cold Spring Harbor, N.Y.). In general, protein levels are determined by contacting a biological sample obtained from a subject with binding agents for one or more of the aHUS biomarker proteins; detecting, in the sample (e.g., the biological fluid), the levels of one or more of the aHUS biomarker proteins that bind to the binding agents; and comparing the levels of one or more of the aHUS biomarker proteins in the sample with the levels of the corresponding protein biomarkers in a control sample (e.g., a normal sample). In certain embodiments, a suitable binding agent is a ribosome, with or without a peptide component, an RNA molecule, or a polypeptide (e.g., a polypeptide that comprises a polypeptide sequence of a protein marker, a peptide variant thereof, or a non-peptide mimetic of such a sequence).

Suitable binding agents also include an antibody specific for an aHUS biomarker protein described herein (e.g., an antibody specific for any biomarker listed in Table 1). Suitable antibodies for use in the methods of the present invention include monoclonal and polyclonal antibodies and antigen-binding fragments (e.g., Fab fragments or scFvs) of antibodies. Antibodies, including monoclonal and polyclonal antibodies, fragments and chimeras, may be prepared using methods known in the art (see, for example, Kohler and Milstein (1975) *Nature* 256:495-497; Kozbor et al. (1985) *J Immunol Methods* 81:31-42; Cote et al. (1983) *Proc Natl Acad Sci USA* 80:2026-203; and Zhang et al. (2002) *J Biol Chem* 277:39379-39387). Antibodies to be used in the methods of the invention can be purified by methods well known in the art. Antibodies may also be obtained from commercial sources.

In certain embodiments, the binding agent is directly or indirectly labeled with a detectable moiety. The role of a detectable agent is to facilitate the detection step of the diagnostic method by allowing visualization of the complex formed by binding of the binding agent to the protein marker (or fragment thereof). The detectable agent can be selected such that it generates a signal that can be measured and whose intensity is related (preferably proportional) to the amount of protein marker present in the sample being analyzed. Methods for labeling biological molecules such as polypeptides and antibodies are well-known in the art. Any of a wide variety of detectable agents can be used in the practice of the present invention. Suitable detectable agents include, but are not limited to: various ligands, radionuclides, fluorescent dyes, chemiluminescent agents, microparticles (such as, for example, quantum dots, nanocrystals, phosphors and the like), enzymes (such as, e.g., those used in an ELISA, i.e., horseradish peroxidase, beta-galactosidase, luciferase, alkaline phosphatase), colorimetric labels, magnetic labels, and biotin, digoxigenin or other haptens and proteins for which antisera or monoclonal antibodies are available.

In certain embodiments, the binding agents (e.g., antibodies) may be immobilized on a carrier or support (e.g., a bead, a magnetic particle, a latex particle, a microtiter plate well, a cuvette, or other reaction vessel). Examples of suitable carrier or support materials include agarose, cellulose, nitrocellulose, dextran, Sephadex®, Sepharose®, liposomes, carboxymethyl cellulose, polyacrylamides, polystyrene, gabbros, filter paper, magnetite, ion-exchange resin, plastic film, plastic tube, glass, polyamine-methyl vinyl-ether-maleic acid copolymer, amino acid copolymer, ethylene-maleic acid copolymer, nylon, silk, and the like. Binding agents may be indirectly immobilized using second binding agents specific for the first binding agents (e.g., mouse antibodies specific for the protein markers may be immobilized using sheep anti-mouse IgG Fc fragment specific antibody coated on the carrier or support).

Protein expression levels in a biological sample may be determined using immunoassays. Examples of such assays are time resolved fluorescence immunoassays (TR-FIA), radioimmunoa says, enzyme immunoassays (e.g., ELISA), immunofluorescence immunoprecipitation, latex agglutination, hemagglutination, Western blot, and histochemical tests, which are conventional methods well-known in the art. Methods of detection and quantification of the signal generated by the complex formed by binding of the binding agent with the protein marker will depend on the nature of the assay and of the detectable moiety (e.g., fluorescent moiety).

In one example, the presence or amount of protein expression of a gene (e.g., an aHUS biomarker protein depicted in Table 1) can be determined using a Western blotting technique. For example, a lysate can be prepared from a biological sample, or the biological sample (e.g., biological fluid) itself, can be contacted with Laemmli buffer and subjected to sodium-dodecyl sulfate polyacrylamide gel electrophoresis (SDS-PAGE). SDS-PAGE-resolved proteins, separated by size, can then be transferred to a filter membrane (e.g., nitrocellulose) and subjected to immunoblotting techniques using a detectably-labeled antibody specific to the protein of interest. The presence or amount of bound detectably-labeled antibody indicates the presence or amount of protein in the biological sample.

In another example, an immunoassay can be used for detecting and/or measuring the protein expression of an aHUS biomarker protein (e.g., one depicted in Table 1). As above, for the purposes of detection, an immunoassay can be performed with an antibody that bears a detection moiety (e.g., a fluorescent agent or enzyme). Proteins from a biological sample can be conjugated directly to a solid-phase matrix (e.g., a multi-well assay plate, nitrocellulose, agarose, Sepharose®, encoded particles, or magnetic beads) or it can be conjugated to a first member of a specific binding pair (e.g., biotin or streptavidin) that attaches to a solid-phase matrix upon binding to a second member of the specific binding pair (e.g., streptavidin or biotin). Such attachment to a solid-phase matrix allows the proteins to be purified away from other interfering or irrelevant components of the biological sample prior to contact with the detection antibody and also allows for subsequent washing of unbound antibody. Here, as above, the presence or amount of bound detectably-labeled antibody indicates the presence or amount of protein in the biological sample.

Alternatively, the protein expression levels may be determined using mass spectrometry based methods or image-based methods known in the art for the detection of proteins. Other suitable methods include 2D-gel electrophoresis, proteomics-based methods such as the identification of individual proteins recovered from the gel (e.g., by mass spectrometry or N-terminal sequencing) and/or bioinformatics.

Methods for detecting or measuring protein expression can, optionally, be performed in formats that allow for rapid preparation, processing, and analysis of multiple samples. This can be, for example, in multi-well assay plates (e.g., 96 wells or 386 wells) or arrays (e.g., protein chips). Stock solutions for various reagents can be provided manually or robotically, and subsequent sample preparation, pipetting, diluting, mixing, distribution, washing, incubating (e.g., hybridization), sample readout, data collection (optical data) and/or analysis (computer aided image analysis) can be done robotically using commercially available analysis software, robotics, and detection instrumentation capable of detecting the signal generated from the assay. Examples of such detectors include, but are not limited to, spectrophotometers, luminometers, fluorimeters, and devices that measure radioisotope decay. Exemplary high-throughput cell-based assays (e.g., detecting the presence or level of a target protein in a cell) can utilize ArrayScan® VTI HCS Reader or Kinetic-Scan® HCS Reader technology (Cellomics Inc., Pittsburgh, Pa.).

Methods for determining the activity of vWF are also known in the art and described herein (e.g., the working examples). See also, e.g., Horvath et al. (2004) *Exp Clin Cardiol* 9(10):31-34. Commercial kits are also available—Instrumentation Laboratory (Bedford, Mass.; catalogue number: 0020004700) and Quest Diagnostics (Madison, N.J.).

In some embodiments, the protein expression level (or activity) of at least two aHUS biomarker proteins (e.g., at least three proteins, at least four proteins, at least five proteins, at least six proteins, at least seven proteins, at least eight proteins, at least nine proteins, at least 10 proteins, at least 11 proteins, at least 12 proteins, at least 13 proteins, at least 14 proteins, at least 15 proteins, at least 16 proteins, at least 17 proteins, at least 18 proteins, at least 19 proteins, at least 20 proteins, at least 21 proteins, at least 22 proteins, at least 23 proteins, or at least 24 proteins or more) can be assessed and/or measured.

In some embodiments, the biological fluid in which the aHUS biomarker proteins are measured is blood. In some embodiments, the biological fluid is a blood fraction, e.g., serum or plasma. In some embodiments, the biological fluid is urine. In some embodiments, all of the measurements are performed on one biological fluid sample (e.g., a serum sample). In some embodiments, measurements are performed on at least two different biological fluids obtained from the subject. For example, in some embodiments, the concentration or activity of one or more aHUS biomarker proteins is measured in a serum sample obtained from the patient. In some embodiments, a blood sample and a urine sample are available so as to allow for testing of different analytes in two different sample matrices.

The subject can be, e.g., a human having, suspected of having, or at risk for developing, aHUS. The subject can be one who has been (or is being) treated with an inhibitor of complement (e.g., an inhibitor of complement component C5 such as an anti-C5 antibody). The treatment can have occurred less than one month (e.g., less than 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 day) prior to obtaining the sample from the subject.

The method can further include the step of determining whether the subject has or is at risk of developing aHUS. Where the subject has been treated or is being treated with a complement inhibitor (e.g., an anti-C5 antibody) under a predetermined dosing schedule, the method can further include determining whether the patient is responsive (therapeutically) to the complement inhibitor therapy.

In some embodiments of any of the methods described herein, the method requires recording the measured value(s) of the concentration of the at least one aHUS biomarker protein. The recordation can be written or on a computer readable medium. The method can also include communicating the measured value(s) of the concentration of the at least one aHUS biomarker protein to the subject and/or to a medical practitioner in whose care the subject is placed.

In some embodiments, any of the methods described herein can include the step of administering to the subject the complement inhibitor at a higher dose or with an increased frequency of dosing, relative to the predetermined dosing schedule, if the subject is not responsive to treatment with the inhibitor under the predetermined dosing schedule.

Some of the methods described herein involve comparing the measured concentration or activity of an aHUS biomarker protein (as measured in a biological sample obtained from a subject) to a control sample. In some embodiments, control sample is obtained from the subject prior to administering to the subject a complement inhibitor (e.g., a C5 inhibitor such as eculizumab). In some embodiments, the control sample can be (or can be based on), e.g., a collection of samples obtained from one or more (e.g., two, three, four, five, six, seven, eight, nine, 10, 15, 20, 25, 30, 35, or 40 or more) healthy individuals that have not been administered a complement inhibitor. In some embodiments, the control sample can be (or can be based on), e.g., a pooled sample obtained from two or more (e.g., two, three, four, five, six, seven, eight, nine, 10, 15, 20, 25, 30, 35, or 40 or more) individuals. In some embodiments of any of the methods described herein, the pooled samples can be from healthy individuals, or at least, individuals who do not have or are not suspected of having (nor at risk for developing) aHUS. For example, determining whether a subject is one having aHUS can involve comparing the measured concentration of one or more serum biomarkers in the subject and comparing the measured concentration to the average concentration of the same biomarkers in the pooled healthy samples. Similarly, determining whether the concentration or activity of an aHUS associated biomarker has been reduced following treatment with a complement inhibitor can involve comparing the concentration or activity of the protein in a biological fluid obtained from a subject prior to treatment with a complement inhibitor to the concentration of protein in a sample of the same biological fluid obtained from the patient after treatment with the inhibitor (e.g., one day, two days, three days, four days, five days, six days, 1 week, 2 weeks, 3 weeks, a month, 6 weeks, two months, or three months after treatment (e.g., the first of a series of treatment in chronic therapy) with the inhibitor).

In some embodiments, determining whether a complement inhibitor has produced a desired effect (e.g., a reduction in the concentration or activity of an aHUS biomarker protein) in a human can be performed by querying whether the post-treatment concentration of the protein falls within a predetermined range indicative of responsiveness to a complement inhibitor by a human. In some embodiments, determining whether a complement inhibitor has produced a desired effect in a human can include querying if the post-treatment concentration or activity of one or more aHUS biomarker proteins falls above or below a predetermined cut-off value. A cut-off value is typically the concentration or activity of a given protein in a given biological fluid above or below which is considered indicative of a certain phenotype—e.g., responsiveness to therapy with a complement inhibitor.

In some embodiments of any of the methods described herein, the same practitioner may administer the complement inhibitor to the subject prior to determining whether a change in the concentration or activity of one or more aHUS biomarker proteins has occurred, whereas in some embodiments, the practitioner who administers the inhibitor to the subject is different from the practitioner who determines whether a response has occurred in the subject. In some embodiments, the practitioner may obtain a biological sample (e.g., the blood sample) from the subject prior to administration of the inhibitor. In some embodiments, the practitioner may obtain a biological sample (e.g., a blood sample) from the subject following the administration of the inhibitor to the subject. In some embodiments, the post-treatment sample can be obtained from the subject less than 48 (e.g., less than 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, nine, eight, seven, six, five, four, three, two, or even less than one) hour following administration of the inhibitor to the subject. In some embodiments, the post-treatment sample can be obtained from the subject less than 20 (e.g., less than 19, 18, 17, 16, 15, 14, 13, 12, 11, 10, nine, eight, seven, six, five, four, three, two, or one) day(s) after administering to the subject the inhibitor. In some embodiments, the biological sample is obtained from the subject no more than 20 (e.g., no more than 19, 18, 17, 16, 15, 14, 13, 12, 11, 10, nine, eight, seven, six, five, four, three, two, or one) day(s) after the inhibitor is administered to the subject.

In some embodiments, various steps of the methods described herein can be performed by more than one practitioner. For example, one practitioner may analyze (e.g., measure the concentration or activity of one or more aHUS biomarker proteins in) the pre- and post-treatment samples obtained from the subject. Another practitioner may receive information regarding the analysis of the samples by the first practitioner to thereby determine whether, e.g., the subject has responded to treatment with a complement inhibitor. In some embodiments, yet another practitioner may obtain a pre-treatment biological sample from a patient and a fourth practitioner may obtain a post-treatment biological sample from the subject. In some embodiments, all steps are carried out by the same practitioner.

Biological Samples and Sample Collection

Suitable biological samples for use in the methods described herein include, e.g., any biological fluid. A biological sample can be, for example, a specimen obtained from a subject (e.g., a mammal such as a human) or can be derived from such a subject. A biological sample can also be a biological fluid such as urine, whole blood or a fraction thereof (e.g., plasma or serum), saliva, semen, sputum, cerebrospinal fluid, tears, or mucus. A biological sample can be further fractionated, if desired, to a fraction containing particular analytes (e.g., proteins) of interest. For example, a whole blood sample can be fractionated into serum or into fractions containing particular types of proteins. If desired, a biological sample can be a combination of different biological samples from a subject such as a combination of two different fluids.

Biological samples suitable for the invention may be fresh or frozen samples collected from a subject, or archival samples with known diagnosis, treatment and/or outcome history. The biological samples can be obtained from a subject, e.g., a subject having, suspected of having, or at risk of developing, a complement-associated disorder such as aHUS. Any suitable methods for obtaining the biological samples can be employed, although exemplary methods include, e.g., phlebotomy, swab (e.g., buccal swab), lavage, or fine needle aspirate biopsy procedure. Biological samples can also be obtained from bone marrow.

In some embodiments, a protein extract may be prepared from a biological sample. In some embodiments, a protein extract contains the total protein content. Methods of protein extraction are well known in the art. See, e.g., Roe (2001) "Protein Purification Techniques: A Practical Approach", 2$^{nd}$ Edition, Oxford University Press. Numerous different and versatile kits can be used to extract proteins from bodily fluids and tissues, and are commercially available from, for example, BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, Ill.), and Invitrogen Corp. (Carlsbad, Calif.).

Methods for obtaining and/or storing samples that preserve the activity or integrity of cells in the biological sample are well known to those skilled in the art. For example, a biological sample can be further contacted with one or more additional agents such as appropriate buffers and/or inhibitors, including protease inhibitors, the agents meant to preserve or minimize changes (e.g., changes in osmolarity or pH) in protein structure. Such inhibitors include, for example, chelators such as ethylenediamine tetraacetic acid (EDTA), ethylene glycol tetraacetic acid (EGTA), protease inhibitors such as phenylmethylsulfonyl fluoride (PMSF), aprotinin, and leupeptin. Appropriate buffers and conditions for storing or otherwise manipulating whole cells are described in, e.g., Pollard and Walker (1997), "Basic Cell Culture Protocols," volume 75 of *Methods in molecular biology*, Humana Press; Masters (2000) "Animal cell culture: a practical approach," volume 232 of *Practical approach series*, Oxford University Press; and Jones (1996) "Human cell culture protocols," volume 2 of *Methods in molecular medicine*, Humana Press.

A sample also can be processed to eliminate or minimize the presence of interfering substances. For example, a biological sample can be fractionated or purified to remove one or more materials (e.g., cells) that are not of interest. Methods of fractionating or purifying a biological sample include, but are not limited to, flow cytometry, fluorescence activated cell sorting, and sedimentation.

Complement Inhibitors

Any compound which binds to and inhibits, or otherwise inhibits, the generation and/or activity of any of the human complement components may be utilized in accordance with the present disclosure. For example, an inhibitor of complement can be, e.g., a small molecule, a nucleic acid or nucleic acid analog, a peptidomimetic, or a macromolecule that is not a nucleic acid or a protein. These agents include, but are not limited to, small organic molecules, RNA aptamers, L-RNA aptamers, Spiegelmers, antisense compounds, double stranded RNA, small interfering RNA, locked nucleic acid inhibitors, and peptide nucleic acid inhibitors. In some embodiments, a complement inhibitor may be a protein or protein fragment.

In some embodiments, the compositions contain antibodies specific to a human complement component. Some compounds include antibodies directed against complement components C1, C2, C3, C4, C5, C6, C7, C8, C9, Factor D, Factor B, Factor P, MBL, MASP-1, MASP-2, properdin, or a biologically-active fragment of any of the foregoing, thus preventing the generation of the anaphylatoxic activity associated with C5a and/or preventing the assembly of the membrane attack complex C5b-9.

The compositions can also contain naturally occurring or soluble forms of complement inhibitory compounds such as CR1, LEX-CR1, MCP, DAF, CD59, Factor H, cobra venom factor, FUT-175, complestatin, and K76 COOH. Other compounds which may be utilized to bind to or otherwise block the generation and/or activity of any of the human complement components include, but are not limited to, proteins, protein fragments, peptides, small molecules, RNA aptamers including ARC187 (which is commercially available from Archemix Corporation, Cambridge, Mass.), L-RNA aptamers, spiegelmers, antisense compounds, serine protease inhibitors, molecules which may be utilized in RNA interference (RNAi) such as double stranded RNA including small interfering RNA (siRNA), locked nucleic acid (LNA) inhibitors, peptide nucleic acid (PNA) inhibitors, etc.

In some embodiments, the complement inhibitor inhibits the activation of complement. For example, the complement inhibitor can bind to and inhibit the complement activation activity of C1 (e.g., C1q, C1r, or C1s) or the complement inhibitor can bind to and inhibit (e.g., inhibit cleavage of) C2, C3, or C4. In some embodiments, the inhibitor inhibits formation or assembly of the C3 convertase and/or C5 convertase of the alternative and/or classical pathways of complement. In some embodiments, the complement inhibitor inhibits terminal complement formation, e.g., formation of the C5b-9 membrane attack complex. For example, an antibody complement inhibitor may include an anti-C5 antibody. Such anti-C5 antibodies may directly interact with C5 and/or C5b, so as to inhibit the formation of and/or physiologic function of C5b.

In some embodiments, the compositions described herein can contain an inhibitor of human complement component C5 (e.g., an antibody, or antigen-binding fragment thereof, that binds to a human complement component C5 protein or a biologically-active fragment thereof such as C5a or C5b). As used herein, an "inhibitor of complement component C5" is any agent that inhibits: (i) the expression, or proper intracellular trafficking or secretion by a cell, of a complement component C5 protein; (ii) the activity of C5 cleavage fragments C5a or C5b (e.g., the binding of C5a to its cognate cellular receptors or the binding of C5b to C6 and/or other components of the terminal complement complex; see above); (iii) the cleavage of a human C5 protein to form C5a and C5b; (iv) the proper intracellular trafficking of, or secretion by a cell, of a complement component C5 protein; or (v) the stability of C5 protein or the mRNA encoding C5 protein. Inhibition of complement component C5 protein expression includes: inhibition of transcription of a gene encoding a human C5 protein; increased degradation of an mRNA encoding a human C5 protein; inhibition of translation of an mRNA encoding a human C5 protein; increased degradation of a human C5 protein; inhibition of proper processing of a pre-pro human C5 protein; or inhibition of proper trafficking or secretion by a cell of a human C5 protein. Methods for determining whether a candidate agent is an inhibitor of human complement component C5 are known in the art and described herein.

An inhibitor of human complement component C5 can be, e.g., a small molecule, a polypeptide, a polypeptide analog, a nucleic acid, or a nucleic acid analog.

"Small molecule" as used herein, is meant to refer to an agent, which has a molecular weight preferably of less than about 6 kDa and most preferably less than about 2.5 kDa. Many pharmaceutical companies have extensive libraries of chemical and/or biological mixtures comprising arrays of small molecules, often fungal, bacterial, or algal extracts, which can be screened with any of the assays of the application. This application contemplates using, among other things, small chemical libraries, peptide libraries, or collections of natural products. Tan et al. described a library with over two million synthetic compounds that is compatible with miniaturized cell-based assays (*J Am Chem Soc* (1998) 120:8565-8566). It is within the scope of this application that such a library may be used to screen for agents that bind to a target antigen of interest (e.g., complement component C5). There are numerous commercially available compound libraries, such as the Chembridge DIVERSet. Libraries are also available from academic investigators, such as the Diversity set from the NCI developmental therapeutics program. Rational drug design may also be employed. For example, rational drug design can employ the use of crystal or solution structural information on the human complement component C5 protein. See, e.g., the structures described in Hagemann et al. (2008) *J Biol Chem* 283(12):7763-75 and Zuiderweg et al. (1989) *Biochemistry* 28(1):172-85. Rational drug design can also be achieved based on known compounds, e.g., a known inhibitor of C5 (e.g., an antibody, or antigen-binding fragment thereof, that binds to a human complement component C5 protein).

Peptidomimetics can be compounds in which at least a portion of a subject polypeptide is modified, and the three dimensional structure of the peptidomimetic remains substantially the same as that of the subject polypeptide. Peptidomimetics may be analogues of a subject polypeptide of the disclosure that are, themselves, polypeptides containing one or more substitutions or other modifications within the subject polypeptide sequence. Alternatively, at least a portion of the subject polypeptide sequence may be replaced with a nonpeptide structure, such that the three-dimensional structure of the subject polypeptide is substantially retained. In other words, one, two or three amino acid residues within the subject polypeptide sequence may be replaced by a non-peptide structure. In addition, other peptide portions of the subject polypeptide may, but need not, be replaced with a non-peptide structure. Peptidomimetics (both peptide and non-peptidyl analogues) may have improved properties (e.g., decreased proteolysis, increased retention or increased bioavailability). Peptidomimetics generally have improved oral availability, which makes them especially suited to treatment of disorders in a human or animal. It should be noted that peptidomimetics may or may not have similar two-dimensional chemical structures, but share common three-dimensional structural features and geometry. Each peptidomimetic may further have one or more unique additional binding elements.

Nucleic acid inhibitors can be used to bind to and inhibit a target antigen of interest. The nucleic acid antagonist can be, e.g., an aptamer. Aptamers are short oligonucleotide sequences that can be used to recognize and specifically bind almost any molecule, including cell surface proteins. The systematic evolution of ligands by exponential enrichment (SELEX) process is powerful and can be used to readily identify such aptamers. Aptamers can be made for a wide range of proteins of importance for therapy and diagnostics, such as growth factors and cell surface antigens. These oligonucleotides bind their targets with similar affinities and specificities as antibodies do (see, e.g., Ulrich (2006) *Handb Exp Pharmacol.* 173:305-326).

In some embodiments, the complement inhibitor is a non-antibody scaffold protein. These proteins are, generally, obtained through combinatorial chemistry-based adaptation of pre-existing antigen-binding proteins. For example, the binding site of human transferrin for human transferrin receptor can be modified using combinatorial chemistry to create a diverse library of transferrin variants, some of which have acquired affinity for different antigens. Ali et al. (1999) *J Biol Chem* 274:24066-24073. The portion of human transferrin not involved with binding the receptor remains unchanged and serves as a scaffold, like framework regions of antibodies, to present the variant binding sites. The libraries are then screened, as an antibody library is, against a target antigen of interest to identify those variants having optimal selectivity and affinity for the target antigen. Non-antibody scaffold proteins, while similar in function to antibodies, are touted as having a number of advantages as compared to antibodies, which advantages include, among other things, enhanced solubility and tissue penetration, less costly manufacture, and ease of conjugation to other molecules of interest. Hey et al. (2005) *TRENDS Biotechnol* 23(10):514-522.

One of skill in the art would appreciate that the scaffold portion of the non-antibody scaffold protein can include, e.g., all or part of: the Z domain of *S. aureus* protein A, human transferrin, human tenth fibronectin type III domain, kunitz domain of a human trypsin inhibitor, human CTLA-4, an ankyrin repeat protein, a human lipocalin, human crystallin, human ubiquitin, or a trypsin inhibitor from *E. elaterium*. Id.

In some embodiments, the complement inhibitor is an antibody, or antigen-binding fragment thereof, which binds to a human complement component C5 protein. (Hereinafter, the antibody may sometimes be referred to as an "anti-C5 antibody.")

In some embodiments, the anti-C5 antibody can bind to an epitope in the alpha chain of the human complement component C5 protein. Antibodies that bind to the alpha chain of C5 are described in, for example, PCT application publication no. WO 2010/015608 and U.S. Pat. No. 6,355,245. In some embodiments, the anti-C5 antibody can bind to an epitope in the beta chain of the human complement component C5 protein. Antibodies that bind to the C5 beta chain are described in, e.g., Moongkarndi et al. (1982) *Immunobiol* 162:397; Moongkarndi et al. (1983) *Immunobiol* 165:323; and Mollnes et al. (1988) *Scand J Immunol* 28:307-312.

Additional exemplary antigenic fragments of human complement component C5 are disclosed in, e.g., U.S. Pat. No. 6,355,245, the disclosure of which is incorporated herein by reference.

Additional anti-C5 antibodies, and antigen-binding fragments thereof, suitable for use in the fusion proteins described herein are described in, e.g., PCT application publication no. WO 2010/015608, the disclosure of which is incorporated herein by reference in its entirety.

In some embodiments, the anti-C5 antibody specifically binds to a human complement component C5 protein (e.g., the human C5 protein having the amino acid sequence depicted in SEQ ID NO:1). The terms "specific binding" or "specifically binds" refer to two molecules forming a complex (e.g., a complex between an antibody and a complement component C5 protein) that is relatively stable under physiologic conditions. Typically, binding is considered specific when the association constant ($K_a$) is higher than $10^6$ M$^{-1}$. Thus, an antibody can specifically bind to a C5 protein with a $K_a$ of at least (or greater than) $10^6$ (e.g., at least or greater than $10^7$, $10^8$, $10^9$, $10^{10}$, $10^{11}$ $10^{12}$, $10^{13}$, $10^{14}$, or $10^{15}$ or higher) M. Examples of antibodies that specifically bind to a human complement component C5 protein are described in, e.g., U.S. Pat. No. 6,355,245, the disclosure of which is incorporated herein by reference in its entirety.

The anti-C5 antibodies described herein can have activity in blocking the generation or activity of the C5a and/or C5b active fragments of a complement component C5 protein (e.g., a human C5 protein). Through this blocking effect, the anti-C5 antibodies inhibit, e.g., the proinflammatory effects of C5a and the generation of the C5b-9 membrane attack complex (MAC) at the surface of a cell. Anti-05 antibodies that have the ability to block the generation of C5a are described in, e.g., Moongkarndi et al. (1982) *Immunobiol* 162:397 and Moongkarndi et al. (1983) *Immunobiol* 165: 323.

In some embodiments, an anti-C5 antibody, or antigen-binding fragment thereof, can reduce the ability of a C5 protein to bind to human complement component C3b (e.g., C3b present in an AP or CP C5 convertase complex) by greater than 50 (e.g., greater than 55, 60, 65, 70, 75, 80, 85, 90, or 95 or more) %. In some embodiments, upon binding to a C5 protein, the anti-C5 antibody or antigen-binding fragment thereof can reduce the ability of the C5 protein to bind to complement component C4b (e.g., C4b present in a CP C5 convertase) by greater than 50 (e.g., greater than 55, 60, 65, 70, 75, 80, 85, 90, or 95 or more) %. Methods for determining whether an antibody can block the generation or activity of the C5a and/or C5b active fragments of a complement component C5 protein, or binding to complement component C4b or C3b, are known in the art and described in, e.g., U.S. Pat. No. 6,355,245 and Wurzner et al. (1991) *Complement Inflamm* 8:328-340.

In some embodiments, the composition comprises, and/or the antibody is, eculizumab (Soliris®; Alexion Pharmaceuticals, Inc., Cheshire, Conn.). (See, e.g., Kaplan (2002) *Curr Opin Investig Drugs* 3(7):1017-23; Hill (2005) *Clin Adv Hematol Oncol* 3(11):849-50; and Rother et al. (2007) *Nature Biotechnology* 25(11):1256-1488.) In some embodiments, the composition comprises, and/or the antibody is, pexelizumab (Alexion Pharmaceuticals, Inc., Cheshire, Conn.). (See, e.g., Whiss (2002) *Curr Opin Investig Drugs* 3(6):870-7; Patel et al. (2005) *Drugs Today (Barc)* 41(3): 165-70; and Thomas et al. (1996) *Mol Immunol* 33(17-18): 1389-401.)

In some embodiments, the C5 inhibitor is an antibody that binds to C5a (sometimes referred to herein as "an anti-C5a antibody"). In some embodiments, the antibody binds to C5a, but not to full-length C5. In some embodiments, the binding of an antibody to C5a can inhibit the biological activity of C5a. Methods for measuring C5a activity include, e.g., chemotaxis assays, RIAs, or ELISAs (see, e.g., Ward and Zvaifler (1971) *J Clin Invest* 50(3):606-16 and Wurzner et al. (1991) *Complement Inflamm* 8:328-340). In some embodiments, the binding of an antibody to C5a can inhibit the interaction between C5a and C5aR1. Suitable methods for detecting and/or measuring the interaction between C5a and C5aR1 (in the presence and absence of an antibody) are known in the art and described in, e.g., Mary and Boulay (1993) *Eur J Haematol* 51(5):282-287; Kaneko et al. (1995) *Immunology* 86(1):149-154; Giannini et al. (1995) *J Biol Chem* 270(32):19166-19172; and U.S. Patent Application Publication No. 20060160726. For example, the binding of detectably labeled (e.g., radioactively labeled) C5a to C5aR1-expressing peripheral blood mononuclear cells can be evaluated in the presence and absence of an antibody. A decrease in the amount of detectably-labeled C5a that binds to C5aR1 in the presence of the antibody, as compared to the amount of binding in the absence of the antibody, is an indication that the antibody inhibits the interaction between C5a and C5aR1. In some embodiments, the binding of an antibody to C5a can inhibit the interaction between C5a and C5L2 (see below). Methods for detecting and/or measuring the interaction between C5a and C5L2 are known in the art and described in, e.g., Ward (2009) *J Mol Med* 87(4):375-378 and Chen et al. (2007) *Nature* 446(7132):203-207 (see below).

In some embodiments, the C5 inhibitor is an antibody that binds to C5b (sometimes referred to herein as "an anti-C5b antibody"). In some embodiments, the antibody binds to C5b, but does not bind to full-length C5. The structure of C5b is described in, e.g., Müller-Eberhard (1985) *Biochem Soc Symp* 50:235-246; and Yamamoto and Gewurz (1978) *J Immunol* 120(6):2008-2015. As described above, C5b combines with C6, C7, and C8 to form the C5b-8 complex at the surface of the target cell. Protein complex intermediates formed during the series of combinations include C5b-6 (including C5b and C6), C5b-7 (including C5b, C6, and C7), and C5b-8 (including C5b, C6, C7, and C8). Upon binding of several C9 molecules, the membrane attack complex (MAC, C5b-9 terminal complement complex (TCC)) is formed. When sufficient numbers of MACs insert into target cell membranes, the openings they create (MAC pores) mediate rapid osmotic lysis of the target cells.

In some embodiments, the binding of an antibody to C5b can inhibit the interaction between C5b and C6. In some embodiments, the binding of the antibody to C5b can inhibit the assembly or activity of the C5b-9 MAC-TCC. In some embodiments, the binding of an antibody to C5b can inhibit complement-dependent cell lysis (e.g., in vitro and/or in vivo). Suitable methods for evaluating whether an antibody inhibits complement-dependent lysis include, e.g., hemolytic assays or other functional assays for detecting the activity of soluble C5b-9. For example, a reduction in the cell-lysing ability of complement in the presence of an antibody can be measured by a hemolysis assay described by Kabat and Mayer (eds.), "Experimental Immunochemistry, $2^{nd}$ Edition," 135-240, Springfield, Ill., CC Thomas (1961), pages 135-139, or a conventional variation of that assay such as the chicken erythrocyte hemolysis method as described in, e.g., Hillmen et al. (2004) *N Engl J Med* 350(6):552.

Antibodies that bind to C5b as well as methods for making such antibodies are known in the art. Commercially available anti-C5b antibodies are available from a number of vendors including, e.g., Hycult Biotechnology (catalogue number: HM2080; clone 568) and Abcam™ (ab46151 or ab46168).

Methods for determining whether a particular agent is an inhibitor of human complement component C5 are described herein and are known in the art. For example, the concentration and/or physiologic activity of C5a and C5b in a body fluid can be measured by methods well known in the art. Methods for measuring C5a concentration or activity include, e.g., chemotaxis assays, RIAs, or ELISAs (see, e.g., Ward and Zvaifler (1971) *J Clin Invest*. 50(3):606-16 and Wurzner et al. (1991) *Complement Inflamm*. 8:328-340). For C5b, hemolytic assays or assays for soluble C5b-9 as discussed herein can be used. Other assays known in the art can also be used. Using assays of these or other suitable types, candidate agents capable of inhibiting human complement component C5 such as an anti-C5 antibody, can be screened in order to, e.g., identify compounds that are useful in the methods described herein and determine the appropriate dosage levels of such compounds.

Methods for determining whether a candidate compound inhibits the cleavage of human C5 into forms C5a and C5b are known in the art and described in, e.g., Moongkarndi et al. (1982) Immunobiol 162:397; Moongkarndi et al. (1983) Immunobiol 165:323; Isenman et al. (1980) J Immunol 124(1):326-31; Thomas et al. (1996) Mol. Immunol 33(17-18):1389-401; and Evans et al. (1995) Mol. Immunol 32(16):1183-95.

Inhibition of human complement component C5 can also reduce the cell-lysing ability of complement in a subject's body fluids. Such reductions of the cell-lysing ability of complement present can be measured by methods well known in the art such as, for example, by a conventional hemolytic assay such as the hemolysis assay described by Kabat and Mayer (eds), "Experimental Immunochemistry, $2^{nd}$ Edition," 135-240, Springfield, Ill., CC Thomas (1961), pages 135-139, or a conventional variation of that assay such as the chicken erythrocyte hemolysis method as described in, e.g., Hillmen et al. (2004) N Engl J Med 350(6):552.

Antibodies that bind to C3b and, for example, inhibit the C3b convertase are also well known in the art. See for example, PCT application publication nos. WO 2010/136311, WO 2009/056631, and WO 2008/154251, the disclosures of each of which are incorporated herein by reference in their entirety. Antagonistic anti-C6 and anti-C7 antibodies have been described in, e.g., Brauer et al. (1996) Transplantation 61(4):588-594 and U.S. Pat. No. 5,679,345.

In some embodiments, the antibody is an anti-factor B antibody (such as the monoclonal antibody 1379 produced by ATCC Deposit No. PTA-6230). Anti-factor B antibodies are also described in, e.g., Ueda et al. (1987) J Immunol 138(4):1143-9; Tanhehco et al. (1999) Transplant Proc 31(5):2168-71; U.S. Pat. Nos. 7,999,082 and 7,964,705; and PCT publication no. WO 09/029669.

In some embodiments, the antibody is an anti-factor D antibody, e.g., an antibody described in Pascual et al. (1990) J Immunol Methods 127:263-269; Sahu et al. (1993) Mol Immunol 30(7):679-684; Pascual et al. (1993) Eur J Immunol 23:1389-1392; Niemann et al. (1984) J Immunol 132(2):809-815; U.S. Pat. No. 7,439,331; or U.S. patent application publication no. 20080118506.

In some embodiments, the antibody is an anti-properdin antibody. Suitable anti-properdin antibodies are also well-known in the art and include, e.g., U.S. patent application publication nos. 20110014614 and PCT application publication no. WO2009110918.

Methods for Treatment

Also provided herein are compositions and methods for treating or preventing aHUS in a subject (e.g., a human). The compositions (e.g., complement inhibitors and/or secondary agents) can be administered to a subject, e.g., a human subject, using a variety of methods that depend, in part, on the route of administration. The route can be, e.g., intravenous injection or infusion (IV), subcutaneous injection (SC), intraperitoneal (IP) injection, or intramuscular injection.

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. patent publication no. 20080241223; U.S. Pat. Nos. 5,501,856; 4,863,457; and 3,710,795; and European patent nos. EP488401 and EP430539, the disclosures of each of which are incorporated herein by reference in their entirety. The composition can be delivered to the subject by way of an implantable device based on, e.g., diffusive, erodible or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

A suitable dose of a complement inhibitor (e.g., an anti-C5 antibody or fragment thereof), which dose is capable of treating or preventing aHUS in a subject, can depend on a variety of factors including, e.g., the age, sex, and weight of a subject to be treated and the particular inhibitor compound used. For example, a different dose of an siRNA specific for human C5 may be required to treat a subject with aHUS as compared to the dose of an anti-C5 antibody required to treat the same patient. Other factors affecting the dose administered to the subject include, e.g., the type or severity of the aHUS. For example, a subject having CFH-associated aHUS may require administration of a different dosage of the inhibitor than a subject with MCP-associated aHUS. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject will depend upon the judgment of the treating medical practitioner (e.g., doctor or nurse).

The inhibitor can be administered as a fixed dose, or in a milligram per kilogram "mg/kg" dose. In some embodiments, the dose can also be chosen to reduce or avoid production of antibodies or other host immune responses against one or more active agents in the composition. While in no way intended to be limiting, exemplary dosages of an inhibitor, such as an anti-C5 antibody, include, e.g., 1-100 mg/kg, 0.5-50 mg/kg, 0.1-100 mg/kg, 0.5-25 mg/kg, 1-20 mg/kg, and 1-10 mg/kg of body weight.

In some embodiments, a human can be intravenously administered an anti-C5 antibody (e.g., eculizumab) at a dose of about 900 mg about every 12 (e.g., about every 10, 11, 13, 14, 15, 16, 17, 18, 19, 20, 21, 28, 30, 42, or 49 or more) days. See, e.g., Hill et al. (2005) Blood 106(7):2559.

In some embodiments, a human can be intravenously administered an anti-C5 antibody (e.g., eculizumab) at a dose of about 600 (e.g., about 625, 650, 700, 725, 750, 800, 825, 850, 875, 900, 925, 950, or 1,000 or more) mg every week, optionally, for two or more (e.g., three, four, five, six, seven, or eight or more) weeks. Following the initial treatment, the human can be administered the antibody at a dose of about 900 mg about every 14 (e.g., about every 11, 12, 13, 14, 15, 16, 17, 18, 19, 20, 21, 28, 30, 42, or 49 or more) days, e.g., as a maintenance dose. See, e.g., Hillmen et al. (2004) N Engl J Med. 350(6):552-9 and Dmytrijuk et al. (2008) The Oncologist 13(9):993.

In some embodiments, a human can be intravenously administered an anti-C5 antibody (e.g., eculizumab) at a dose of about 900 (e.g., 925, 950, 975, 1000, 1100, or 1200 or more) mg every week, optionally, for two or more (e.g., three, four, five, six, seven, or eight or more) weeks. Following the initial treatment, the human can be administered the antibody at a dose of about 1200 mg about every 14 (e.g., about every 11, 12, 13, 14, 15, 16, 17, 18, 19, 20, 21, 28, 30, 42, or 49 or more) days, e.g., as a maintenance dose. See, e.g., International patent application publication no. WO 2010/054403.

As used herein, "chronically administered," "chronic treatment," "treating chronically," or similar grammatical variations thereof refer to a treatment regimen that is employed to maintain a certain threshold concentration of a therapeutic agent in the blood of a patient in order to completely or substantially suppress systemic complement activity in the patient over a prolonged period of time. Accordingly, a patient chronically treated with a complement inhibitor can be treated for a period of time that is greater than or equal to 2 weeks (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks; 1, 2, 3, 4, 5, 6, 7, 8, 9, 10, 11, or 12 months; or 1, 1.5, 2, 2.5, 3, 3.5, 4, 4.5, 5, 5.5, 6, 6.5, 7, 7.5, 8, 8.5, 9, 9.5, 10, 10.5, or 12 years or for the remainder of the patient's life) with the inhibitor in an amount and with a dosing frequency that are sufficient to maintain a concentration of the inhibitor in the patient's blood that inhibits or substantially inhibits systemic complement activity in the patient. In some embodiments, the complement inhibitor can be chronically administered to a patient in need thereof in an amount and with a frequency that are effective to maintain serum hemolytic activity at less than or equal to 20 (e.g., 19, 18, 17, 16, 15, 14, 13, 12, 11, 10, 9, 8, 7, 6, or 5) %. See, e.g., Hill et al. (2005) *Blood* 106(7):2559. In some embodiments, the complement inhibitor can be administered to a patient in an amount and with a frequency that are effective to maintain serum lactate dehydrogenase (LDH) levels at within at least 20 (e.g., 19, 18, 17, 16, 15, 14, 13, 12, 11, 10, 9, 8, 7, 6, or 5) % of the normal range for LDH. See Hill et al. (2005) supra. In some embodiments, the complement inhibitor is administered to the patient in an amount and with a frequency that are effective to maintain a serum LDH level less than 550 (e.g., less than 540, 530, 520, 510, 500, 490, 480, 470, 460, 450, 440, 430, 420, 410, 400, 390, 380, 370, 360, 350, 340, 330, 320, 310, 300, 290, 280, or less than 270) IU/L. To maintain systemic complement inhibition in a patient, the complement inhibitor can be chronically administered to the patient, e.g., once a week, once every two weeks, twice a week, once a day, once a month, or once every three weeks.

A pharmaceutical composition can include a therapeutically effective amount of an inhibitor of human complement component C5 (e.g., an anti-C5 antibody or antigen-binding fragment thereof). Such effective amounts can be readily determined by one of ordinary skill in the art based, in part, on the effect of the administered inhibitor, or the combinatorial effect of the antibody and one or more additional active agents, if more than one agent is used. A therapeutically effective amount of an inhibitor of human complement component C5 (e.g., an anti-C5 antibody) can also vary according to factors such as the disease state, age, sex, and weight of the individual, and the ability of the antibody (and one or more additional active agents) to elicit a desired response in the individual, e.g., amelioration of at least one condition parameter, e.g., amelioration of at least one symptom of aHUS. For example, a therapeutically effective amount of an inhibitor of human complement component C5 (e.g., an anti-C5 antibody) can inhibit (lessen the severity of or eliminate the occurrence of) and/or prevent thrombocytopenia, microangiopathic hemolytic anemia, renal failure, and/or any one of the symptoms of aHUS known in the art or described herein. A therapeutically effective amount is also one in which any toxic or detrimental effects of the composition are outweighed by the therapeutically beneficial effects.

The terms "therapeutically effective amount" or "therapeutically effective dose," or similar terms used herein are intended to mean an amount of an agent (e.g., an inhibitor of human complement component 5) that will elicit the desired biological or medical response (e.g., an improvement in one or more symptoms of aHUS). In some embodiments, a composition described herein contains a therapeutically effective amount of an inhibitor of human complement component C5. In some embodiments, a composition described herein contains a therapeutically effective amount of an antibody, or antigen-binding fragment thereof, which binds to a complement component C5 protein. In some embodiments, the composition contains two or more (e.g., three, four, five, six, seven, eight, nine, 10, or 11 or more) different inhibitors of human complement component C5 such that the composition as a whole is therapeutically effective. For example, a composition can contain an antibody that binds to a human C5 protein and an siRNA that binds to, and promotes the degradation of, an mRNA encoding a human C5 protein, wherein the antibody and siRNA are each at a concentration that when combined are therapeutically effective. In some embodiments, the composition contains the inhibitor and one or more second active agents such that the composition as a whole is therapeutically effective. For example, the composition can contain an antibody that binds to a human C5 protein and another agent useful for treating or preventing aHUS.

Toxicity and therapeutic efficacy of such compositions can be determined by known pharmaceutical procedures in cell cultures or experimental animals (animal models of aHUS). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions, or inhibitors (e.g., anti-C5 antibodies) of the compositions, that exhibit high therapeutic indices are preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. Suitable animal models of aHUS are known in the art and are described in, e.g., Atkinson et al. (2007) *Journal of Experimental Medicine* 204(6):1245-1248. The dosage of such inhibitors lies generally within a range of circulating concentrations of the inhibitors (e.g., an anti-C5 antibody or antigen-binding fragment thereof) that include the $ED_{50}$ with little or no toxicity. The dosage may vary within this range depending upon the dosage form employed and the route of administration utilized. For an inhibitor of human complement component C5 (e.g., an anti-C5 antibody) used as described herein (e.g., for treating or preventing aHUS), the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, the required dose of an inhibitor of human complement component C5 can be determined based on the concentration of human C5 protein in the subject's blood. For example, a subject having a higher concentration of circulating human C5 protein levels may require a higher dose of a human C5 inhibitor than a subject having lower levels of circulating human C5. Methods for determining the concentration of human complement component C5 in a blood-derived fluid sample from a subject are known in the art and described in, e.g., Rawal et al. (1998) *J Biol Chem* 273(27):16828-16835.

In some embodiments, the methods can be performed in conjunction with other therapies for aHUS. For example, the composition can be administered to a subject at the same time, prior to, or after, nephrectomy (e.g., bilateral nephrectomy), dialysis, a plasma exchange, or a plasma infusion (see, e.g., Noris et al. (2005) "Non-shiga toxin-associated hemolytic uremic syndrome." In: Zipfel P (ed). *Complement and Kidney Disease*. Basel: Birkhauser-Verlag, 65-83).

A "subject," as used herein, can be any mammal. For example, a subject can be a human, a non-human primate (e.g., monkey, baboon, or chimpanzee), a horse, a cow, a pig, a sheep, a goat, a dog, a cat, a rabbit, a guinea pig, a gerbil, a hamster, a rat, or a mouse. In some embodiments, the subject is an infant (e.g., a human infant).

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition comprising an inhibitor of human complement component C5).

As used herein, a subject "at risk for developing aHUS" is a subject having one or more (e.g., two, three, four, five, six, seven, or eight or more) risk factors for developing the disorder. Risk factors for aHUS are well known in the art of medicine and include, e.g., a predisposition to develop the condition, i.e., a family history of the condition or a genetic predisposition to develop the condition such as, e.g., one or more mutations in complement Factor H (CFH), membrane cofactor protein (MCP; CD46), C4b-binding protein, complement factor B (CFB), or complement factor I (CFI). See, e.g., Warwicker et al. (1998) *Kidney Int* 53:836-844; Richards et al. (2001) *Am J Hum Genet* 68:485-490; Caprioli et al. (2001) *Am Soc Nephrol* 12:297-307; Neuman et al. (2003) *J Med Genet* 40:676-681; Richards et al. (2006) *Proc Natl Acad Sci USA* 100:12966-12971; Fremeaux-Bacchi et al. (2005) *JAm Soc Nephrol* 17:2017-2025; Esparza-Gordillo et al. (2005) *Hum Mol Genet* 14:703-712; Goicoechea de Jorge et al. (2007) *Proc Natl Acad Sci USA* 104(1):240-245; Blom et al. (2008) *J Immunol* 180(9):6385-91; and Fremeaux-Bacchi et al. (2004) *J Medical Genet* 41:e84). See also Kavanagh et al. (2006), supra. Risk factors also include, e.g., infection with *Streptococcus pneumoniae*, pregnancy, cancer, exposure to anti-cancer agents (e.g., quinine, mitomycin C, cisplatin, or bleomycin), exposure to immunotherapeutic agents (e.g., cyclosporine, OKT3, or interferon), exposure to anti-platelet agents (e.g., ticlopidine or clopidogrel), HIV infection, transplantation, autoimmune disease, and combined methylmalonic aciduria and homocystinuria (cb1C). See, e.g., Constantinescu et al. (2004) *Am J Kidney Dis* 43:976-982; George (2003) *Curr Opin Hematol* 10:339-344; Gottschall et al. (1994) *Am J Hematol* 47:283-289; Valavaara et al. (1985) *Cancer* 55:47-50; Miralbell et al. (1996) *J Clin Oncol* 14:579-585; Dragon-Durey et al. (2005) *J Am Soc Nephrol* 16:555-63; and Becker et al. (2004) *Clin Infect Dis* 39:S267-S275. Thus, a human at risk for developing aHUS can be, e.g., one who has a family history of aHUS and/or one who has an HIV infection. From the above it will be clear that subjects "at risk for developing aHUS" are not all the subjects within a species of interest.

A subject "suspected of having aHUS" is one having one or more symptoms of the condition. Symptoms of this condition are well-known to those of skill in the art of medicine and include, e.g., severe hypertension, proteinuria, uremia, lethargy/fatigue, irritability, thrombocytopenia, microangiopathic hemolytic anemia, and renal function impairment (e.g., acute renal failure). It will be clear from the foregoing passage that subjects "suspected of having aHUS" are not all the subjects within a species of interest.

aHUS can be genetic, acquired, or idiopathic. aHUS can be considered genetic when two or more (e.g., three, four, five, or six or more) members of the same family are affected by the disease at least six months apart and exposure to a common triggering agent has been excluded, or when one or more aHUS-associated gene mutations (e.g., one or more mutations in CFH, MCP/CD46, CFB, or CFI) are identified in a subject. For example, a subject can have CFH-associated aHUS, CFB-associated aHUS, CFI-associated aHUS, or MCP-associated aHUS. Up to 30% of genetic aHUS is associated with mutations in CFH, 12% with mutations in MCP, 5-10% with mutations in CFI, and less than 2% with mutations in CFB. Genetic aHUS can be multiplex (i.e., familial; two or more affected family members) or simplex (i.e., a single occurrence in a family). aHUS can be considered acquired when an underlying environmental factor (e.g., a drug, systemic disease, or viral or bacterial agents that do not result in Shiga-like exotoxins) can be identified. aHUS can be considered idiopathic when no trigger (genetic or environmental) is evident.

In some embodiments, the methods can include identifying the subject as one having, suspected of having, or at risk for developing aHUS. In addition to use of the aHUS biomarker profiling described herein, laboratory tests can be performed to determine whether a human subject has thrombocytopenia, microangiopathic hemolytic anemia, or acute renal insufficiency. Thrombocytopenia can be diagnosed by a medical professional as one or more of: (i) a platelet count that is less than 150,000/mm$^3$ (e.g., less than 60,000/mm$^3$); (ii) a reduction in platelet survival time that is reduced, reflecting enhanced platelet disruption in the circulation; and (iii) giant platelets observed in a peripheral smear, which is consistent with secondary activation of thrombocytopoiesis. Microangiopathic hemolytic anemia can be diagnosed by a medical professional as one or more of: (i) hemoglobin concentrations that are less than 10 mg/dL (e.g., less than 6.5 mg/dL); (ii) increased serum lactate dehydrogenase (LDH) concentrations (>460 U/L); (iii) hyperbilirubinemia, reticulocytosis, circulating free hemoglobin, and low or undetectable haptoglobin concentrations; and (iv) the detection of fragmented red blood cells (schistocytes) with the typical aspect of burr or helmet cells in the peripheral smear together with a negative Coombs test. See, e.g., Kaplan et al. (1992) "Hemolytic Uremic Syndrome and Thrombotic Thrombocytopenic Purpura," Informa Health Care (ISBN 0824786637) and Zipfel (2005) "Complement and Kidney Disease," Springer (ISBN 3764371668).

Blood concentrations of C3 and C4 can also be used as a measure of complement activation or dysregulation. In addition, a subject's condition can be further characterized by identifying the subject as harboring one or more mutations in a gene associated with aHUS such as CFI, CFB, CFH, or MCP (supra). Suitable methods for detecting a mutation in a gene include, e.g., DNA sequencing and nucleic acid array techniques. See, e.g., Breslin et al. (2006) *Clin Am Soc Nephrol* 1:88-99 and Goicoechea de Jorge et al. (2007) *Proc Natl Acad Sci USA* 104:240-245.

In some embodiments, the inhibitor of human complement component C5 (e.g., an anti-C5 antibody or antigen-binding fragment thereof) can be administered to a subject as a monotherapy. Alternatively, as described above, the inhibitor can be administered to a subject as a combination therapy with another treatment, e.g., another treatment for aHUS. For example, the combination therapy can include administering to the subject (e.g., a human patient) one or more additional agents (e.g., anti-hypertensives) that provide a therapeutic benefit to the subject who has, or is at risk of developing, aHUS. In some embodiments, the inhibitor of human complement component C5 and the one or more additional active agents are administered at the same time. In other embodiments, the inhibitor is administered first in time and the one or more additional active agents are administered second in time. In some embodiments, the one or more additional active agents are administered first in time and the inhibitor is administered second in time.

The inhibitor of human complement component C5 can replace or augment a previously or currently administered therapy. For example, upon treating with an anti-C5 antibody or antigen-binding fragment thereof, administration of the one or more additional active agents can cease or diminish, e.g., be administered at lower levels. In some embodiments, administration of the previous therapy can be maintained. In some embodiments, a previous therapy will be maintained until the level of inhibitor of human C5 reaches a level sufficient to provide a therapeutic effect. The two therapies can be administered in combination.

Monitoring a subject (e.g., a human patient) for an improvement in aHUS, as defined herein, means evaluating the subject for a change in a disease parameter, e.g., an improvement in one or more symptoms of the disease. Such symptoms include any of the symptoms of aHUS described herein. In some embodiments, the evaluation is performed at least 1 hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after treatment begins. The subject can be evaluated in one or more of the following periods: prior to beginning of treatment; during the treatment; or after one or more elements of the treatment have been administered. Evaluating can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for aHUS described herein.

Kits

Also provided are kits comprising various reagents and materials useful for carrying out the methods described herein. The procedures for measuring, diagnosing, evaluating, and/or assessing described herein may be performed by diagnostic laboratories, experimental laboratories, or individual practitioners. The invention provides kits which can be used in any or all of these settings.

In some embodiments, the kits described herein comprise materials and reagents for, among other things, characterizing or processing biological samples (e.g., biological fluids), measuring biomarker levels (e.g., protein or nucleic acid levels), diagnosing aHUS in a subject, or monitoring treatment response in a subject according to the methods provided herein. In certain embodiments, an inventive kit comprises at least one or more reagents that specifically detect protein levels of one or more aHUS biomarker proteins (e.g., those selected from Table 1) and, optionally, instructions for using the kit. The kit can include, e.g., any of the arrays described herein.

In some embodiments, the kits may include suitable control samples (e.g., biological fluids from normal healthy individuals or a solution comprising a known, control amount of a particular analyte of interest). In some embodiments, kits of the invention may include instructions for using the kit according to one or more methods described herein and may comprise instructions for processing the biological sample (e.g., a biological fluid) obtained from the subject and/or for performing the test or instructions for interpreting the results.

The following examples are intended to illustrate, not limit, the invention.

EXAMPLES

To better understand the pathology of aHUS, the inventors have collected samples of biological fluids (whole blood, serum, plasma, and urine) from patients having aHUS or suspected of having aHUS both before and, at several points, after initiating treatment with a complement inhibitor (the anti-C5 antibody eculizumab). One objective of this study was to define a series of clinically definable parameters that could be used to monitor responsiveness of patients to treatment with the complement inhibitor as well as markers of the disease and progression or abatement thereof. The inventors identified several proteins whose expression and/or activity was correlated with either the aHUS disease state and/or responsiveness of an aHUS patient to treatment with a complement inhibitor. The proteins were those involved or associated with complement and/or endothelial cell activation, inflammation, renal injury, and coagulation (see Table 1).

For the study, a total of 41 adult subjects (27 females and 12 males) with a confirmed diagnosis of aHUS were recruited as were normal healthy adult volunteers. All patients had confirmed aHUS at screening based on one or more of the following characteristics: platelet count less than $150 \times 10^9$/L; hemoglobin levels at less than the lower limit of normal; LDH levels that were greater than or equal to 1.5 times the upper limit of normal; serum creatinine levels that were greater than or equal to the upper limit of normal; and an ADAMTS13 activity level that was greater than 5%. All patients tested negative for Shiga toxin.

The mean patient age at inclusion was 40.3 years old. 68% of the patients were female; 2 (4.8%) were black or African-American; and 1 patient (2.4%) was of Asian descent. Six patients (14.6%) reported a family history of aHUS. Twenty (48.7%) had at least one identified complement regulatory protein mutation or tested positive for an autoantibody that binds to a complement regulatory protein. Thirty patients (73.2%) presented with a first clinical manifestation of aHUS. Six patients (14%) immediately initiated eculizumab without use of plasma exchange/infusion (PE/PI). Twenty-four patients (58.5%) were on dialysis at baseline (prior to eculizumab treatment). Nine patients (22%) had previously undergone a renal transplant. Twenty-seven (66%) had a platelet count that was less than $150 \times 10^9$/L. Thirty-two (78%) patients had a serum LDH level that was greater than the upper limit of normal. The mean haptoglobin (Hp) levels for the patients in this cohort was 0.6±0.4 g/L; whereas the mean serum creatinine levels in this patient cohort was 411±264.6 µmol/L (N=40).

Biological fluids were collected at enrollment in the study (prior to treatment) and then following treatment at each administration of the drug. Eculizumab was administered to the subjects under the following schedule: 900 mg once per week for four weeks; 1200 mg as the fifth dose; and 1200 mg once every two weeks thereafter for up to 55 weeks as part of a Phase 2 clinical trial.

Example 1

Materials and Methods

Urine Samples

Freshly collected urine was immediately mixed with protease inhibitors. The concentrations of several analytes including NGAL, cystatin C, clusterin, TIMP-1, β2-microglobulin, C5b9, C5a, and creatinine in urine collected from the subjects were measured using commercially-available kits as described briefly below.

NGAL levels were measured in urine using a commercially available kit (R&D Systems, Minneapolis, Minn.; catalogue number: DLCN20). Briefly, urine samples were diluted 1:3 using kit supplied calibrator diluent RD5-24. 50 µL of each sample or kit standard control (NS0-expressed recombinant human Lipocalin-2) were added to wells of an assay plate in duplicate, each well containing 100 µL of kit-supplied Assay Diluent RD1-52. After a two hour incubation at 4° C. in the refrigerator, wells were washed four times with 200 µL per well of wash solution. An enzymatically (horseradish peroxidase)-labeled anti-NGAL conjugate was added at 200 µL per well and incubated for two hours at 4° C. in the refrigerator. Wells were washed four times with 200 µL per well of wash solution and developed by adding 200 µL per well of kit-supplied TMB Substrate Solution (substrate for the enzyme of the anti-NGAL conjugate) and incubated at room temperature in the dark for 30 minutes. TMB is a substrate for horseradish peroxidase often used in ELISA. Reaction between the substrate and immobilized horseradish peroxidase (HRP) conjugated to antibodies in the ELISA wells produces a blue colored solution. After reaching the desired color intensity, the reaction is terminated by addition of the stop solution (acidic), which changes the solution color from blue to yellow. Thus, the reactions were stopped after the incubation by adding 50 µL per well of kit-supplied Stop Solution to each well and the absorbance read at 450 nm.

Cystatin C levels were measured with a commercially available kit (R&D Systems, Minneapolis, Minn.; catalogue number: DSCTC0). Briefly, urine samples were diluted 1:3 using kit supplied calibrator diluent RD5-24. 50 µL of each sample or kit standard control (recombinant human CysC) were added to wells of an assay plate in duplicate, each well containing 100 µL of kit-supplied Assay Diluent RD1-52. After a two hour incubation at 4° C. in the refrigerator, wells were washed four times with 200 µL per well of wash solution. An enzymatically-labeled anti-CysC conjugate was added at 200 µL per well and incubated for two hours at 4° C. in the refrigerator. Wells were washed four times with 200 µL per well of wash solution and developed by adding 200 µL per well of kit-supplied TMB Substrate Solution (substrate for the enzyme of the anti-CysC conjugate) and incubated at room temperature in the dark for 30 minutes. The reactions were stopped after the incubation by adding 50 µL per well of kit-supplied Stop Solution to each well and the absorbance read at 450 nm.

Clusterin levels were measured with a commercially available kit (R&D Systems, Minneapolis, Minn.; catalogue number: DCLU00). Briefly, urine samples were diluted 1:3 using kit supplied calibrator diluent RD5T. 50 µL of each sample or kit standard control (recombinant human clusterin) were added to wells of an assay plate in duplicate, each well containing 100 µL of kit-supplied Assay Diluent RD1-19. After a two hour incubation at room temperature on the orbital shaker set at 500 rpm, wells were washed four times with 200 µL per well of wash solution. An enzymatically-labeled anti-clusterin conjugate was added at 200 µL per well and incubated for two hours at room temperature on the orbital shaker set at 500 rpm. Wells were washed four times with 200 µL per well of wash solution and developed by adding 200 µL per well of TMB Substrate Solution and incubated at room temperature in the dark for 30 minutes. The reactions were stopped after the incubation by adding 50 µL per well of Stop Solution to each well and the absorbance read at 450 nm.

TIMP-1 levels were measured with a commercially available kit (R&D Systems, Minneapolis, Minn.; catalogue number: DTM100). Briefly, urine samples were diluted 1:2 using kit-supplied calibrator diluent RD5P. 50 µL of each sample or kit standard control (recombinant human TIMP-1) were added to wells of an assay plate in duplicate, each well containing 100 µL of kit-supplied Assay Diluent RD1X. After a two hour incubation at room temperature on the orbital shaker set at 500 rpm, wells were washed three times with 200 µL per well of wash solution. An enzymatically-labeled anti-TIMP-1 conjugate was added at 200 µL per well and incubated for two hours at room temperature on the orbital shaker set at 500 rpm. Wells were washed four times with 200 µL per well of wash solution and developed by adding 200 µL per well of TMB Substrate Solution and incubated at room temperature in the dark for 30 minutes. The reactions were stopped after the incubation by adding 50 µL per well of Stop Solution to each well and the absorbance read at 450 nm.

β2M levels were measured with a commercially available kit (R&D Systems, Minneapolis, Minn.; catalogue number: DBM200). Briefly, urine samples were diluted 1:10 using kit supplied Sample Diluent. 20 µL of each sample, kit controls or kit standards were added to wells in duplicate, containing 100 µL of a solution containing enzymatically-labeled anti-β2M conjugate. After a one hour incubation at room temperature, wells were washed six times with 200 µL per well of wash solution. Wells were developed by adding 100 µL per well of TMB Substrate solution and incubated at room temperature in the dark for 15 minutes. The reactions were stopped after the incubation by adding 100 µL per well of Stop Solution to each well and the absorbance read at 450 nm.

Creatinine levels were measured with a commercially available kit (R&D Systems, Minneapolis, Minn.; catalogue number: KGE005). Briefly, urine samples were diluted 1:20 using water and 50 µL of samples, kit controls or kit standards were added to wells in duplicate, containing 100 µL of the kit-supplied Alkaline Picrate Solution. After a 30 minute incubation at room temperature, the absorbance at 490 nm was measured.

C5b-9 levels were measured with a commercially available kit (BD Biosciences, San Jose, Calif.; catalogue number: 558315) and an optEIA reagent set B (BD Biosciences, San Jose, Calif.; catalogue number: 550534). Briefly, an anti-C5b-9 capture antibody was diluted 1:250 in coating buffer, 100 pL of which was added to each well of a 96 well maxisorp plate (Nunc; catalogue number: 439454) and incubated overnight at 4° C. in the refrigerator. Wells were washed three times with 200 µL per well of wash solution and blocked by adding 200 μL per well of kit-supplied Assay Diluent for one hour at room temperature. Wells were washed three times with 200 μL per well of wash solution and 100 μL of urine samples or kit standards were added to wells in duplicate. After a two hour incubation at room temperature, wells were washed three times with 200 μL per well of wash solution. 100 μL of the kit-supplied C5b-9 Working Detector Antibody Solution was added to each well and incubated for one hour at room temperature. Wells were washed seven times with 200 μL per well of wash solution and developed by adding 100 μL per well of TMB Substrate Solution and incubated at room temperature in the dark for 30 minutes. The reactions were stopped after the incubation by adding 50 μL per well of Stop Solution to each well and the absorbance read at 450 nm.

C5a levels were measured with a commercially available kit (BD Biosciences, San Jose, Calif.; catalogue number: 557965). Briefly, 100 μL of urine samples or kit standards were added to wells in duplicate containing 50 μL of kit-supplied ELISA Diluent. After a two hour incubation at room temperature, wells were washed five times with 200 μL per well of wash solution. 100 μL of the kit-supplied C5a Working Detector Antibody Solution was added to each well and incubated for one hour at room temperature. Wells were washed seven times with 200 μL per well of wash solution and developed by adding 100 μL per well of TMB Substrate Solution and incubated at room temperature in the dark for 30 minutes. The reactions were stopped after the incubation by adding 50 μL per well of Stop Solution to each well and the absorbance read at 450 nm.

Plasma

Plasma samples were prepared as follows. Blood was collected in a 10 mL BD™ P100 tube (Becton Dickinson) containing EDTA. Whole blood was centrifuged no later than 60 minutes after collection in a refrigerated centrifuge (set to maintain 4-8° C.) for 10 minutes at 3000 rpm. Plasma was then obtained from the sample following centrifugation. Hemolyzed samples were discarded.

The concentration of several analytes including Ba, prothrombin fragment 1+2, thrombomodulin, vWF, sC5b-9, and C5a in plasma fractions of blood collected from the subjects was measured using commercially-available kits as described briefly below.

Ba levels were measured with a commercially available kit (Quidel, San Diego, Calif.; catalogue number: A033). Briefly, wells of an assay plate were washed three times with wash solution. Plasma samples were diluted 1:1000 with kit-supplied specimen diluent and 100 μL of the diluted plasma samples, kit controls and standards were added to wells in duplicate. After a 60 minute incubation at room temperature, the wells were washed five times with 200 μL per well of wash solution. 100 μL of an enzymatically-labeled anti-Ba antibody conjugate were added to each well and incubated for sixty minutes at room temperature. After five washes with wash solution, 100 μL of TMB substrate was added to each well and incubated for fifteen minutes at room temperature protected from light. The reaction was stopped with the addition of 100 μL per well of stop solution and absorbance was read at 450 nm.

Prothrombin fragment 1+2 levels in EDTA plasma were measured with the Enzygnost F1+2 kit (Siemens Healthcare; catalogue number: OPBD03). Briefly, plasma samples were diluted 1:2 with sample buffer and 50 μL of the diluted samples, or standard (containing a known concentration of recombinant human prothrombin fragment 1+2) were added to wells. After a 30 minute incubation at 37° C., the wells were washed three times with 200 μL per well of wash solution. 100 μL of an enzymatically-labeled anti-prothrombin fragment 1+2 antibody conjugate were added to each well and incubated for 15 minutes at 37° C. After three additional washes, 100 μL of chromagen substrate were added to each well and incubated 15 minutes at room temperature protected from light. The reaction was stopped by the addition of 100 μL of stop solution to each well and absorbance read at 450 nm.

Levels of thrombomodulin (TM) in EDTA plasma were evaluated with the TM ELISA kit (American Diagnostica, Stamford, Conn.; catalogue number: 837). Briefly, plasma samples were diluted 1:4 with sample buffer and 200 μL of diluted samples or standard (containing a known concentration of recombinant TM) was added to wells. After a 60 minute incubation at room temperature, wells of the assay plate were washed four times with 200 μL/well of wash solution. A solution of an enzymatically-labeled anti-TM antibody was added (200 μL per well) and incubated for 30 minutes at room temperature. After 4 washes, 200 μL of substrate were added to each well and the wells were incubated for 20 minutes at room temperature protected from light. The reaction was stopped with 100 μL of 0.5 M $H_2SO_4$ and the absorbance at 450 nm was measured.

Levels of von Willebrand Factor (vWF) activity were determined in EDTA plasma by an ELISA kit utilizing capture antibody specific for vWF collagen binding sites (American Diagnostica; catalogue number: 885). Plasma samples and kit controls were diluted 1:20 with assay diluent and 100 μL of the diluted samples and controls added to wells in duplicate. After a 60 minute incubation at room temperature, the wells were washed 5 times with wash solution and 100 μL of an enzymatically-labeled anti-vWF conjugate were added to each well. The wells were incubated for 15 minutes at room temperature and washed 5 times with wash solution. 100 μL of TMB substrate (which, upon cleavage by the enzyme, generates a detectable signal) was added to each well. The wells were incubated for 15 minutes at room temperature protected from light followed by the addition of 100 μL of kit-supplied stop solution to each well. Absorbance was measured at 450 nm within 30 minutes of the addition of stop solution.

Circulating levels of sC5b-9 were determined with a human C5b-9 ELISA set (BD Biosciences, San Diego, Calif.; catalogue number: 558315) and a BD optEIA reagent set B (BD Biosciences; catalogue number: 550534). Briefly, an anti-C5b-9 capture antibody was diluted 1:250 in kit-supplied coating buffer, 100 μL of which were added to wells of a 96 well maxisorp plate (Nunc) and incubated overnight at 4° C. Following three washes in wash solution, wells were blocked with 200 μL kit-supplied assay diluent for one hour at room temperature. Following 3 more washes with wash solution, 100 μL of the plasma samples (diluted 1:100 in assay diluent) or standards (containing a known concentration of purified sC5b-9) were added and incubated for two hours at room temperature. The wells were washed three times with wash solution and 100 μL of working detector (which contains a biotin-labeled anti-C5b-9 detection antibody and streptavidin-labeled horseradish peroxidase diluted 1:250 in assay diluent) added to each well. Following a one hour incubation at room temperature, the wells were washed seven times with wash solution and 100 μL of substrate TMB solutions added to each well. The reaction was allowed to develop for 30 minutes at room temperature protected from light. Following the addition of 50 μL of stop solution to each well, absorbance was determined at 450 nm.

Circulating levels of C5a were determined with a sandwich ELISA utilizing the BD optEIA reagent set B (BD Biosciences; catalogue number: 550534). All incubations were performed in the presence of futhan (BD Biosciences; catalogue number: 550236). Briefly, an anti-C5a capture antibody was diluted to 2 μg/mL in kit-supplied coating buffer, 100 μL of which were added to wells of a 96 well maxisorp plate (Nunc) followed by an overnight incubation at 4° C. Following three washes in wash solution, wells were blocked with 200 μL assay diluent for one hour at room temperature. Following 3 more washes with wash solution, 50 μL of plasma samples (diluted 1:5 in assay diluent) or standards (containing a known concentration of C5a) were added and incubated for one hour at room temperature. The wells were washed 4 times with wash solution and 100 μL of working detector added to each well contains a biotin-labeled anti-C5a detection antibody and streptavidin-labeled horseradish peroxidase diluted 1:250 in assay diluent). Following an incubation for one hour at room temperature, wells were washed seven times with wash solution and 100 μL of substrate TMB solutions added to each well. The reaction was allowed to develop for 30 minutes at room temperature protected from light. Following the addition of 50 μL of stop solution to each well, absorbance was measured at 450 nm.

Serum

Serum samples were processed as follows. Blood was collected in a 10 mL vacutainer serum separating (SST) tube. The tube was inverted five times and the blood allowed to clot at room temperature for at least 30 minutes, but no more than two hours. The tube was subjected to centrifugation at 1800 rcf with the brake on. Hemolyzed samples were discarded.

The quantitative determination of various analytes in serum was carried out using human Cytometric Bead Array (CBA) Flex Set Kits (CBA Flex Set; Becton Dickinson Biosciences, San Diego, Calif.), and acquired by flow cytometer (FACS LSR II, Becton Dickinson) according to the manufacturer's instructions. A Flex set capture bead is a single bead population with distinct fluorescent intensity and is coated with a capture antibody specific for a soluble protein. Each bead population is given an alphanumeric position designation, indicating its position relative to other beads in the BD CBA Flex Set system. Beads with different positions can be combined in assays to create a multiplex assay. In a Flex Set assay the capture bead, PE conjugated detection reagent, and the standard or test samples are incubated together to form sandwich complexes.

Briefly, standards for each analyte were mixed and a serial dilution was performed using the assay diluent. Capture beads for each analyte were prepared and pooled using Capture bead diluent for serum/plasma. Serum samples were diluted appropriately and along with the standards were incubated with the mixed capture beads in a total volume of 100 μL for one hour at room temperature. Detection phycoerythrin (PE) reagents were mixed for all analytes and were added to the tubes (50 μL). The samples were washed with wash buffer after an incubation of two hours at room temperature in the dark and were acquired by flow cytometer after reconstitution of the pellet in the wash buffer.

The following bead sets were incubated with serum samples diluted 1:4 in kit-supplied assay diluent (wherein the biomarker protein specified indicates the capture antibody conjugated to the bead): IFN-γ (Bead E7; catalogue number: 558283); IL-12 p70 (Bead E5; catalogue number: 558283); IL-1β (Bead B4; catalogue number: 558279); IL-6 (Bead A7; catalogue number: 558276); IL-8 (Bead A9; catalogue number: 558277); CXCL-9 (Bead E8; catalogue number: 558286); CXCL-10 (Bead B5; catalogue number: 558280); MCP-1 (Bead D8; catalogue number: 558287); VEGF (Bead B8; catalogue number: 558336); and sCD40L (Bead C7; catalogue number 560305). The following bead sets were incubated with serum samples diluted 1:50 in kit-supplied diluent: ICAM-1 (Bead A4; catalogue number: 560269); VCAM-1 (Bead D6; catalogue number: 560427); TNFR1 (Bead C4; catalogue number: 560156); E-selectin (Bead D9; catalogue number: 560419); P-selectin (Bead D7; catalogue number: 560426); and CCL5 (Bead D4; catalogue number: 558324).

Example 2

Results

Markers of Ongoing Complement Activation

As summarized in Table 2 below, relative to the concentration in a sample of biological fluid from healthy volunteers, the plasma concentration of complement component Ba and sC5b9 and the urine concentration of C5a and sC5b-9 were elevated in the majority of aHUS patients. See also FIG. 1.

TABLE 2

| aHUS Biomarker Protein | n/N (%) elevated at baseline | P-value |
| --- | --- | --- |
| Plasma Ba | 35/35 (100.0) | <0.0001 |
| Plasma sC5b-9 | 37/38 (97.4) | <0.0001 |
| Urine C5a | 26/29 (89.7) | 0.0007 |
| Urine sC5b-9 | 23/27 (85.2) | 0.0025 |

* "N" indicates the total number of patients evaluated for a given biomarker, and "n" indicates the number of those "N" patients with elevated levels of the biomarker protein.

These results indicate that significant systemic alternative pathway complement activation is ongoing in aHUS patients.

Figure 1C:
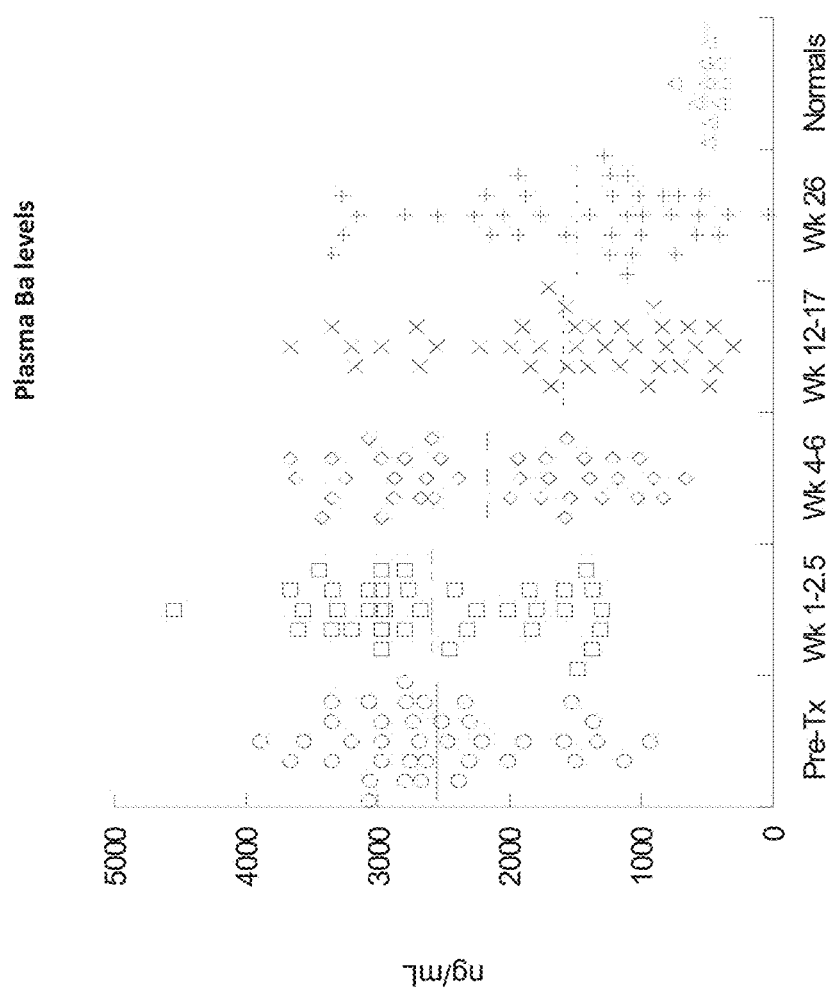
FIG. 1C is a dot plot depicting the concentration of complement component Ba (in ng/mL) in the plasma of aHUS patients both before treatment with eculizumab (Pre- Tx) and various weeks after initiating treatment with eculizumab. The concentration of Ba was also measured in the plasma from normal, healthy individuals (normals).

Following treatment with eculizumab, the mean levels (concentrations) of these aHUS biomarkers were reduced (FIGS. 1A-C). The mean levels of urinary C5a and sC5b-9 are reduced significantly at between 1 to 2.5 weeks following initiation of treatment and remained so. The mean percentage reduction in urinary C5a levels was greater than 40% at week 3 post-treatment and over 70% by week 6 (FIG. 1D). Urinary sC5b-9 levels were reduced by over 60% by week 3 (FIG. 1E). These markers eventually normalized. Plasma Ba levels were also significantly reduced (p=0.0053) at around four to six weeks following treatment with eculizumab, suggesting that with time eculizumab reduces the initiation or amplification of the classical complement pathway (FIG. 1C). However, the mean percentage reduction in plasma Ba levels was around 10% at week 6 and over 30% by week 12 (FIG. 1F).

Figure 2C:
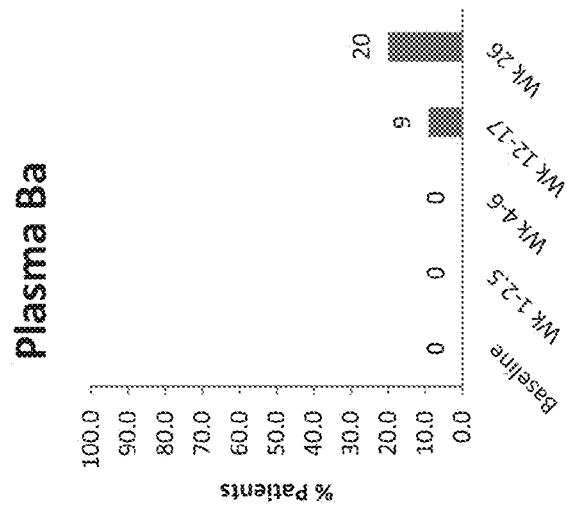
FIGS. 2A-2C are bar graphs depicting the percentage of aHUS patients who achieve normalized concentrations of urinary C5a (FIG. 2A), urinary sC5b9 (FIG. 2B), and plasma Ba (FIG. 2C) at baseline (pre-treatment with eculizumab) and various weeks following initiation of treatment with eculizumab.
Figure 2B:
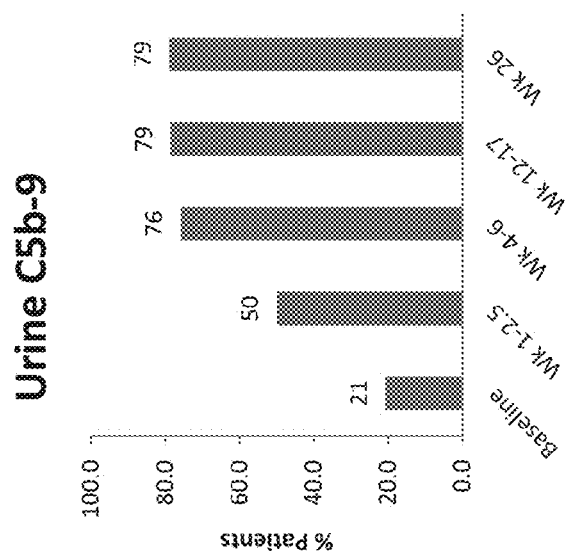
Figure 2A:
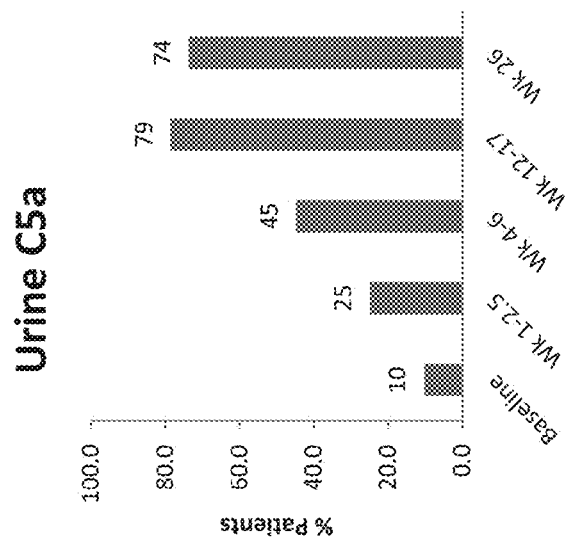

The percentage of treated aHUS patients who experience normalized complement biomarker protein levels over time is shown in FIGS. 2A-C. For example, as shown in FIG. 2B, 50% of treated aHUS patients exhibit normalized levels of urinary sC5b-9 by 2.5 weeks post-treatment initiation with eculizumab. By 17 weeks post-initiation of treatment, 79% of treated aHUS patients exhibited normalized sC5b-9 levels. However, Ba levels do not normalize in most patients (FIGS. 1C and 2C). These data indicate that even with eculizumab therapy there may be, in some patients, low level ongoing complement activation.

Markers of Platelet and Hemostatic Activation

Figure 3A:
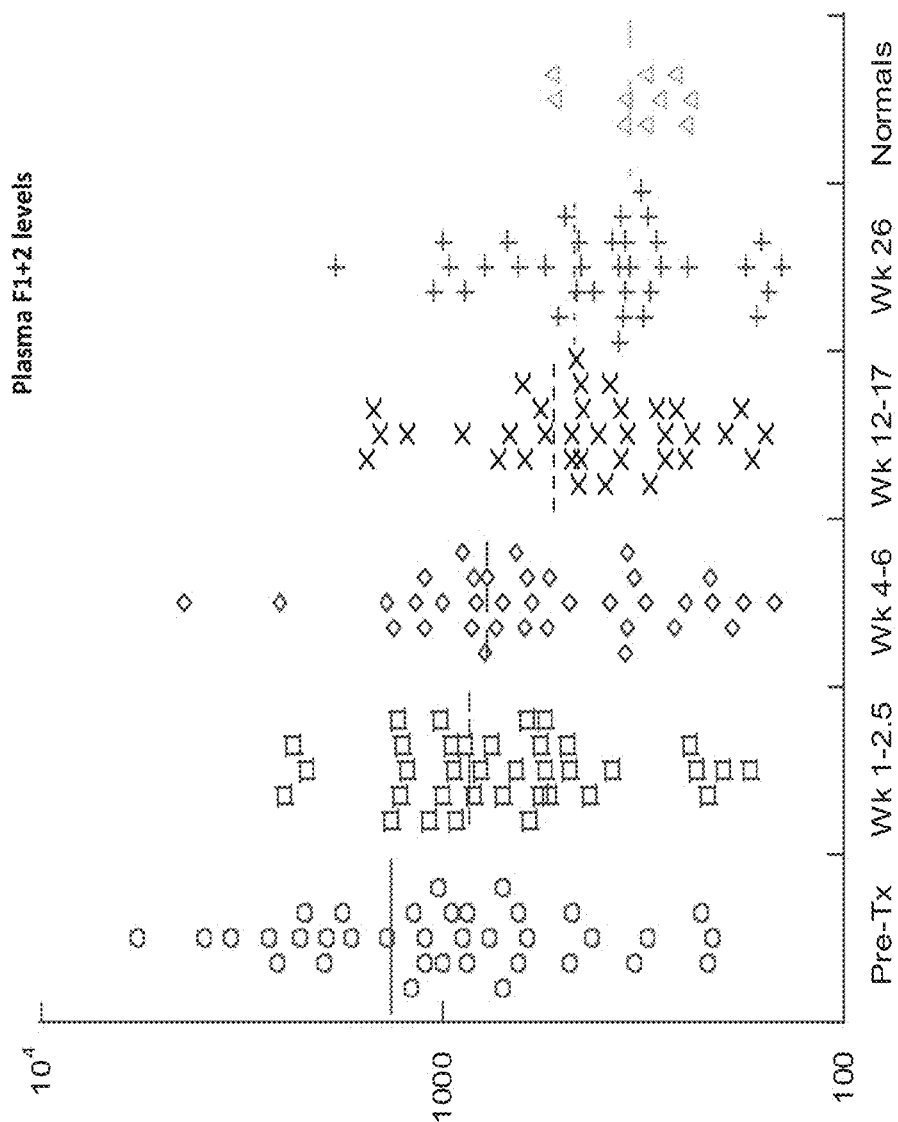
FIG. 3A is a dot plot depicting the concentration of prothrombin fragment 1+2 (in pmol/L) in the plasma of aHUS patients both before treatment with eculizumab (Pre-Tx) and various weeks after initiating treatment with eculizumab. The concentration of plasma F1+2 was also measured in the plasma from normal, healthy individuals (normals).
Figure 3B:
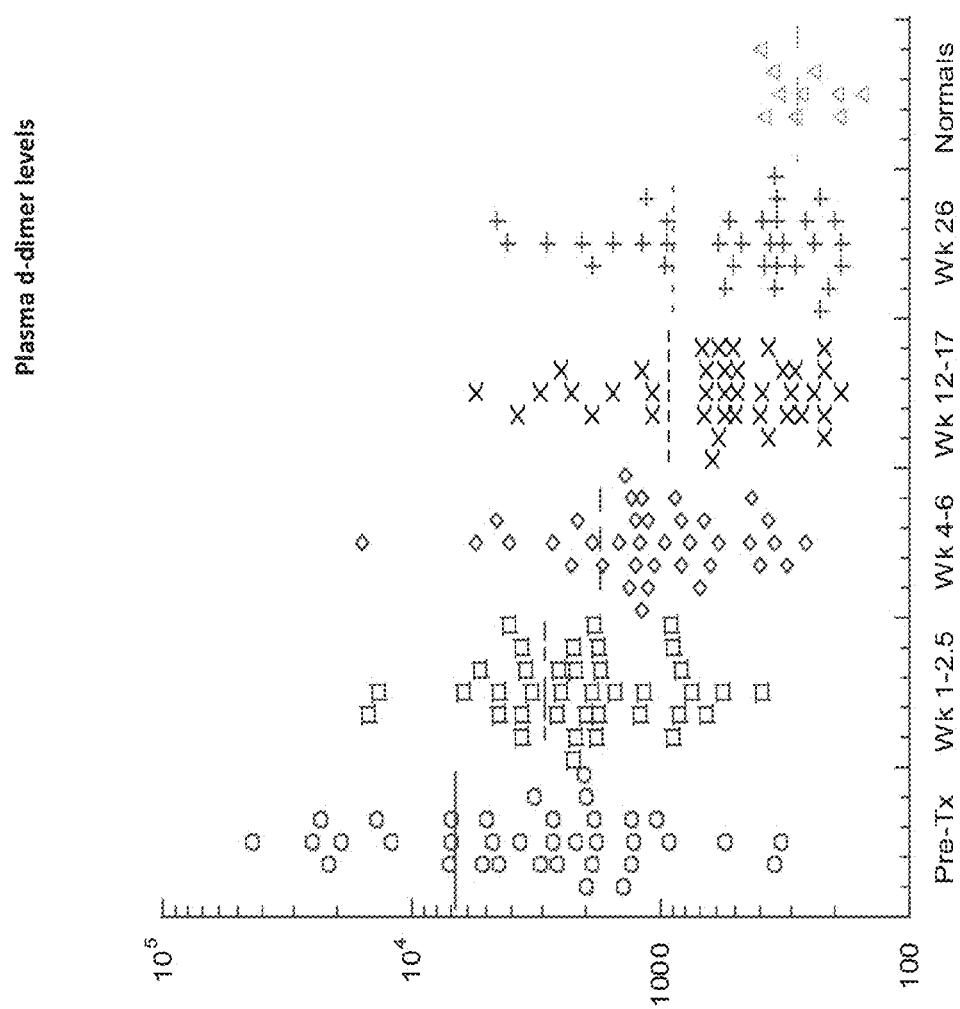
FIG. 3B is a dot plot depicting the concentration of D-dimer (in µg/L) in the plasma of aHUS patients both before treatment with eculizumab (Pre-Tx) and various weeks after initiating treatment with eculizumab. The concentration of plasma D-dimer was also measured in the plasma from normal, healthy individuals (normals).
Figure 3D:
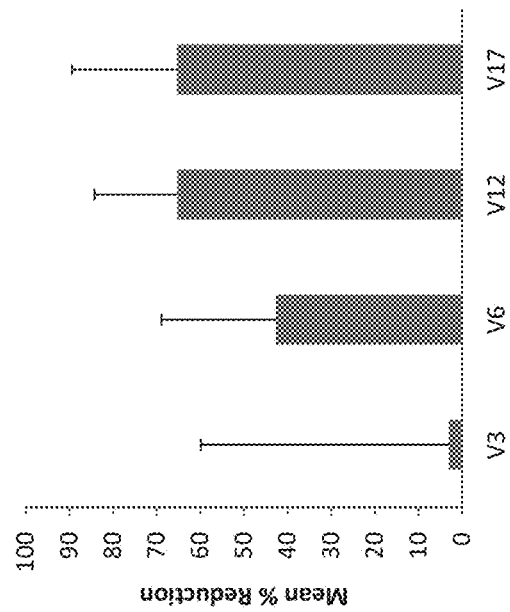
FIG. 3D is a bar graph depicting the mean percentage (%) reduction in plasma d-dimer levels (Y-axis) over time in aHUS patients post initiation of treatment with eculizumab. The x-axis indicates the week of the aHUS patient visit for evaluation post-initiation of treatment, e.g., V3 is the patient visit for evaluation at week 3 post-initiation of treatment.

As summarized in Table 3 below, relative to the concentration in a sample of biological fluid from healthy volunteers, the serum concentration of sCD40L and the plasma levels of prothrombin fragment 1+2 and D-dimer were significantly elevated in the majority of aHUS patients. See also FIGS. 3A-B.

TABLE 3

| aHUS Biomarker Protein | n/N (%) elevated at baseline | P-value |
|---|---|---|
| sCD40L | 36/38 (94.7) | <0.0001 |
| Prothrombin Fragment F1 + 2 | 36/38 (94.7) | <0.0001 |
| D-dimer | 34/36 (94.4) | =0.0002 |

* "N" indicates the total number of patients evaluated for a given biomarker, and "n" indicates the number of those "N" patients with elevated levels of the biomarker protein.

The release of sCD40L is generally associated with platelet metabolism and activity. Prothrombin fragments F1+2 are generated during conversion of prothrombin to thrombin, whereas D-dimer is a fibrin degradation product indicating fibrinolysis.

Figure 3C:
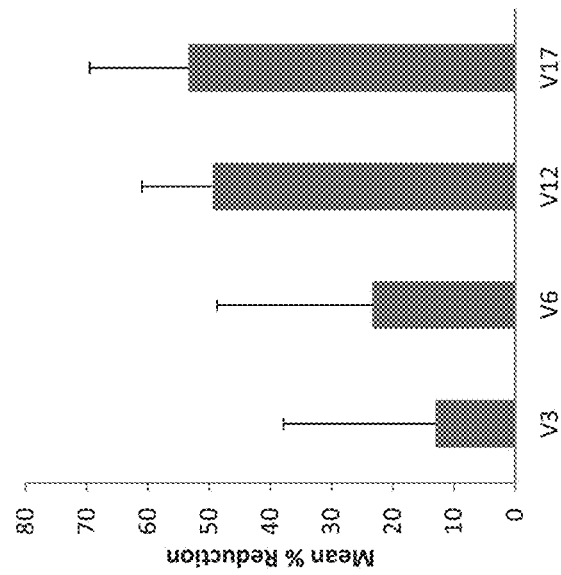
FIG. 3C is a bar graph depicting the mean percentage (%) reduction in plasma prothrombin fragment F1+2 levels (Y-axis) over time in aHUS patients post initiation of treatment with eculizumab. The x-axis indicates the week of the aHUS patient visit for evaluation post-initiation of treatment, e.g., V3 is the patient visit for evaluation at week 3 post-initiation of treatment.
Figure 4B:
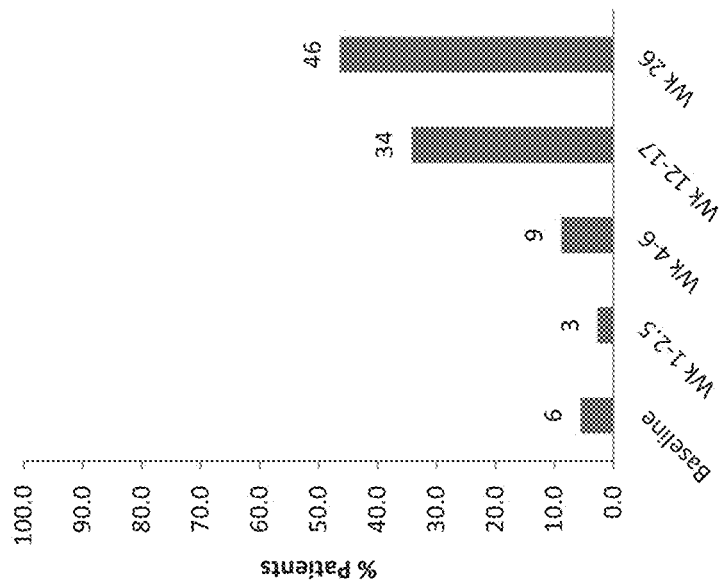
FIGS. 4A and 4B are bar graphs depicting the percentage of aHUS patients who achieve normalized concentrations of plasma prothrombin fragment 1+2 (FIG. 4A) and plasma D-dimer (FIG. 4B) at baseline (pre-treatment with eculizumab) and various weeks following initiation of treatment with eculizumab.
Figure 4A:
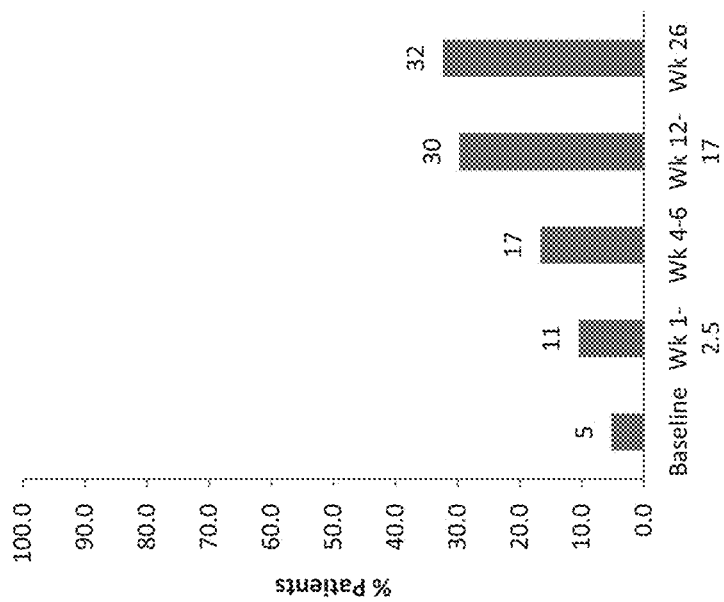

Following treatment with eculizumab, the mean levels (concentrations) of these aHUS biomarkers were reduced. The mean levels of plasma levels of F1+2 and D-dimer are reduced significantly at between 1 to 2.5 weeks (p=0.0078 and 0.0083, respectively) following initiation of treatment and remained so. As shown in FIG. 3C, the mean percentage reduction in F1+2 was around 15% by week 3 and over 50% by week 12. The mean percentage reduction in d-dimer levels was around 40% at week 6, but greater than 60% by week 12. These data indicate that eculizumab therapy has an immediate effect on the coagulation and fibrinolysis pathways. As shown in FIGS. 4A-B, 32% of treated aHUS patients exhibit normalization of F1+2 levels by week 26 post-initiation of treatment and 46% of the patients have normalized levels of D-dimer. By contrast, sCD40L levels remained elevated throughout the study.

Markers of Endothelial Cell Damage and/or Activation

As summarized in Table 4 below, relative to the concentration in sample of biological fluid from healthy volunteers, the plasma concentration of thrombomodulin and vWF and the serum concentration of VCAM-1 were significantly elevated in aHUS patients. See also FIGS. 5A-C.

TABLE 4

| aHUS Biomarker Protein | n/N (%) elevated at baseline | P value |
|---|---|---|
| Thrombomodulin | 33/34 (97.1) | <0.0001 |
| VCAM-1 | 36/38 (94.7) | <0.0001 |
| Von Willebrand Factor Antigen | 15/38 (39.5) | <0.02 |

* "N" indicates the total number of patients evaluated for a given biomarker, and "n" indicates the number of those "N" patients with elevated levels of the biomarker protein.
n.s. indicates not significant.

High concentration of thrombomodulin and VCAM-1 in biological fluids of aHUS patients indicates significant endothelial cell activation. Thrombomodulin is released in response to C3a, which further underscores ongoing complement activation in aHUS patients. vWF concentration is also significantly elevated. vWF has a number of physiological roles including platelet adhesion and coagulation and is also a marker of endothelial damage and activation.

Figure 5A:
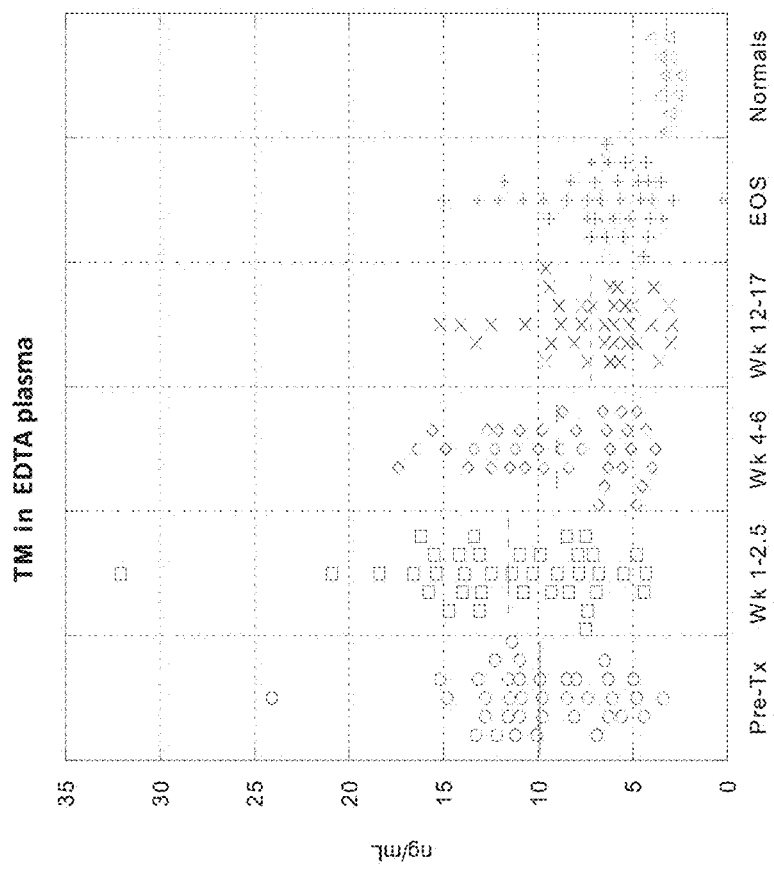
FIG. 5A is a dot plot depicting the concentration of thrombomodulin (in ng/mL) in the plasma (EDTA treated plasma) of aHUS patients both before treatment with eculizumab (Pre-Tx) and various weeks after initiating treatment with eculizumab. The concentration of plasma thrombomodulin was also measured in the plasma from normal, healthy individuals (normals). EOS designates the results of the analysis of samples obtained at the "end of study".
Figure 5B:
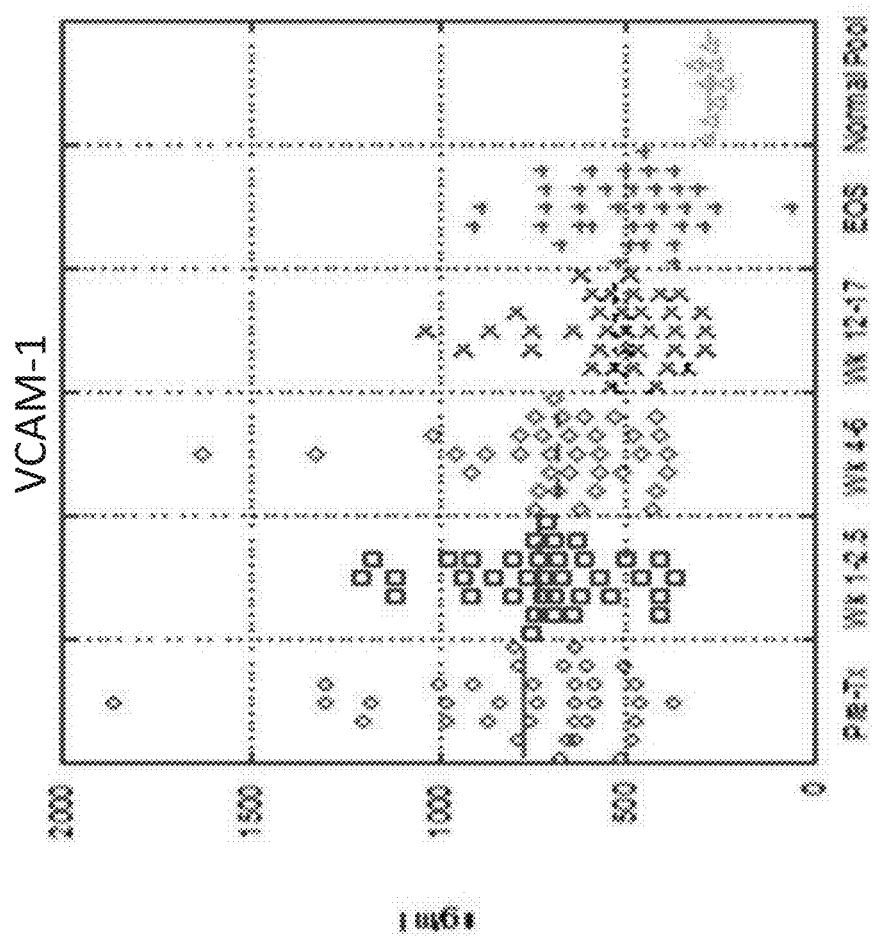
FIG. 5B is a dot plot depicting the concentration of VCAM-1 (in ng/mL) in the serum of aHUS patients both before treatment with eculizumab (Pre-Tx) and various weeks after initiating treatment with eculizumab. The concentration of serum VCAM-1 was also measured in the serum from normal, healthy individuals (normal pool). EOS designates the results of the analysis of samples obtained at the "end of study".
Figure 5C:
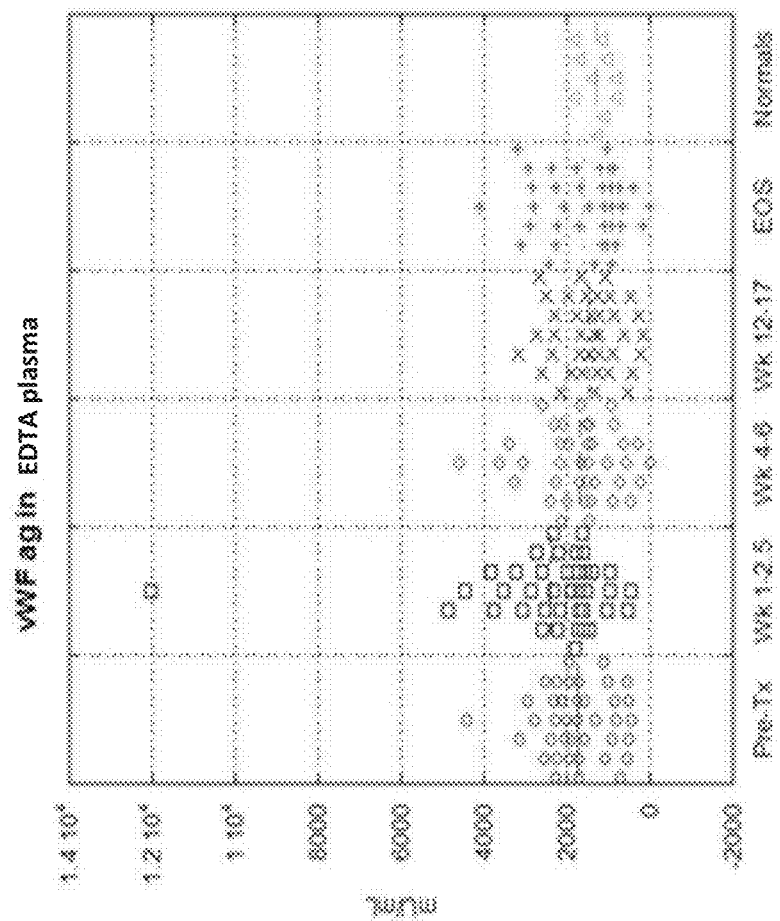
FIG. 5C is a dot plot depicting the activity of vWF (in mU/mL) in the plasma (EDTA treated plasma) of aHUS patients both before treatment with eculizumab (Pre-Tx) and various weeks after initiating treatment with eculizumab. The activity of vWF was also measured in the plasma from normal, healthy individuals (normals). EOS designates the results of the analysis of samples obtained at the "end of study".
Figures 6A, 6B:
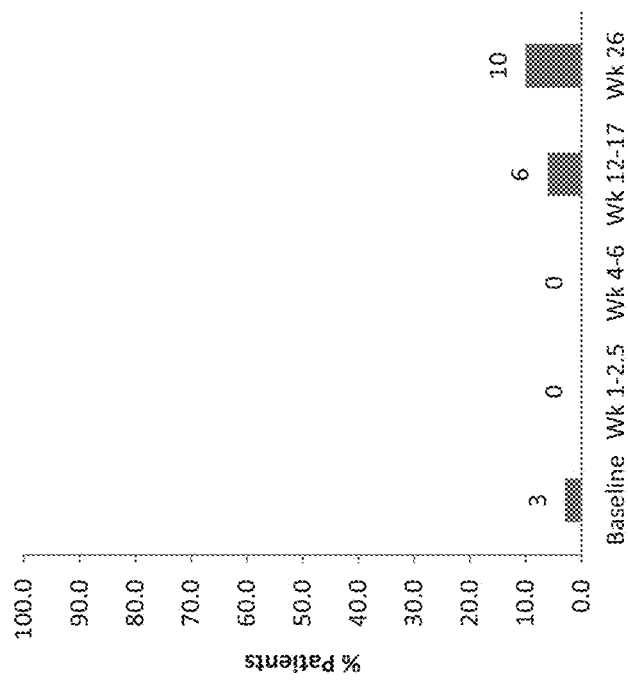
FIGS. 6A and 6B are bar graphs depicting the percentage of aHUS patients that achieve normalized plasma thrombomodulin concentrations (FIG. 6A) and plasma vWF activity levels (FIG. 4B) at baseline (pre-treatment with eculizumab) and various weeks following initiation of treatment with eculizumab.

Following treatment with eculizumab, the mean levels (concentrations) of these aHUS biomarkers were reduced (FIGS. 5A-C). The mean levels of thrombomodulin and VCAM-1 were reduced significantly from baseline by week 17 (p=0.0007 and <0.0001, respectively) following initiation of treatment (see FIGS. 6C and 6D). By week 26, levels of VCAM-1 and vWF had also been reduced. However, while vWF normalized in ~70% of treated aHUS patients by week 17 post-initiation of treatment (FIG. 6B), thrombomodulin and VCAM-1 levels remained elevated. Interestingly, of the 10% of patients who normalized thrombomodulin levels (FIG. 6A), only one patient had both normalized thrombomodulin and vWF levels. These data indicate that eculizumab therapy has a rapid and robust positive effect to correct endothelial cell damage and activation.

Markers of Inflammation

Table 5 (below) sets forth a series of analytes detected in plasma and/or serum and indicates the percentage of aHUS patients in which the respective analytes were elevated prior to treatment with complement inhibitor therapy.

TABLE 5

| aHUS Biomarker Protein | n/N (%) elevated at baseline | P value |
|---|---|---|
| Serum CXCL10 | 23/38 (60.5) | P < 0.0001 |
| Serum CXCL9 | 33/38 (86.8) | P < 0.0001 |
| IL-18 | 19/38 (50.0) | P < 0.0001 |
| MCP-1 | 34/38 (89.5) | P < 0.0001 |
| TNFR1 | 38/38 (100.0) | P < 0.0001 |
| VEGF | 25/38 (65.8) | P < 0.0001 |
| IL-6 | 21/34 (61.8) | P = 0.0019 |
| CCL5 | 4/38 (10.5) | P = 0.0045 |
| IFN-γ | 5/34 (14.7) | P = 0.0353 |
| IL-8 | 22/38 (57.9) | n.s. (P = 0.0640) |
| ICAM-1 | 2/34 (5.9) | n.s |
| IL-1β | 1/38 (2.6) | n.s |
| IL-12p70 | 2/34 (5.9) | n.s |

* "N" indicates the total number of patients evaluated for a given biomarker, and "n" indicates the number of those "N" patients with elevated levels of the biomarker protein.
** The concentrations of the two analytes marked as "Serum" were measured in serum. The concentrations of all other analytes in the Table were measured in plasma.
n.s. indicates not significant.

Figures 7A, 7B:
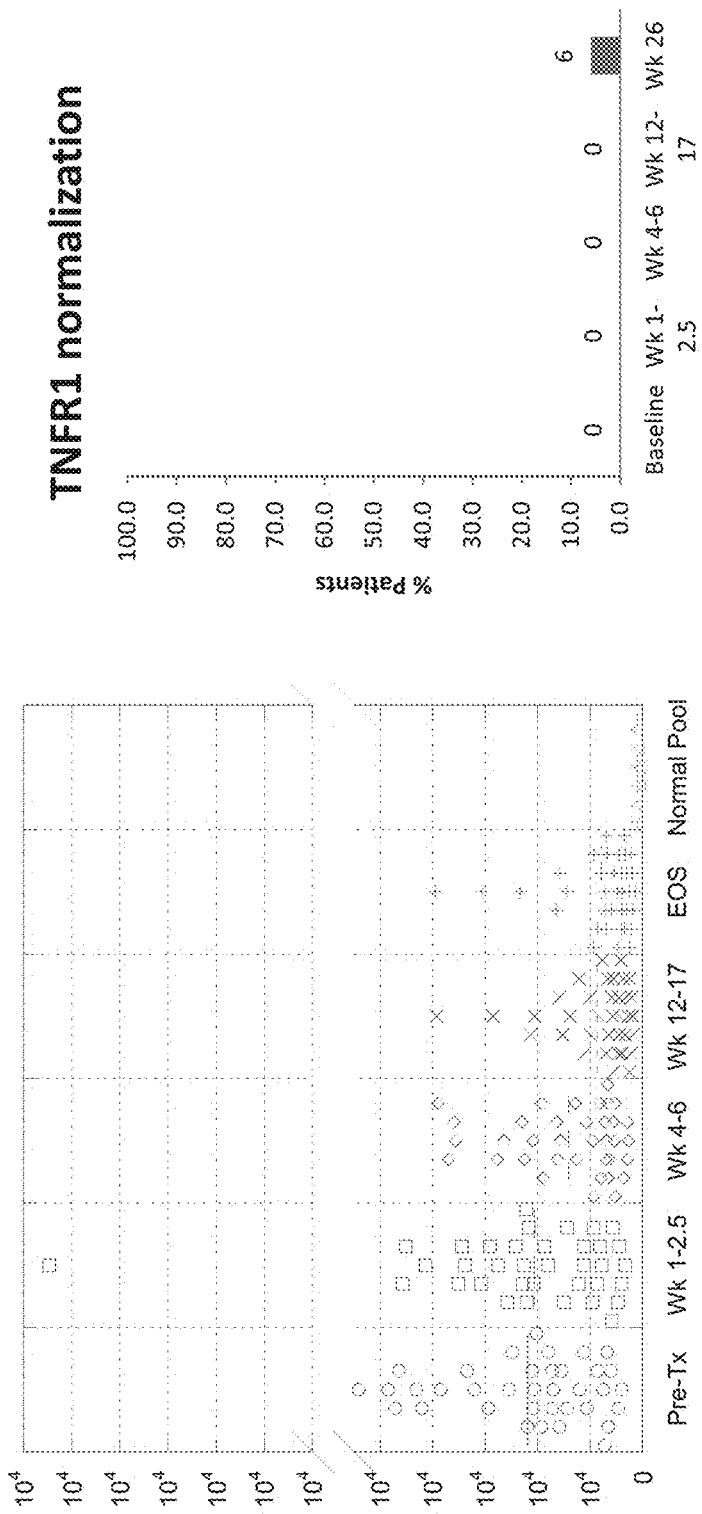
FIG. 7A is a dot plot depicting the concentration of TNFR1 (in pg/mL) in the serum of aHUS patients both before treatment with eculizumab (Pre-Tx) and various weeks after initiating treatment with eculizumab. The concentration of serum TNFR1 was also measured in the serum from normal, healthy individuals (normal pool). EOS designates the results of the analysis of samples obtained at the "end of study".
FIG. 7B is a bar graph depicting the percentage of aHUS patients that achieve normalized serum TNFR1 concentrations at baseline (pre-treatment with eculizumab) and various weeks following initiation of treatment with eculizumab.

Prior to therapy with eculizumab, patients with aHUS had elevated levels of circulating inflammatory cytokines and chemokines including, e.g., CXCL-10, CXCL-9, IL-18, TNFR1, MCP-1, VEGF, IL-6, and IL-8. Following initiation of treatment, however, TNFR1 was the earliest inflammatory marker to be significantly reduced (by week 6, p=0.0012) (FIG. 7A). Mean concentration of TNFR1 remained significantly lower than baseline at all subsequent visits (P<0.0001), but only normalized in 6% of aHUS patients (FIG. 7B). Similarly, mean levels of CXCL10 were significantly reduced by week 26 (p=0.0055), but did not normalize in all aHUS patients (31% of patients did not normalize). By week 26, mean levels of IFN-γ normalized in approximately 50% of patients; however, mean levels of serum IL-8 (p=0.01), CXCL-9 (p=0.01), IL-18 (p<0.0001) and VEGF (p<0.0001) remained elevated in most aHUS patients, as compared to normal controls, and not significantly different from baseline. Serum IL-6 was significantly reduced (p=0.04) from baseline at week 26 and remained elevated at week 26 as compared to normal control.

By contrast, mean levels of CCL-5 were elevated significantly by week 17 post-initiation of treatment and thereafter (p=0.0072 and 0.0021 at weeks 12-17 and week 26, respectively). In response to vascular injury in mice, CCL5 is upregulated, which promotes selective T cell infiltration as part of a vascular wound-healing response. See, e.g., Rook-maaker et al. (2007) *Am J Physiol Renal Physiol* 293(2): F624-630. These data indicate that eculizumab therapy has a rapid and robust positive effect on inflammation in many patients with aHUS, but that low level inflammation may exist in these patients even during treatment.

Markers of Renal Tubular and Glomerular Injury

Table 6A (below) sets forth a series of analytes detected in urine collected from patients and indicates the percentage of aHUS patients in which the respective analytes were elevated prior to treatment with complement inhibitor therapy.

TABLE 6A

| Biomarker | n/N (%) elevated at baseline | P value |
|---|---|---|
| Beta-2 Microglobulin (β2M) | 20/28 (71.4) | P < 0.0001 |
| Clusterin | 24/29 (82.8) | P < 0.0001 |
| Cystatin C | 18/29 (62.1) | P = 0.0002 |
| TIMP-1 | 22/29 (75.9) | P = 0.0003 |
| FABP-1 | 22/29 (75.9) | P = 0.0130 |
| NGAL | 5/29 (17.2) | P = 0.0151 |
| NAG | 3/23 (13.0) | P = 0.0413 |
| CXCL10 | 2/29 (6.9) | n.s. |
| CXCL9 | 2/29 (6.9) | n.s. |
| KIM-1 | 2/29 (6.9) | n.s. |

* "N" indicates the total number of patients evaluated for a given biomarker, and "n" indicates the number of those "N" patients with elevated levels of the biomarker protein. n.s. indicates not significant.

Figure 8A:
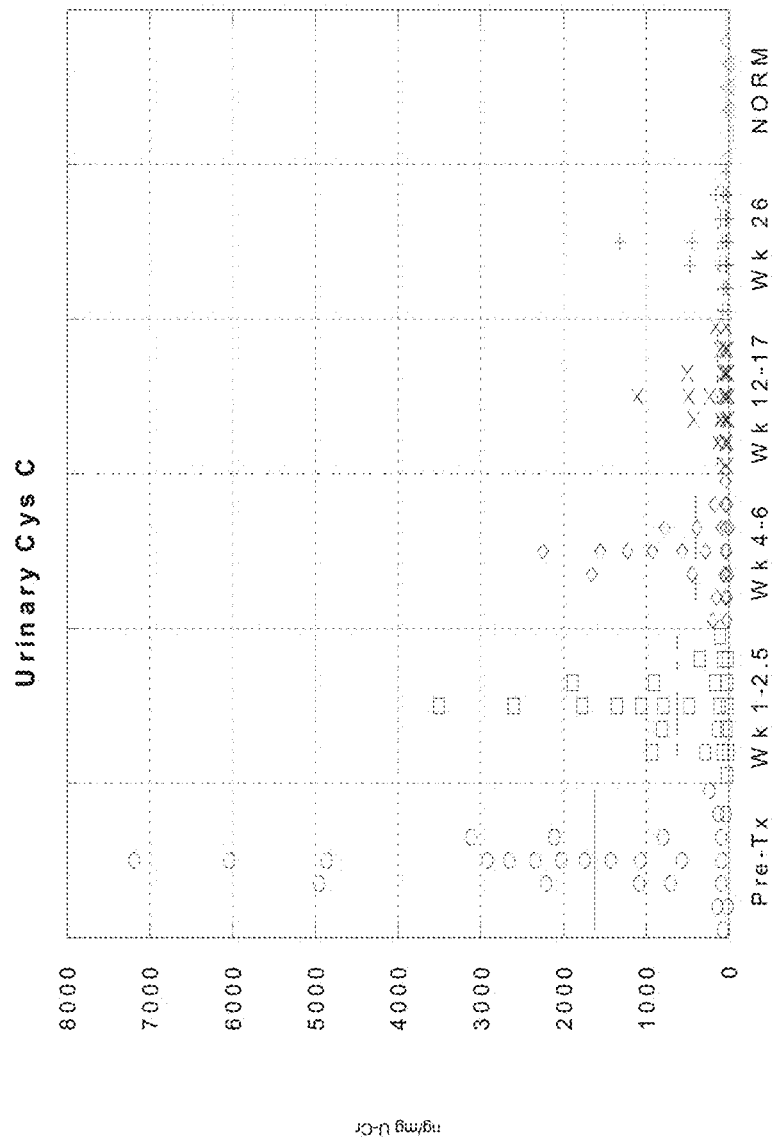
FIG. 8A is a dot plot depicting the concentration of cystatin C (CysC) (in ng/mg of urinary creatine) in the urine of aHUS patients both before treatment with eculizumab (Pre-Tx) and various weeks after initiating treatment with eculizumab. The concentration of urinary CysC was also measured in the urine from normal, healthy individuals (NORM).
Figure 8B:
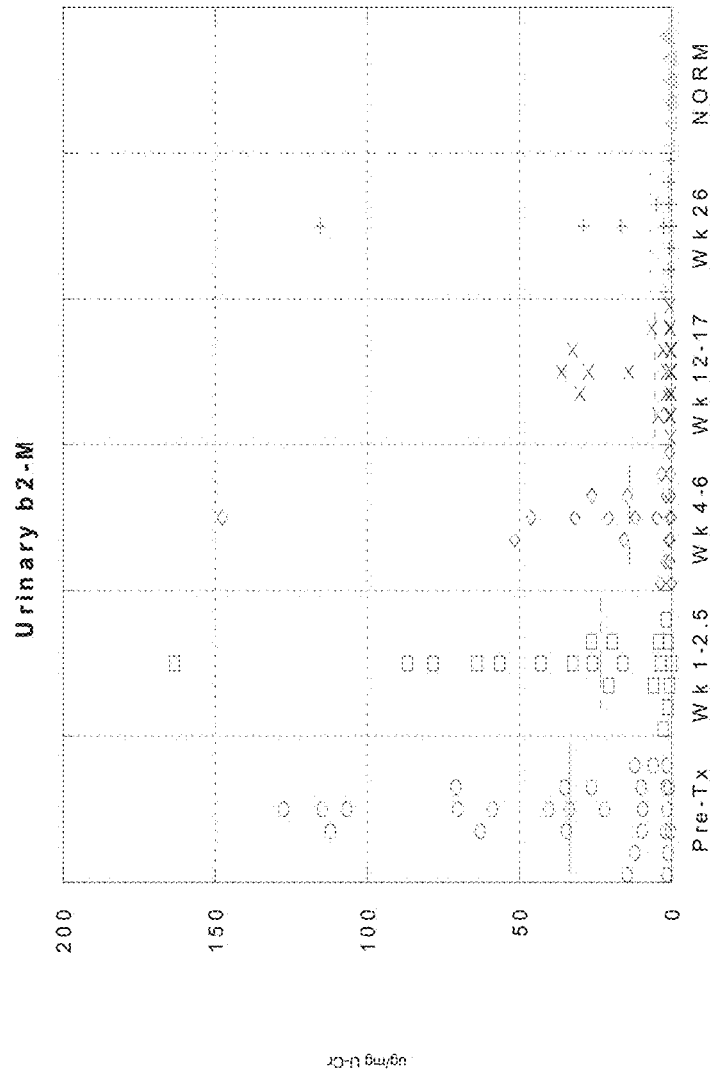
FIG. 8B is a dot plot depicting the concentration of β2M (in µg/mg of urinary creatine) in the urine of aHUS patients both before treatment with eculizumab (Pre-Tx) and various weeks after initiating treatment with eculizumab. The concentration of urinary β2M was also measured in the urine from normal, healthy individuals (NORM).
Figure 8C:
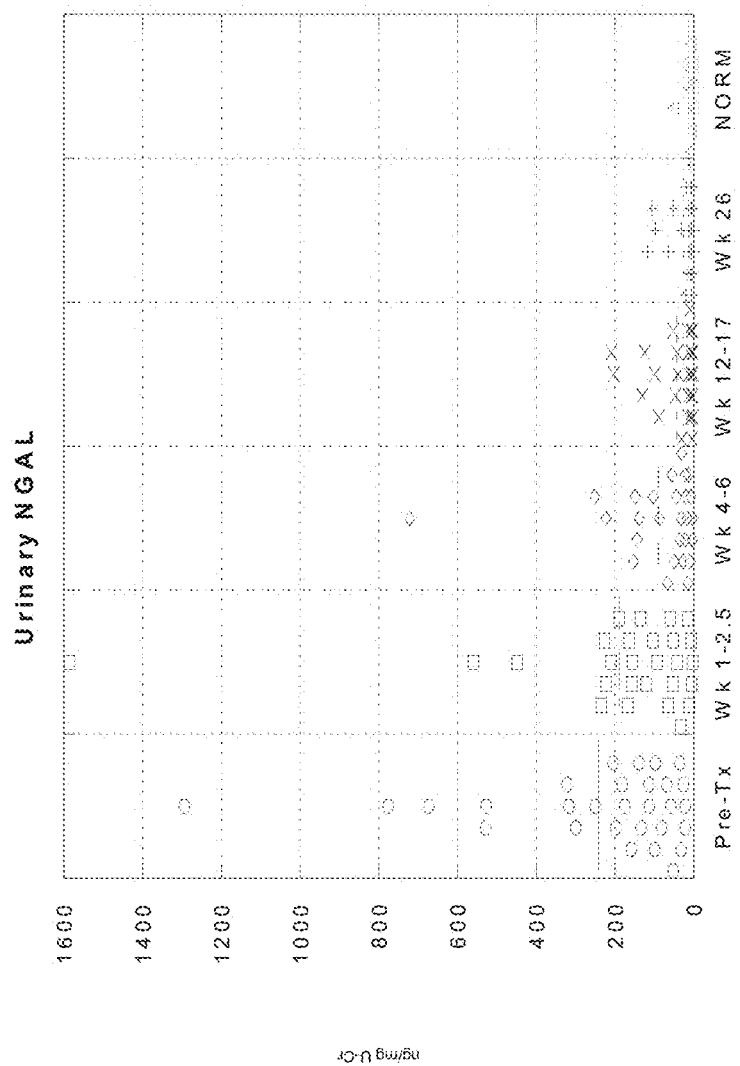
FIG. 8C is a dot plot depicting the concentration of NGAL (in ng/mg of urinary creatine) in the urine of aHUS patients both before treatment with eculizumab (Pre-Tx) and various weeks after initiating treatment with eculizumab. The concentration of urinary NGAL was also measured in the urine from normal, healthy individuals (NORM).
Figure 9E:
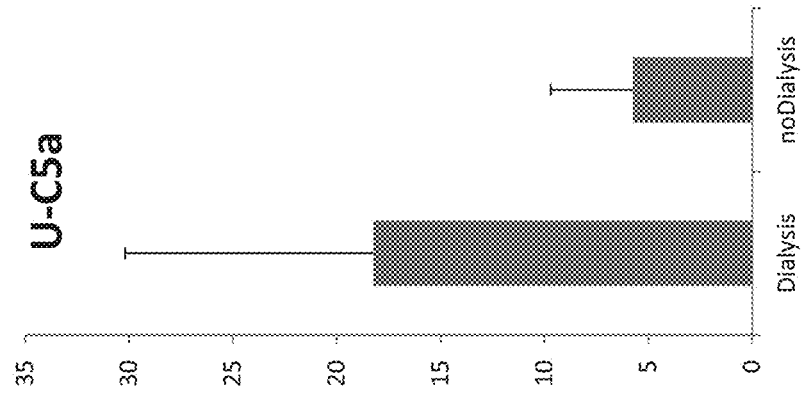
Figure 9D:
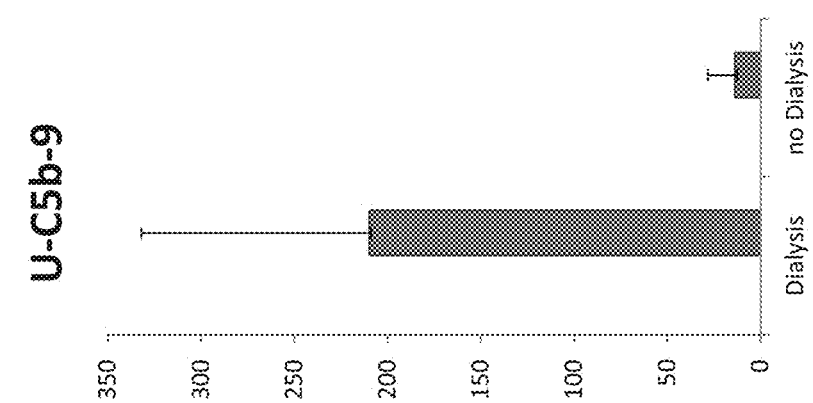
Figure 9C:
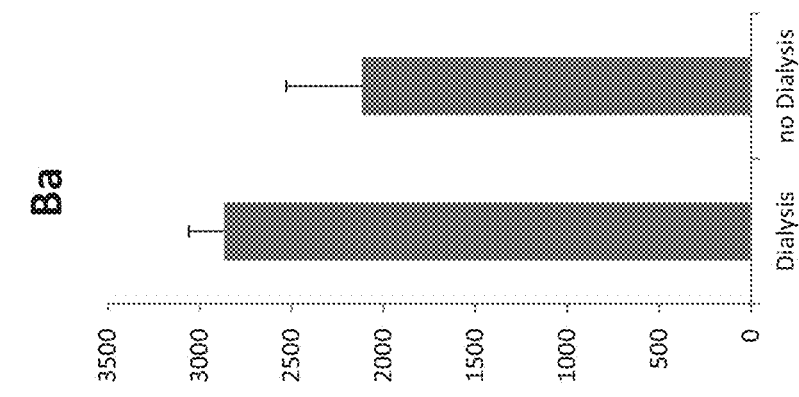

Prior to treatment with eculizumab, low molecular weight molecules that are normally filtered by the kidney were elevated in the urine of patients with aHUS including β2M, clusterin, cystatin C, and NAG. Molecules produced by renal tubular epithelial cells in response to injury were also elevated, such as TIMP-1, NGAL and L-FABP. However, following treatment with eculizumab, CysC (p=0.0012) (FIG. 8A), clusterin (p=0.0446), and TIMP-1 (p=0.0353) are significantly reduced by 1-2.5 weeks post-initiation of treatment and they remained significantly reduced throughout the course of the study. NGAL (p=0.0003) (FIG. 8C), L-FABP (p=0.0366), and NAG (p=0.0369) were significantly reduced from baseline by 4-6 weeks post-initiation of treatment and remained so thereafter. β2M was significantly reduced at 12-17 weeks (p=0.0008) and onwards (FIG. 8B). By week 26, mean urinary levels of all analytes had normalized in treated aHUS patients.

These data indicate that eculizumab therapy has a rapid, robust, and durable positive effect redressing renal tubular and glomerular injury experienced by many patients with aHUS.

Summary

The following Table provides a summary of exemplary aHUS biomarkers (though not an exhaustive list), which are elevated in aHUS patients prior to treatment with eculizumab, but are significantly reduced following treatment with eculizumab. Also provided in the Table (Table 6B) is the average time post-initiation of treatment with eculizumab in which significant reduction of the aHUS biomarker occurred.

TABLE 6B

| Biomarker | Week 1-2.5 | Week 4-6 | Week 12-17 | Week 26 |
|---|---|---|---|---|
| U-C5a | X | | | |
| U-C5b-9 | X | | | |
| F1 + 2 | X | | | |
| D-dimer | X | | | |
| U-Cys-C | X | | | |
| U-TIMP-1 | X | | | |
| Plasma Ba | | X | | |
| TNFR1 | | X | | |

TABLE 6B-continued

| Biomarker | Week 1-2.5 | Week 4-6 | Week 12-17 | Week 26 |
|---|---|---|---|---|
| U-CLU | | X | | |
| U-NGAL | | X | | |
| Thrombomodulin | | | X | |
| VCAM | | | X | |
| L-FABP | | | X | |
| B2M | | | X | |
| CXCL10 | | | | X |
| IFN-γ | | | | X |

Baseline aHUS Marker Levels in aHUS Patients Receiving Dialysis and/or Receiving Kidney Transplant Also assessed were the concentration of plasma and urine complement, inflammation, and renal injury markers in aHUS patients who received dialysis prior to therapy with eculizumab. As shown in Table 7 (below), the mean concentration of serum TNFR1, plasma Ba, C5b9, prothrombin fragments 1+2, β2M, clusterin, sC5b9, TIMP-1, NGAL, CysC, and C5a were significantly elevated in aHUS patients who underwent repeated dialysis (e.g., two or more times within 6 months prior to treatment) as compared to aHUS patients that did not undergo repeated dialysis prior to enrollment in the study (prior to treatment). See also FIGS. 9A-E.

TABLE 7

| Analyte | Higher with Repeated Dialysis |
|---|---|
| TNFR1 (serum) | p =< 0.0001 |
| β2m (urinary) | p = 0.0009 |
| Clusterin (urinary) | p = 0.0020 |
| Ba (plasma) | p = 0.0021 |
| C5b-9 (urinary) | p = 0.0042 |
| TIMP-1 (urinary) | p = 0.0070 |
| NGAL (urinary) | p = 0.0110 |
| CysC (urinary) | p = 0.020 |
| F1 + 2 (plasma) | p = 0.0191 |
| C5b-9 (plasma) | p = 0.0476 |
| C5a (urinary) | p = 0.0477 |

** The concentration of the one analyte marked "serum" was measured in serum. The concentration of analytes designated with "urinary" was measured in urine, whereas the concentration of analytes labeled with "plasma" was measured in plasma obtained from the patients.

In addition, aHUS patients who had received a kidney transplant prior to treatment with eculizumab had lower urinary C5b-9 and urinary FABP-1 at baseline as compared to patients who had not received a kidney transplant.

Baseline aHUS Marker Levels Vis-à-Vis TMA Markers

Figure 14:
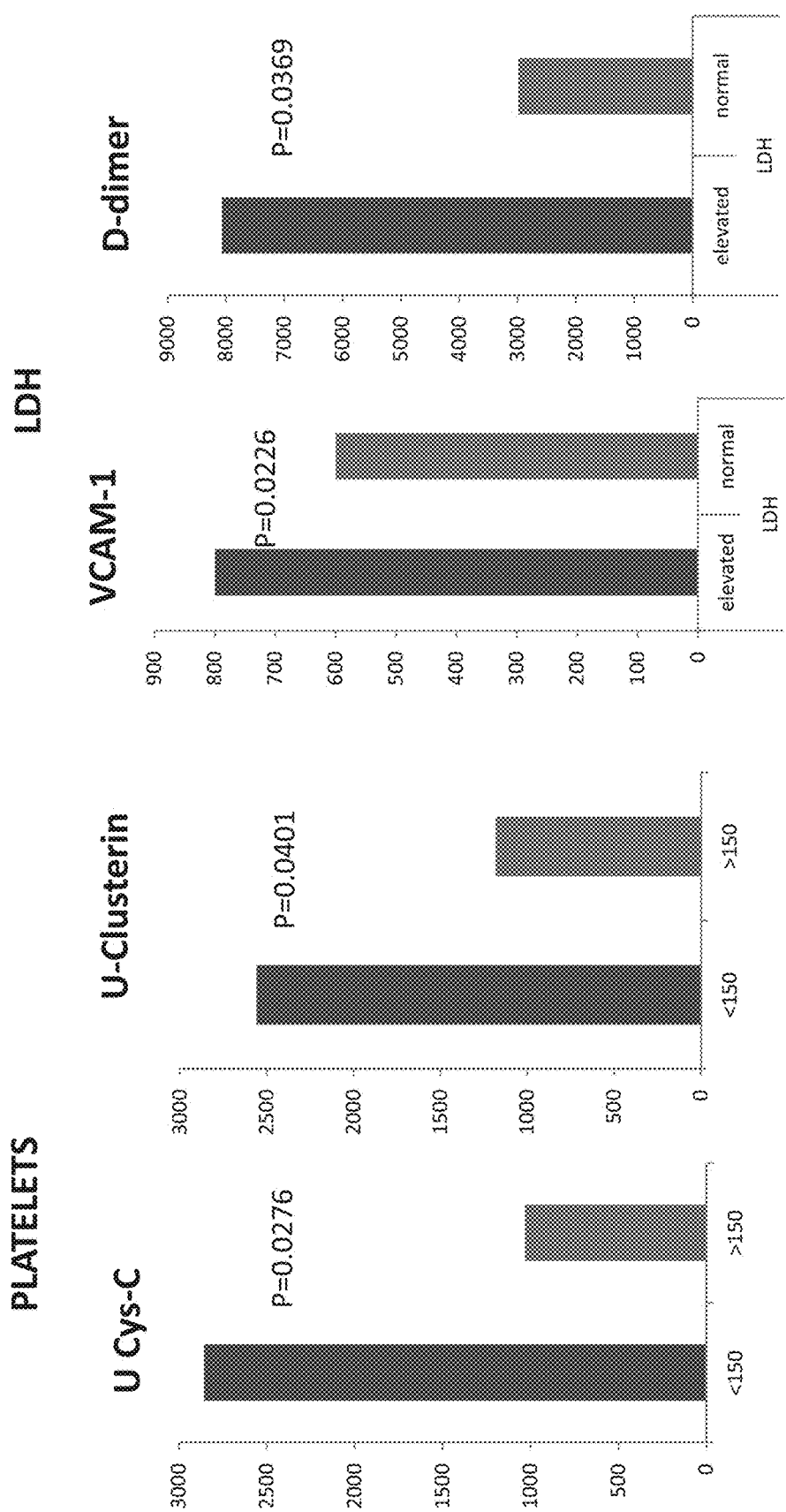
FIGS. 14A-14D are a series of bar graphs depicting the observation that certain aHUS-associated biomarkers are elevated in aHUS patients with abnormal TMA markers at baseline.

Levels of some aHUS-associated biomarkers in some aHUS patients correlated with abnormal thrombotic microangiopathy (TMA) markers such as reduced platelet counts, elevated LDH, and increased haptoglobin levels. For example, aHUS patients with reduced platelet counts at baseline (<150,000 per μL of blood), exhibited elevated levels of urinary cystatin C (P=0.0276) and urinary clusterin (P=0.0401). See FIGS. 14A-B. aHUS patients having elevated LDH levels exhibited increased levels of VCAM-1 (P=0.0226) (FIG. 14C), d-dimer (P=0.0369) (FIG. 14D), IL-18, thrombomodulin, and TNFR1 (see below). Elevated haptoglobin levels were often present in aHUS patients having elevated IL-18 levels.

Figure 15:
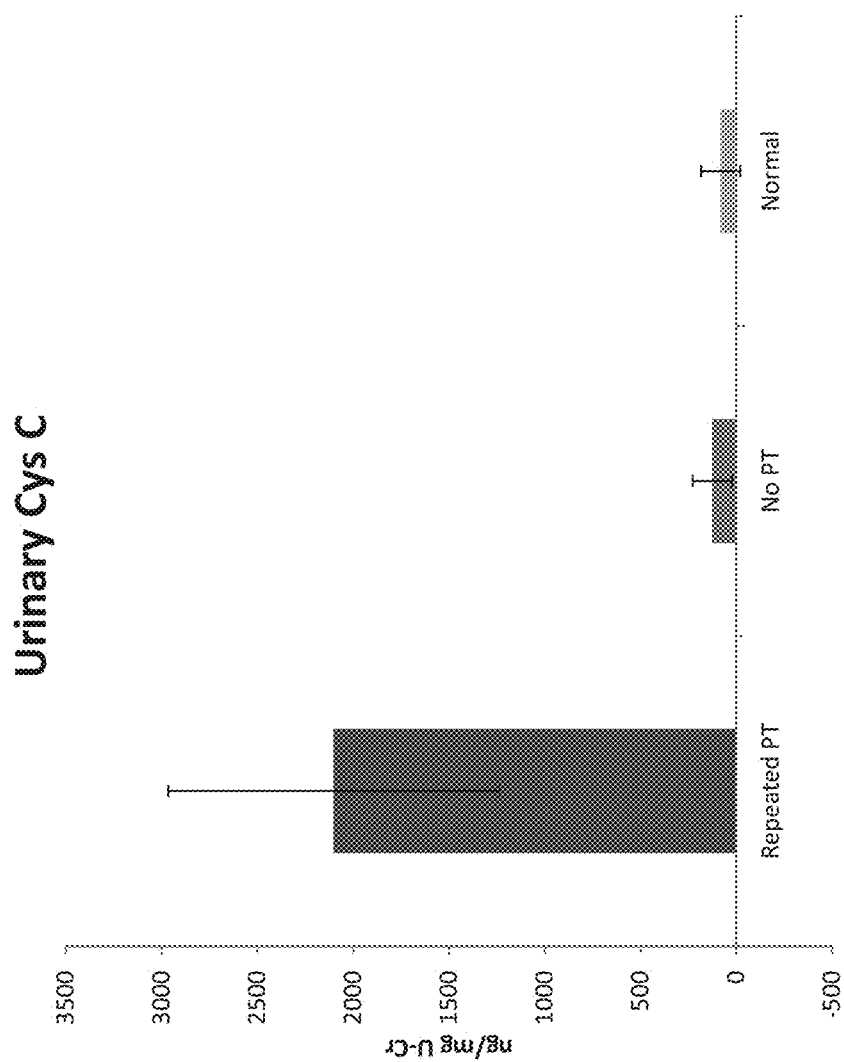
FIG. 15 is a bar graph depicting the level of cystatin C (ng/mg of urinary creatine) in the urine of aHUS patients at baseline having repeated plasma therapy (Repeated PT; N=23), no plasma therapy (No PT; N=3), or in normal patients (N=9).

Baseline aHUS Marker Levels in aHUS Patients Receiving Plasma Therapy aHUS patients with repeated plasma therapy prior to treatment with eculizumab exhibited higher mean levels of urinary cystatin C at baseline (see FIG. 15).

Correlations Between Biomarker Levels and Clinical Parameters

Platelets

An elevated level of CCL5 was positively correlated with higher platelet counts at baseline (p=<0.0001; cc (correlation coefficient)=0.8106). An elevated level of sCD40L was also correlated with higher platelet counts at baseline (p=<0.001; cc=0.6313).

Figure 13:
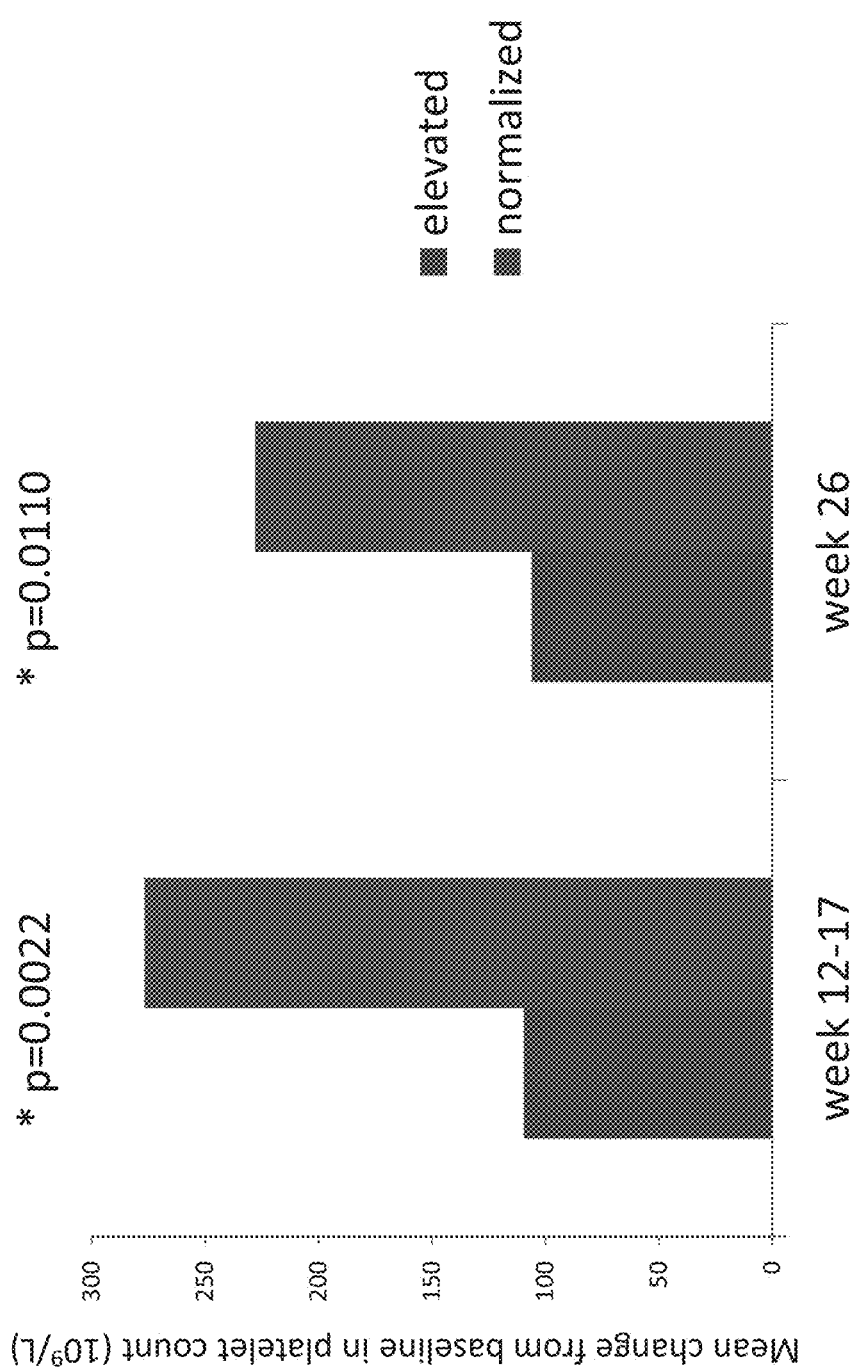
FIG. 13 is bar graph depicting the mean change from baseline (initial visit, prior to treatment with eculizumab) in platelet count ($10^9$/L) at weeks 12-17 and week 26 post initiation of treatment with eculizumab in aHUS patients with normalized levels of plasma Ba versus persistently elevated plasma Ba levels. The p values for each observation are also provided in the figure.

Moreover, patients with normalized Ba levels following eculizumab treatment show significantly higher platelet increases than patients whose Ba levels remain elevated following treatment. See FIG. 13.

Estimated Glomerular Filtration Rate (eGFR), LDH, and Urinary Complement

A correlation was also observed between elevated plasma Ba levels and reduced eGFR (p<0.0001; cc=−0.7219). An elevated concentration of TNFR1 in serum of aHUS patients prior to treatment was correlated with lactate dehydrogenase (LDH) levels (p=0.027; cc=0.3586), but more significantly correlated with lower eGFR (p<0.0001; cc=−0.6134). In addition, higher levels of urinary complement components C5a and sC5b-9 and renal injury markers (ß2M, clusterin, cystatin C, NGAL, and TIMP-1) were moderately correlated with lower eGFR (p=0.0002 to 0.0242; cc=−0.4286 to −0.6714).

Elevated levels of urinary sC5b-9, clusterin, and TIMP-1 were modestly correlated with proteinuria (p=0.0086 to 0.0284; cc=0.40 to 0.4788), whereas elevated levels of plasma Ba (p=0.0017; cc=0.517), β2M, clusterin, urinary sC5b-9, and cystatin C were correlated with increased creatinine in the urine of patients prior to treatment with eculizumab (p=0.0440-0.0018; cc=0.3982-0.6457).

First Clinical Presentation of aHUS

Also observed was a correlation between patients experiencing their first aHUS manifestation and significantly elevated plasma D-dimer levels or urinary FABP-1 at baseline (prior to eculizumab treatment) (see Table 8).

TABLE 8

| Biomarker | Biomarker Elevated (n %) | | |
|---|---|---|---|
| | Single aHUS Manifestation | Multiple Manifestations | p-value |
| Plasma D-dimer (µg/L) | 27 (100.0) | 7 (77.8) | 0.0571 |
| Urine FABP-1 (ng/mg normalized to creatinine) | 19 (90.5) | 3 (37.5) | 0.0079 |

Smoldering Disease

Figure 10A:
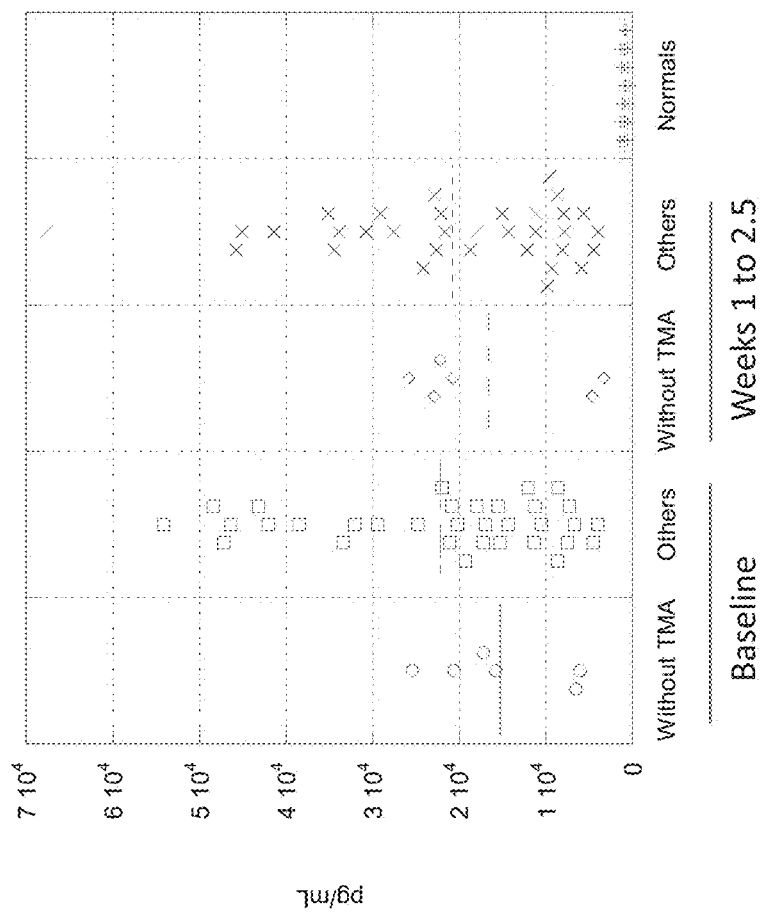
FIG. 10A is a dot plot depicting the concentration of serum TNFR1 (in pg/mL) in aHUS patients exhibiting stable clinical parameters (clinical remission) (Without TMA) and those aHUS patients that continue to experience elevated haptoglobin and LDH levels (and reduced platelet counts) (Others), both at baseline and at 1 to 2.5 weeks post initiation of treatment with eculizumab. Also shown are the concentrations of serum TNFR1 from normal, healthy individuals (Normals).

Six of the aHUS patients involved in the study presented at enrollment with normalized hematologic parameters (including haptoglobin, LDH, and platelet levels). However, these patients still showed evidence of chronic inflammation and complement activation despite a stable clinical picture. The patients had significantly elevated levels of serum TNFR1 (as shown in FIG. 10A) as well as significantly elevated levels of thrombomodulin, Ba (FIG. 10B), prothrombin fragments 1+2 (FIG. 10E), VCAM-1 (FIG. 10C), and d-dimer (FIG. 10D). Similarly, patients with normal (>150×10$^9$ platelets/µL) platelet levels at baseline still show elevated levels of most biomarkers (e.g., Ba (FIG. 10F), VCAM-1 (FIG. 10G), D-dimer (FIG. 10H), and F1+2 (FIG. 10I). Taken together, these findings indicate that, even for the subset of aHUS patients deemed to be in clinical remission following treatment, there are likely ongoing low levels of complement activity, coagulopathy, and inflammation.

Correlations Between Biomarker Levels and Clinical Outcomes

Hematologic Responses

Figure 11:
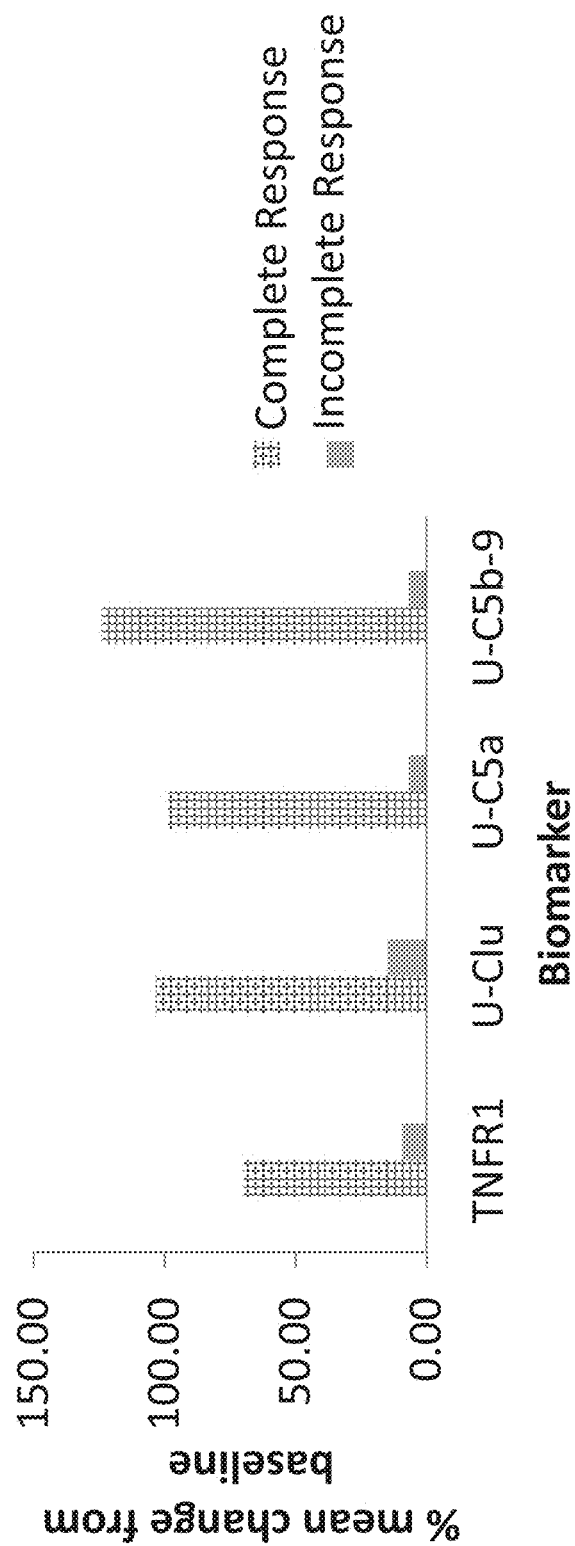
FIG. 11 is a bar graph depicting the mean percentage change in serum TNFR1 and urinary clusterin, C5a, and C5b9 levels in those aHUS patients who achieve a complete TMA response and those patients who still experience TMA events (incomplete response). (As noted and elaborated on in the working examples, a complete TMA response refers to a normalization of hematologic parameters and preservation of renal function.)

Patients with complete hematologic responses show more dramatic reductions in TNFR1, urinary clusterin, and urinary complement levels (C5a and C5b-9) (FIG. 11). For example, 86% of patients exhibiting a reduced concentration of these aHUS biomarker proteins attained a complete hematologic response (normalization of platelets and LDH) by weeks 12-17 post-initiation of treatment with eculizumab. Moreover, these patients showed a greater mean percentage reduction in serum TNFR1, urinary clusterin, urinary C5a, and urinary C5b-9 than patients who did not attain a complete hematologic response.

Also observed was that the rapidity of reduction in TNFR1 (e.g., by week 12 as compared to week 17 or beyond) was correlated with complete hematologic response (p=0.0008). The rate of normalization of D-dimer was significantly associated with a complete hematologic response (p=0.0109; cc=6.26).

Furthermore, the data show that a significantly greater increase in platelet counts at weeks 12-17 (p=0.0022) and week 26 (p=0.0110) was achieved in eculizumab-treated aHUS patients having (at weeks 12-17 and week 26, respectively) normalized plasma Ba concentrations. Improvement in platelets was also correlated with a significant reduction in mean F1+2 levels at week 4-6 (P=0.0148; cc=−0.4087) and week 12-17 (P=0.0073; cc=−0.4396) and more modestly with a reduction in d-dimer levels at week 12-17 (P=0.0470; cc=−0.3381). Nevertheless, a subset of patients, despite demonstrating a greater increase in platelet counts at weeks four through 26, continued to exhibit significantly elevated levels of prothrombin fragments 1+2, thrombomodulin, urinary β2M, clusterin, TIMP-1, and cystatin C, suggesting ongoing underlying disease activity.

Analysis of the data collected from the study also revealed a correlation between the change in other biomarker protein concentration and platelet recovery. For example, the concentration of CCL5, MCP-1, and sCD40L were positively correlated with increased platelet counts in eculizumab-treated patients as shown in Table 9 below.

TABLE 9

| Week following initiation of treatment with eculizumab | Biomarker | P-value | Correlation coeff. |
|---|---|---|---|
| 1-2.5 | CCL-5 | p < 0.0001 | 0.7419 |
| | sCD40L | P = 0.0141 | 0.3950 |
| | VEGF | P = 0.0014 | 0.5002 |
| 4-6 | CCL-5 | p < 0.0001 | 0.7743 |
| | sCD40L | p < 0.0001 | 0.6818 |
| | MCP-1 | P = 0.0114 | 0.4169 |
| 12-17 | CCL5 | P = 0.0003 | 0.5656 |
| 26 | CCL-5 | p < 0.0001 | 0.7845 |
| | sCD40L | P = 0.0012 | 0.5398 |

Thrombomicroangiopathy (TMA)

Figure 12:
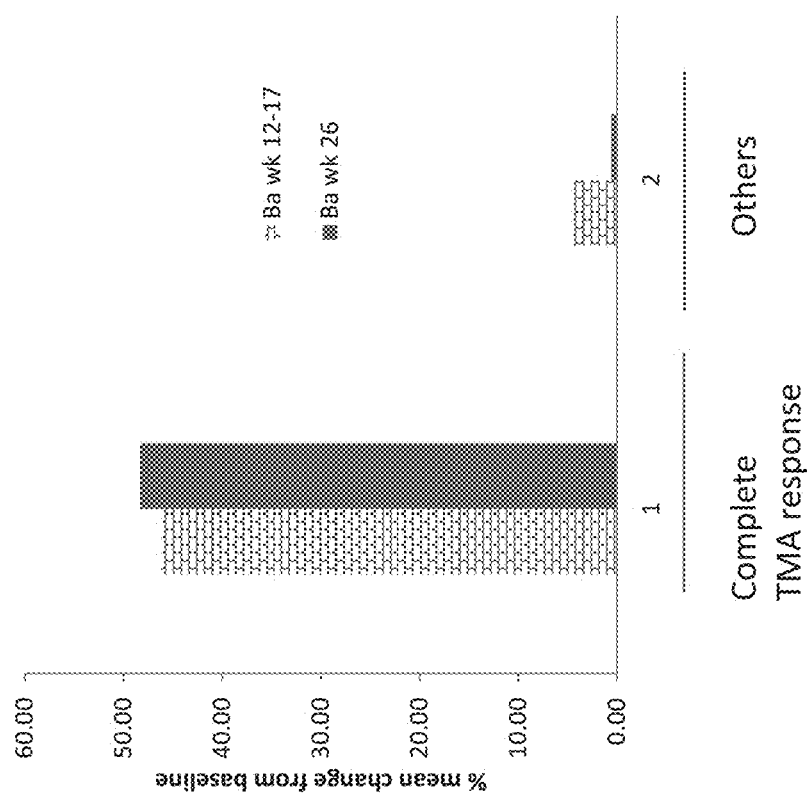
FIG. 12 is a bar graph depicting the mean percentage change in plasma Ba levels in eculizumab-treated aHUS patients experiencing a complete TMA response and those eculizumab-treated aHUS patients who do not (others).

Eculizumab-treated aHUS patients having a greater reduction in plasma Ba levels more frequently achieved a complete TMA response (e.g., normalization of hematologic parameters (e.g., platelet count and LDH levels) and preservation of renal function). For example, 72.7% of patients attained a complete TMA response by weeks 12-17, and 85.29% of the patients achieved a complete TMA response by week 26. As shown in FIG. 12, these patients showed a greater mean percentage reduction in plasma Ba concentration than patients who did not attain a complete TMA response (p=0.0018 and p=0.006, respectively).

Post-Treatment eGFR

Figure 16:
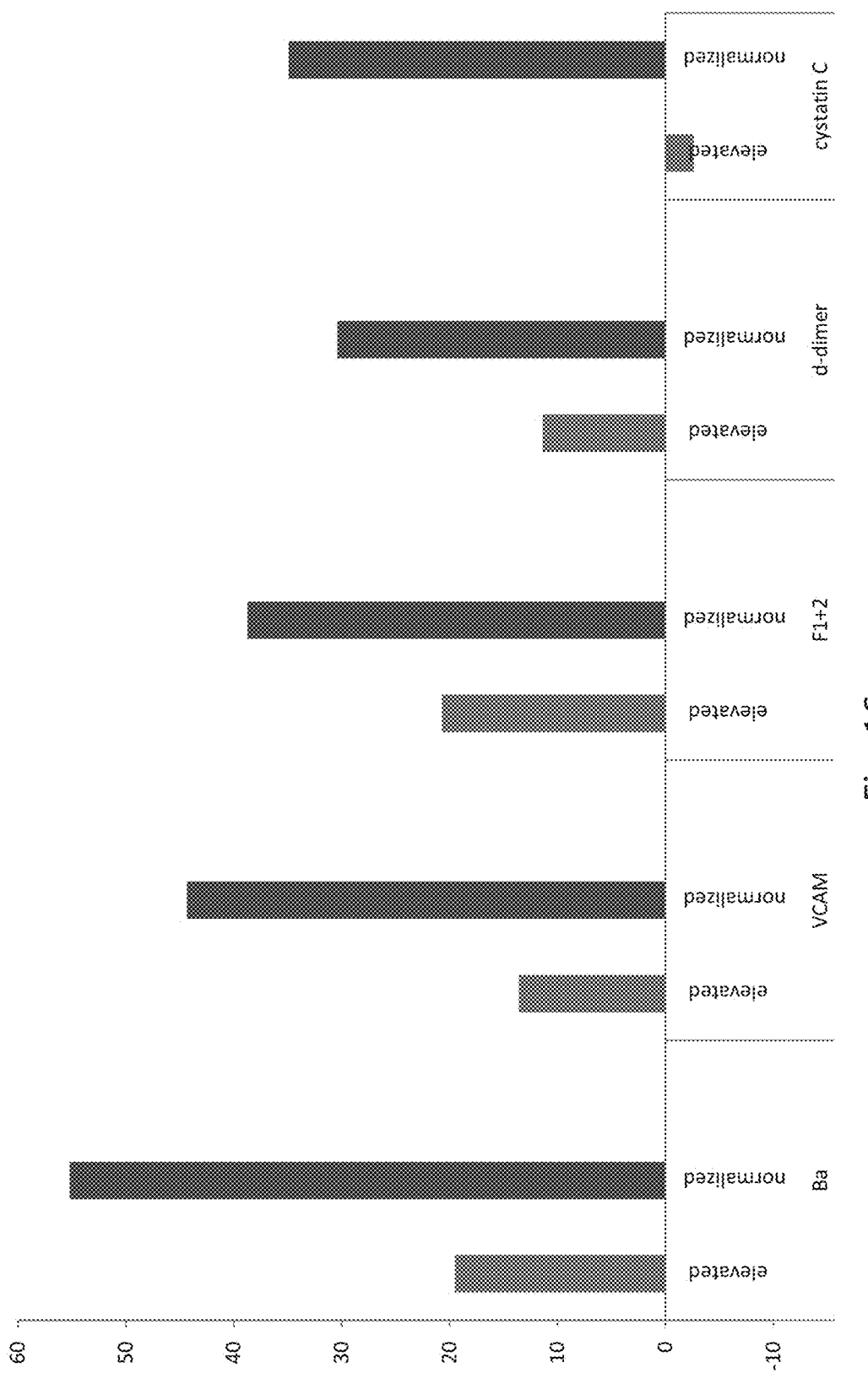
FIG. 16 is a series of bar graphs depicting the mean change in baseline eGFR (mL/min/1.73 m$^2$) in aHUS patients who achieve normalized levels of various biomarkers (plasma Ba, serum VCAM-1, plasma F1+2, plasma d-dimer, and urinary cystatin C) following eculizumab treatment as compared to aHUS patients in whom the concentration of these biomarkers remain elevated.

Also observed was a relationship between the reduction and/or normalization of certain biomarkers and an improvement in eGFR. For example, a significantly greater improvement (Table 10) in eGFR (e.g., eGFR≥15 mL/min/1.73 m$^2$ sustained for at least two consecutive measurements obtained at least four weeks apart) was observed among patients with normalized MCP-1, IL-6, and IFN-γ (at weeks 4-6); normalized VCAM-1, CXCL10, CXCL9, and Ba (at weeks 12-17), and normalized Ba, urinary β2M, urinary CysC, vWF, D-dimer, clusterin, CXCL10, CXCL9, urinary FABP-1, and others (at week 26) (Table 10). See also FIG. 16.

TABLE 10

| Week post-initiation of treatment w/ eculizumab | Normalized Biomarker | p value |
|---|---|---|
| 1-2.5 | * | * |
| 4-6 | MCP-1 | 0.0002 |
|  | IL-6 | 0.0251 |
|  | VCAM-1 | 0.0166 |
| 12-17 | VCAM-1 | 0.0003 |
|  | CXCL-10 | 0.0071 |
|  | Ba | 0.0299 |
|  | CXCL-9 | 0.0441 |
| 26 | VCAM-1 | <0.0001 |
|  | Cystatin C | <0.0001 |
|  | Ba | 0.0002 |
|  | U-β2m | 0.0013 |
|  | CXCL9 | 0.0027 |
|  | CXCL10 | 0.0172 |
|  | vWF | 0.0052 |
|  | D-dimer | 0.0224 |
|  | L-FABP | 0.0230 |
|  | Clusterin | 0.0300 |
|  | F1 + 2 | 0.0460 |

Example 3

Baseline Levels of Selected aHUS Biomarker Proteins in aHUS Patients

At baseline, prior to eculizumab treatment, substantial evidence of significant complement activation, vascular inflammation/damage, and organ injury was observed in aHUS patients regardless of use of plasma exchange/plasma infusion or normal laboratory values for platelet count, Hp or LDH. As evidenced by the data set forth in Table 11, the concentrations of aHUS biomarkers of complement activity, vascular inflammation, endothelial activation and damage, coagulation, and renal injury were significantly elevated in aHUS patients compared to healthy subjects.

TABLE 11

| Disease Process | Biomarker (NHV range; units) | Median Level at BL [range] (P Value vs. NHV**) | n/N (%) Elevated at BL | Fold increase over NHV at BL |
|---|---|---|---|---|
| CAP Activation | Plasma Ba (388.0-588.0 ng/mL) | 2676.4 [935.0-3668.0] (<0.0001) | 35/35 (100) | 5.53 |
| Terminal Complement Activation | U-05a (0.0-0.7 ng/mg U-creat) | 9.00 [0.3-76.6] (0.0007) | 26/29 (89.7) | 45 |
|  | U-sC5b-9 (0.0-0.6 ng/mg U-creat) | 30.50 [0.2-665.7] (0.0025) | 23/27 (85.2) | 305 |
| Inflammation | sTNFR1 (407.3-1391.3 pg/mL) | 17616.85 [4008.5-54158.2] (<0.0001) | 38/38 (100) | 18.71 |
| Endothelial Activation | sVCAM-1 (159.2-444.7 ng/mL) | 659.75 [375.4-1865.5] (<0.0001) | 36/38 (94.7) | 1.99 |
| Endothelial Damage | TM (2.0-3.6 ng/mL) | 10 [3.4-24.1] (<0.0001) | 33/34 (97.1) | 3.64 |
| Coagulation | F1 + 2 (82.9-305.5 pmol/L) | 1017.55 [217.7-5774.0] (<0.0001) | 36/38 (94.7) | 5.46 |
|  | D-dimer (157.0-395.9 µg/L) | 2735 [330.0-44100.0] (0.0002) | 34/36 (94.4) | 9.84 |
| Renal Injury | U-clusterin (5.7-437.1 ng/mg U-creat) | 1232.30 [129.9-6091.2] (<0.0001) | 24/29 (82.8) | 8.62 |
|  | U-TIMP-1 (0.0-5.4 ng/mg U-creat) | 23.8 [1.4-230.4] (0.0003) | 22/29 (75.9) | 39.67 |
|  | U-L-FABP-1 (0.0-16.9 ng/mg U-creat) | 58.00 [3.7-1309.8] (0.0130) | 22/29 (75.9) | 48.33 |
|  | U-β2m (0.0-2.7 µg/mg U-creat) | 18.4 [0.4-127.7] (<0.0001) | 20/28 (71.4) | 46 |
|  | U-cystatin-C (0.3-301.3 ng/mg U-creat) | 1256.9 [14.3-7189.6] (0.0001) | 18/26 (69.2) | 23.85 |

NHV means normal human value or concentration for a given aHUS biomarker protein recited in the Table.
"creat" means creatinine, the concentration of which is used to normalize certain biomarker concentrations recited in the table.
CAP refers to alternative pathway of complement (see above).
"BL" refers to "baseline", i.e., prior to treatment with eculizumab.
"N" is the total number of patients analyzed for a given disease process and biomarker.
"n" is the number of "N" patients in which a given biomarker was elevated.
"U" indicates that the analyte was measured in urine.
* P values were calculated using a Wilcoxon Rank Sum test, testing for a difference between groups.

In addition, the inventors observed that there was no statistical significance between the baseline elevated levels of certain aHUS biomarkers observed in patients who had received or were receiving plasma exchange (PE) or plasma infusion (PI) therapy as compared to the level of elevation of the aHUS biomarkers in patients who did not receive PE or PI therapy. For example, the concentration of Ba, sTNFR1, sVCAM-1, and D-dimer were not reduced or normalized in patients who had received PE/PI therapy (FIGS. 17A-D). Note that only 3 of 26 patients analyzed in the data presented in FIGS. 17A-D did not receive PE/PI. The majority of patients (n=23) had elevated levels of Cystatin C, as compared to normal healthy volunteers. Cystatin C being a renal injury marker (glomerular injury), it is possible that the patients who did not receive PE/PI had less damage to their kidneys and thus had reduced levels of renal injury-related biomarker proteins in their urine.

Similarly, at baseline, prior to eculizumab therapy, the concentration of protein markers of complement activation (e.g., Ba), inflammation (e.g., sTNFR1), endothelial cell activation (sVCAM-1), coagulation (D-dimer), and renal injury (cystatin-C) were elevated in patients with aHUS having normal platelet counts. See FIGS. 18A-E. And patients with normal Hp and LDH levels showed evidence of ongoing complement activation, inflammation, endothelial cell activation, coagulation and renal injury (see FIGS. 19A-E).

In view of the foregoing, the concentration of biomarkers reflecting complement activity, vascular inflammation, endothelial activation and damage, coagulation and renal injury were chronically elevated in patients with aHUS compared to normal healthy subjects. Patients with aHUS receiving PE/PI showed strong evidence of significant ongoing complement activation, vascular inflammation, endothelial activation, coagulation and renal injury. While PE/PI may transiently maintain normal platelet count and LDH in some patients, the above results demonstrate that the underlying complement dysregulation and TMA processes persist. Despite normal laboratory values for platelet count, LDH, and Hp, these studies indicate that significant ongoing complement activation, vascular inflammation, endothelial activation, coagulation and renal injury exist in aHUS patients.

Example 4

Effects of Sustained Treatment with Eculizumab on aHUS Biomarker Concentrations

Figure 20A:
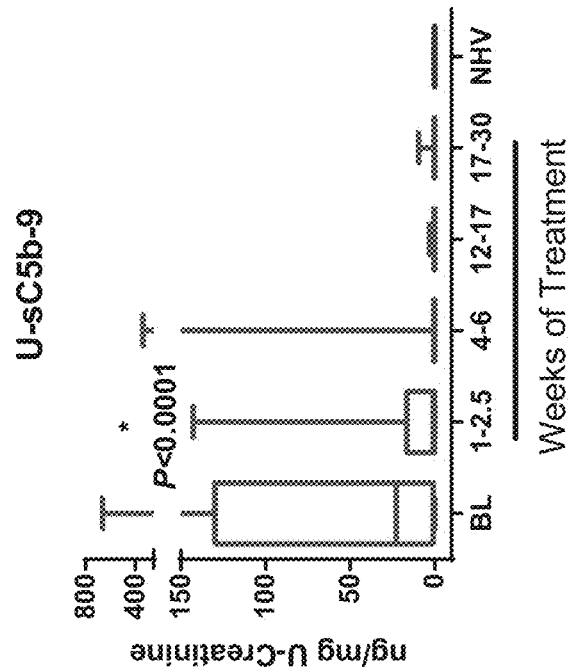
FIGS. 20A-B are Box-Whisker plots depicting the longitudinal effects of sustained eculizumab treatment on terminal complement activation in aHUS patients.
Figure 20B:
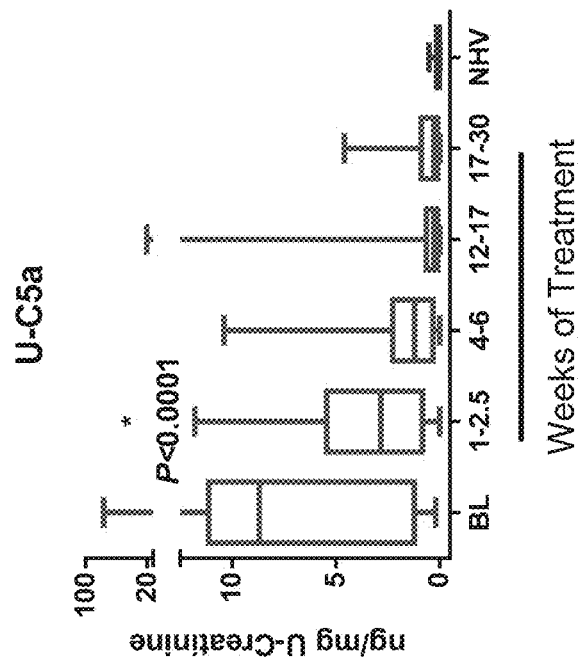

The inventors observed that sustained eculizumab treatment inhibits chronic elevated complement activation and terminal complement mediated renal injury, and reduces inflammation, endothelial damage and thrombotic risk in patients with aHUS. For example, sustained eculizumab treatment rapidly and completely inhibited terminal complement activation as indicated by the reduction in the concentration of both C5a and sC5b-9 (e.g., urinary C5a and sC5b-9). See FIGS. 20A-B. At baseline, patients with aHUS showed significant terminal complement activation compared with NHV, despite use of PE/PI or normal platelet counts in some patients. In fact, aHUS patients demonstrated 45-fold higher urinary C5a and 305-fold higher urinary sC5b-9 levels than NHV. However, during sustained eculizumab treatment, all aHUS patients demonstrated rapid and potent terminal complement blockade, with complete normalization of pathogenic terminal complement activation products and no difference in levels relative to NHV.

Figure 21A:
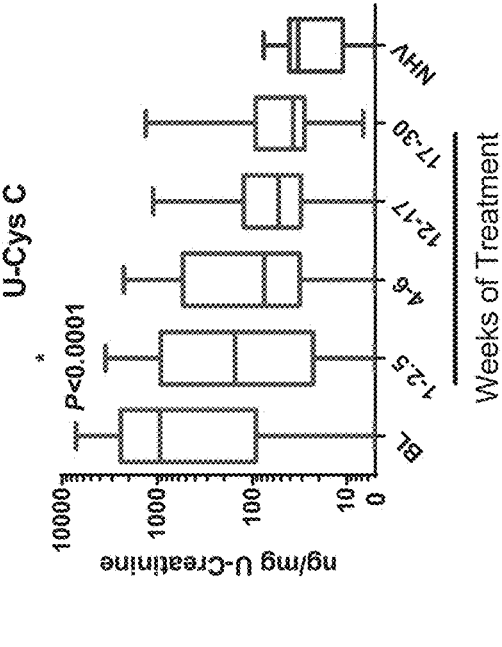
FIGS. 21A-C are Box-Whisker plots depicting the longitudinal effects of sustained eculizumab treatment on the concentration of biomarker proteins associated with renal injury in aHUS patients.
Figure 21B:
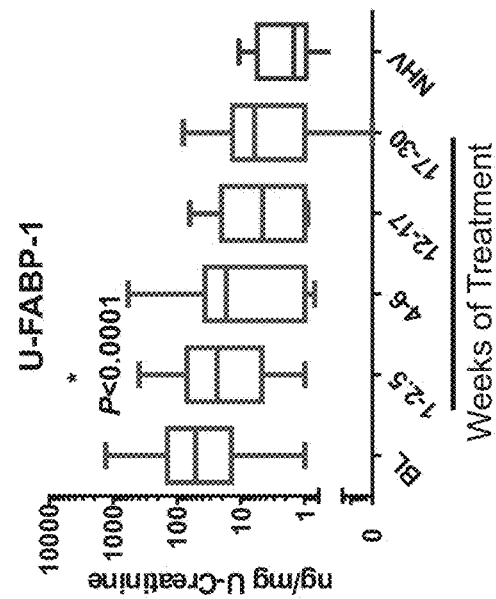
Figure 21C:
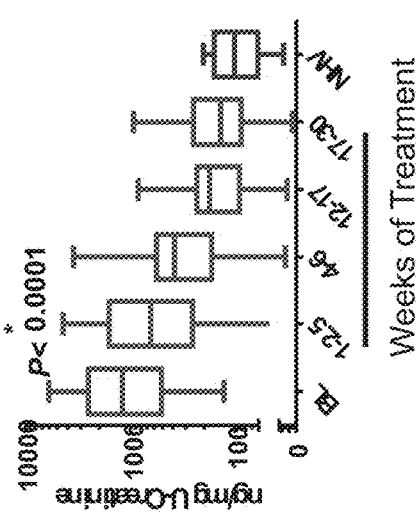

Furthermore, sustained eculizumab treatment normalized the concentration of biomarker proteins of renal injury (FIGS. 21A-C). Prior to initiating eculizumab therapy, the majority of patients had elevated levels of biomarkers of: tubular interstitial injury and deterioration of renal function (e.g., L-FABP-1, ~48 fold higher than NHV), glomerular filtration (e.g., cystatin C, ~24-fold higher than NHV), proximal tubular injury (e.g., clusterin, 8.6 fold higher than NHV). However, sustained treatment with eculizumab dramatically reduced the urinary concentrations of FABP-1 (by up to 100%), cystatin C (by up to 99%), and clusterin (by up to 98%). This reduction was significant across all timepoints ($P<0.0001$ for all) and the reduced concentration of all renal injury markers was no different than levels in NHV. Additional renal injury markers (e.g., TIMP-1 and $\beta$2-microglobulin) also normalized (see above under Example 2). These results suggest that organ ischemia and damage may be entirely terminal complement dependent and confirms clinical data demonstrating that sustained inhibition of complement-mediated TMA led to clinically meaningful eGFR improvement and discontinuation of dialysis.

Figure 22:
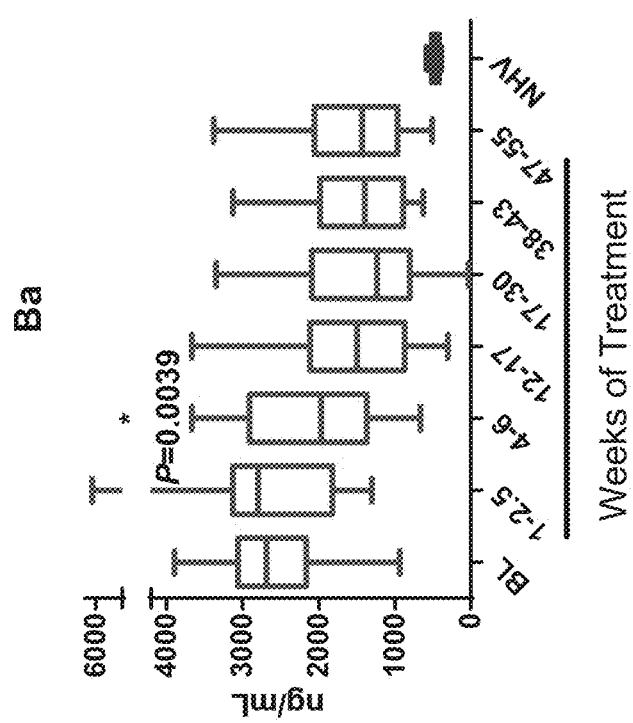
FIG. 22 is a Box-Whisker plot depicting the longitudinal effects of sustained eculizumab treatment on complement alternative pathway activation in aHUS patients. The change over time in the concentration of Ba (ng/mL) in the plasma of aHUS patients following eculizumab treatment is shown along with the concentration of plasma Ba in normal healthy volunteers (NHV). The Box-Whisker plot shows median, $25^{th}$, and $75^{th}$ percentiles and range. *First time point at which levels were significantly reduced vs. baseline (BL); P values versus baseline at each timepoint were calculated using a restricted maximum likelihood-based repeated measures approach (Mixed Model). P values compared with NHV were calculated using the Wilcoxon Rank Sum test.

Sustained treatment with eculizumab also significantly reduces complement alternative pathway activation (see FIG. 22). All patients with aHUS showed significant systemic CAP activation upstream of C5, with 5.5-fold higher levels of Ba compared with NHV, prior to eculizumab treatment. However, following initiation of eculizumab therapy, the concentration of upstream biomarkers of CAP activation (e.g., Ba levels) was reduced by 30% and reduction after week 4-6 was significant across all timepoints ($p<0.005$) as compared with the concentration of the markers in NHV. Yet Ba levels did not normalize in aHUS patients treated with eculizumab, suggesting that CAP activation persists, reflecting the underlying complement dysregulation in patients with aHUS. To be clear, though, terminal complement blockade with eculizumab protected patients from the clinical consequences of ongoing CAP activation.

In addition, chronic treatment of aHUS patients with eculizumab resulted in significantly reduced concentrations of biomarkers associated with inflammation, endothelial activation, and tissue damage (FIGS. 23A-C). Serum sTNFR1 levels were elevated (18.7-fold higher than NHV levels) in 100% of patients with aHUS at baseline. Sustained treatment with eculizumab significantly reduced sTNFR1 up to 94%. The reduction in the concentration of these biomarkers at week 4-6 was significant across all timepoints ($P<0.0001$). Soluble VCAM-1 and TM levels were elevated in >95% of aHUS patients at baseline by 2-fold and 3.6-fold, respectively, as compared to NHV, demonstrating significant endothelial cell activation and damage prior to eculizumab therapy. TM and sVCAM-1 concentrations were also significantly reduced during eculizumab treatment. After week 12-17, reduction in the concentration of biomarkers of endothelial damage was significant across all later timepoints (TM; $P<0.0001$), but still modestly elevated compared to NHV. Dramatically reduced soluble TM levels may reflect restoration of membrane bound TM, which is protective against thrombotic risk.

Figure 24A:
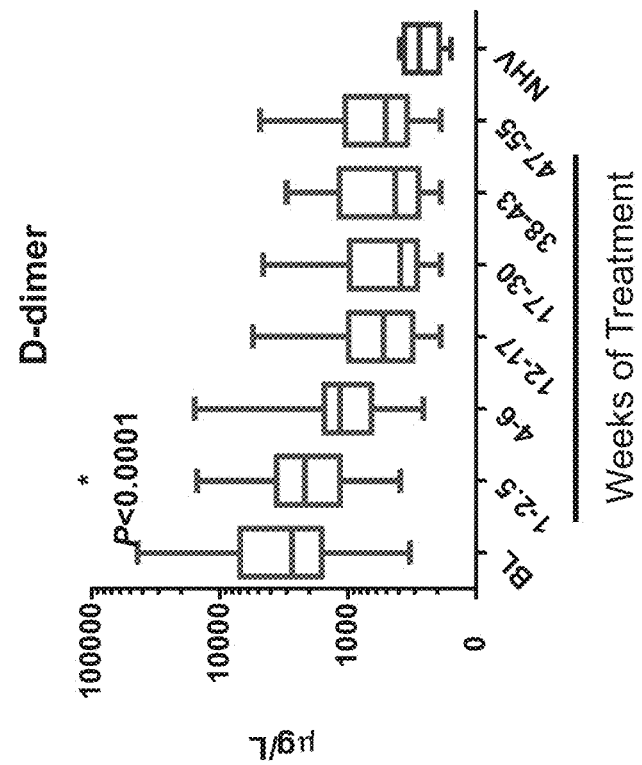
FIGS. 24A-B are Box-Whisker plots depicting the longitudinal effects of sustained eculizumab treatment on the concentration of biomarker proteins associated with thrombosis and coagulation in aHUS patients.
Figure 24B:
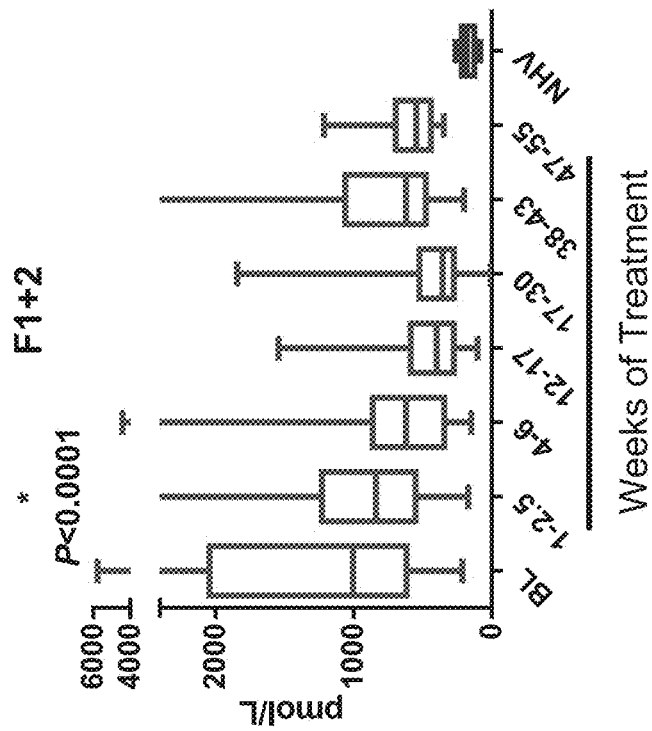

Finally, chronic treatment with eculizumab rapidly and significantly reduced the concentration of biomarkers associated with thrombotic risk and coagulation (FIGS. 24A-B). The concentration of coagulation biomarkers F1+2 and D-dimer were significantly elevated (5.5-fold and 9.8 fold higher than NHV) at baseline in greater than 94% of patients with aHUS ($P<0.0001$ and $P=0.0002$, respectively). Yet F1+2 and D-dimer were significantly reduced at 2.5 weeks post initiation of treatment with eculizumab. The concentration of F1+2 decreased by up to 88% ($P<0.05$ for all timepoints) and the D-dimer concentration was reduced by up to 99% ($P<0.0001$ for all timepoints) with sustained eculizumab treatment. However, these two markers remained modestly elevated over the respective concentrations in normal healthy subjects.

CONCLUSIONS

In view of the foregoing data, the inventors were able to draw a number of conclusions. First, at baseline, elevated levels of all thrombotic microangiopathy (TMA) biomarkers were evident in patients with aHUS as compared to the levels in samples from normal healthy volunteers (NHV). In all patient groups—including those receiving PE/PI or those with normal platelets, Hp or LDH—patients with aHUS demonstrated significant elevation, over NHVs, in measures of: terminal complement activation (45-305 fold higher than NHV levels); vital organ damage; alternative pathway of complement activation (e.g., as represented by Ba levels; 5.5-fold higher than NHV levels); vascular inflammation; endothelial activation and damage; and coagulation.

Sustained eculizumab treatment of aHUS patients significantly reduced and normalized highly elevated markers of terminal complement activation. Inhibition of terminal complement activation with eculizumab also dramatically reduced and normalized markers of organ damage. Upstream biomarkers of alternative pathway activation were also significantly reduced, but did not normalize. And low levels of alternative pathway activation persisted in treated patients, reflecting the underlying complement dysregulation in patients with aHUS. That said, the data clearly indicate that terminal complement blockade with eculizumab protects aHUS patients from the clinical consequences of ongoing alternative pathway activation.

Moreover, sustained eculizumab treatment also resulted in: (i) significant and sustained reduction of markers of vascular inflammation (by up to 94%); (ii) significant inhibition of markers of endothelial activation (by up to 60%); (iii) significant and sustained reduction in markers of endothelial damage (by up to 77%) to near normal levels, demonstrating a clear relationship between terminal complement activation and endothelial damage; and (iv) marked reduction (by up to 99%) of the concentration of biomarkers of thrombotic risk, likely decreasing the potential for clot formation and thus reducing incidence of TMA in these patients. The inventors conclude, while not being bound by any theory or mechanism of action, that inhibition of terminal complement activation with eculizumab must be sustained, as loss of terminal complement inhibition in aHUS would lead to a rapid increase in severely amplified terminal complement activation, subsequently leading to: increase in underlying subclinical endothelial activation, significant acceleration of endothelial damage, marked increase in thrombotic risk, and an early and ongoing risk of catastrophic vascular ischemia and vital organ damage. Moreover, these data indicate that the renal injury, vascular inflammation, and endothelial damage and activation are in whole or in part dependent on terminal complement activity, which activity is effectively and safely inhibited using eculizumab.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, or process step or steps, to the objective, spirit and scope of the present disclosure. All such modifications are intended to be within the scope of the disclosure.

What is claimed is:

1. A method for treating a patient having atypical hemolytic uremic syndrome (aHUS) whose blood or urine has been determined to contain elevated levels at least two aHUS-associated biomarker proteins selected from the group consisting of TNFR1, MCP-1, IFN-γ, IL-6, a proteolytic fragment of complement component factor B, soluble C5b9 (sC5b9), prothrombin fragment F1+2, d-dimer, thrombomodulin, VCAM-1, von Willebrand Factor (vWF), complement component C5a, β2 microglobulin (β2M), clusterin, cystatin C, NAG, TIMP-1, NGAL, fatty acid binding protein 1 (FABP-1), albumin, CXCL9, KIM-1 and CCL5, soluble CD40 ligand (sCD40L), ICAM-1, IL-1 beta, IL-12 p70, IL-8, and vascular endothelial cell growth factor (VEGF), the method comprising administering to the patient an inhibitor of complement C5 in an amount and with a frequency sufficient to reduce the concentration of the at least two aHUS-associated biomarker proteins compared to the concentration measured in the patient's blood or urine prior to treatment with the complement C5 inhibitor.

2. The method of claim 1, wherein the subject:
   (a) has received dialysis at least once within the three months immediately prior to treatment with the complement C5 inhibitor; or
   (b) is experiencing a first acute aHUS manifestation.

3. The method of claim 1, wherein the reduced concentration of the at least two aHUS-associated biomarker proteins occurs within two weeks or two months after the first administration of the complement C5 inhibitor.

4. The method of claim 1, wherein the subject is chronically treated with a complement C5 inhibitor.

5. The method of 1, wherein the complement C5 inhibitor is selected from the group consisting of a small molecule, a polypeptide, a polypeptide analog, a peptidomimetic, and an aptamer.

6. The method of 1, wherein the complement C5 inhibitor is selected from the group consisting of MB12/22, MB12/22-RGD, ARC187, ARC1905, SSL7, and OmCI.

7. The method of claim 1, wherein the complement C5 inhibitor is an antibody, or an antigen-binding fragment thereof.

8. The method of claim 7, wherein the antibody, or antigen-binding fragment thereof, is selected from the group consisting of a humanized antibody, a recombinant antibody, a diabody, a chimerized or chimeric antibody, a monoclonal antibody, a deimmunized antibody, a fully human antibody, a single chain antibody, an Fv fragment, an Fd fragment, an Fab fragment, an Fab' fragment, and an F(ab')$_2$ fragment.

9. The method of claim 7, wherein the antibody, or antigen-binding fragment thereof, binds to complement component C5 and inhibits cleavage of C5 into fragments C5a and C5b.

10. The method of claim 9, wherein the antibody is eculizumab or a variant of eculizumab.

11. The method of claim 10, wherein the antigen-binding fragment is pexelizumab.

12. The method of claim 1, wherein at least one of the aHUS-associated biomarkers is selected from the group consisting of: proteolytic fragment Ba of factor B, TNFR1, VCAM-1, D-dimer, thrombomodulin, and cystatin C.

13. The method of claim 1, wherein the at least two aHUS-associated biomarker proteins are measured using an immunoassay, such as an enzyme-linked immunosorbent assay (ELISA) or a radioimmunoas say (RIA).

14. The method of claim 1, wherein the biological fluid is blood, a blood fraction, or urine.

15. The method of claim 14, wherein the blood fraction is serum or plasma.

16. The method of claim 1, wherein:
  (i) the concentration of at least one aHUS-associated biomarker is measured in two or more types of biological fluid; or
  (ii) the concentration of a first of the at least two aHUS-associated biomarker proteins is measured in one type of biological fluid and the concentration of a second of the at least two aHUS biomarker proteins is measured in a second type of fluid.

17. The method of claim 1, wherein:
  (i) the concentration of CXCL9, IFN-γ, MCP-1, CCL5, sCD40L, or sTNFR1 in the serum of the subject is determined;
  (ii) the concentration of at least one of (β2 microglobulin (β2M), clusterin, cystatin C, NAG, TIMP-1, NGAL, fatty acid binding protein 1 (FABP-1), CXCL9, albumin, and KIM-1 in the urine of the subject is determined;
  (iii) the concentration of NGAL, a proteolytic fragment of complement component factor B, soluble C5b9 (sC5b9), prothrombin fragment F1+2, D-dimer, thrombomodulin, or von Willebrand Factor (vWF) in the plasma of the subject is determined; and/or
  (iv) the concentration of Ba in plasma obtained from the subject is determined.

18. The method of claim 1, wherein the normal concentration of sTNFR1 is less than 2000 pg/mL.

19. The method of claim 1, wherein the concentration of sTNFR1 in the biological sample is deemed elevated when it is:
  (i) at least two fold greater than the normal concentration of sTNFR1; or
  (ii) at least 10,000 μg/mL.

* * * * *

UNITED STATES PATENT AND TRADEMARK OFFICE
CERTIFICATE OF CORRECTION

PATENT NO.       : 9,494,601 B2
APPLICATION NO.  : 15/013833
DATED            : November 15, 2016
INVENTOR(S)      : Susan Faas McKnight et al.

It is certified that error appears in the above-identified patent and that said Letters Patent is hereby corrected as shown below:

On the Title Page

Item (56)

On Page 2, in Column 1, under "Other Publications", Line 2, delete "Hemoglobinuira" and insert -- Hemoglobinuria --, therefor.

On Page 2, in Column 1, under "Other Publications", Line 4, delete "rom" and insert -- from --, therefor.

On Page 2, in Column 2, under "Other Publications", Line 26, delete "Insrum." and insert -- Instrum. --, therefor.

On Page 2, in Column 2, under "Other Publications", Line 67, delete "Eculizumb,"" and insert -- Eculizumab," --, therefor.

On Page 3, in Column 2, under "Other Publications", Line 51, delete "eculizuluab" and insert -- eculizumab --, therefor.

On Page 4, in Column 1, under "Other Publications", Line 5, delete "hemglobinuria,"" and insert -- hemoglobinuria," --, therefor.

On Page 4, in Column 1, under "Other Publications", Line 62, delete "Investogational" and insert -- Investigational --, therefor.

On Page 4, in Column 2, under "Other Publications", Line 41-42, delete "haelnolytic-urelnic syndrolne" and insert -- haemolytic-uremic syndrome --, therefor.

Signed and Sealed this
Fourteenth Day of February, 2017

Michelle K. Lee
*Director of the United States Patent and Trademark Office*

CERTIFICATE OF CORRECTION (continued)
U.S. Pat. No. 9,494,601 B2

On Page 4, in Column 2, under "Other Publications", Line 54, delete "noctumal" and insert -- nocturnal --, therefor.

On Page 5, in Column 1, under "Other Publications", Line 2, delete "Facto-Q" and insert -- Factor-α --, therefor.

On page 5, in Column 1, under "Other Publications", Line 10, delete "Medelian" and insert -- Mendelian --, therefor.

In the Specification

In Column 3, Line 28, delete "P2" and insert -- β2 --, therefor.

In Column 5, Line 12, delete "P2" and insert -- β2 --, therefor.

In Column 5, Line 52, delete "P2" and insert -- β2 --, therefor.

In Column 6, Line 1, delete "(32" and insert -- β2 --, therefor.

In Column 6, Line 15, delete "P2" and insert -- β2 --, therefor.

In Column 6, Line 28, delete "P2" and insert -- β2 --, therefor.

In Column 7, Line 9, delete "P2" and insert -- β2 --, therefor.

In Column 7, Line 21, delete "P2" and insert -- β2 --, therefor.

In Column 8, Line 65, delete "P2" and insert -- β2 --, therefor.

In Column 9, Line 14, delete "P2" and insert -- β2 --, therefor.

In Column 11, Line 44, delete "anaphylatoxic" and insert -- anaphylatoxin --, therefor.

In Column 11, Line 46, delete "CSb." and insert -- C5b. --, therefor.

In Column 12, Line 22, delete "MB 12/22," and insert -- MB12/22, --, therefor.

In Column 13, Line 45, delete "(32" and insert -- β2 --, therefor.

In Column 13, Line 65, delete "P2" and insert -- β2 --, therefor.

In Column 14, Line 44, delete "P2" and insert -- β2 --, therefor.

In Column 14, Line 57, delete "P2" and insert -- β2 --, therefor.

CERTIFICATE OF CORRECTION (continued)
U.S. Pat. No. 9,494,601 B2

In Column 15, Line 5, delete "P2" and insert -- β2 --, therefor.

In Column 15, Line 21, delete "P2" and insert -- β2 --, therefor.

In Column 15, Line 48, delete "P2" and insert -- β2 --, therefor.

In Column 18, Line 10, delete "(32" and insert -- β2 --, therefor.

In Column 20, Line 12, delete "anaphylatoxic" and insert -- anaphylatoxin --, therefor.

In Column 20, Line 59, delete "difunisal," and insert -- diflunisal, --, therefor.

In Column 29, Line 14, delete "sCSb-9" and insert -- sC5b-9 --, therefor.

In Column 43, Line 25, delete "radioimmunoas says," and insert -- radioimmunoassays, --, therefor.

In Column 48, Line 10, delete "anaphylatoxic" and insert -- anaphylatoxin --, therefor.

In Column 51, Line 6, delete "$10^{11}10^{12}$," and insert -- $10^{11}$, $10^{12}$, --, therefor.

In Column 51, Line 7, delete "M." and insert -- $M^{-1}$. --, therefor.

In Column 53, Line 64, delete "sialastic" and insert -- silastic --, therefor.

In Column 57, Line 49, delete "*JAm*" and insert -- *J Am* --, therefor.

In Column 74, Line 27, delete "-clusterm" and insert -- -clusterin --, therefor.

In the Claims

In Column 86, Line 40, in Claim 5, after "of" insert -- claim --.

In Column 86, Line 44, in Claim 6, after "of" insert -- claim --.

In Column 87, Line 6, in Claim 13, delete "radioimmunoas say" and insert -- radioimmunoassay --, therefor.

In Column 88, Line 1, in Claim 17, delete "(32" and insert -- β2 --, therefor.

In Column 88, Line 21, in Claim 19, delete "μg/mL." and insert -- pg/mL. --, therefor.